United States Patent
Oppermann et al.

(10) Patent No.: US 6,297,213 B1
(45) Date of Patent: *Oct. 2, 2001

(54) OSTEOGENIC DEVICES

(75) Inventors: Hermann Oppermann; Thangavel Kuberasampath, both of Medway; David C. Rueger, West Roxbury; Engin Ozkaynak, Milford, all of MA (US)

(73) Assignee: Stryker Corporation, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/074,299

(22) Filed: May 7, 1998

Related U.S. Application Data

(63) Continuation of application No. 08/417,071, filed on Apr. 4, 1995, now Pat. No. 5,814,604, which is a continuation of application No. 08/145,812, filed on Nov. 1, 1993, now Pat. No. 5,750,651, which is a division of application No. 07/995,345, filed on Dec. 22, 1992, now Pat. No. 5,258,494, which is a division of application No. 07/315,342, filed on Feb. 23, 1989, now Pat. No. 5,011,691, which is a continuation-in-part of application No. 07/232,630, filed on Aug. 15, 1988, now abandoned, which is a continuation-in-part of application No. 07/179,406, filed on Apr. 8, 1988, now Pat. No. 4,968,590.

(51) Int. Cl.[7] .............................. A61K 38/18; C07K 14/51

(52) U.S. Cl. ................................ 514/12; 514/2; 424/423; 424/426; 530/350; 530/395

(58) Field of Search .................................. 424/423, 426; 514/2, 21; 530/350, 395

(56) References Cited

U.S. PATENT DOCUMENTS

| | | | | |
|---|---|---|---|---|
| 4,120,730 | * | 10/1978 | Trojer et al. . | |
| 4,294,753 | | 10/1981 | Urist ........................................ | 530/395 |
| 4,394,370 | | 7/1983 | Jefferies ................................... | 424/15 |
| 4,434,094 | | 2/1984 | Seyedin et al. ......................... | 530/416 |
| 4,455,256 | | 6/1984 | Urist ........................................ | 530/350 |
| 4,563,350 | | 1/1986 | Nathan et al. .......................... | 424/95 |
| 4,563,489 | | 1/1986 | Urist ........................................ | 524/21 |
| 4,774,322 | | 9/1988 | Seyedin et al. ......................... | 530/353 |
| 4,804,744 | | 2/1989 | Sen .......................................... | 530/395 |
| 4,810,691 | | 3/1989 | Seyedin et al. ......................... | 514/2 |
| 4,843,063 | | 6/1989 | Seyedin et al. ......................... | 514/2 |
| 4,877,864 | | 10/1989 | Wang et al. ............................ | 530/324 |
| 5,011,691 | * | 4/1991 | Oppermann et al. . | |
| 5,013,649 | | 5/1991 | Wang et al. ............................ | 435/69.1 |
| 5,106,626 | | 4/1992 | Parsons et al. ........................ | 424/423 |
| 5,106,748 | | 4/1992 | Wozney et al. ....................... | 435/252.3 |
| 5,108,753 | * | 4/1992 | Kuberasampath et al. . | |
| 5,108,922 | | 4/1992 | Wang et al. ............................ | 435/240 |
| 5,116,738 | | 5/1992 | Wang et al. ............................ | 435/69.1 |
| 5,141,905 | | 8/1992 | Rosen et al. ........................... | 435/69.1 |
| 5,154,931 | | 10/1992 | Kruger et al. .......................... | 424/549 |
| 5,162,114 | * | 11/1992 | Kuberasampath et al. . | |
| 5,166,058 | | 11/1992 | Wang et al. ............................ | 435/69.1 |
| 5,171,574 | * | 12/1992 | Kuberasampath et al. . | |
| 5,187,076 | | 2/1993 | Wozney et al. ....................... | 435/69.1 |
| 5,344,654 | * | 9/1994 | Rueger et al. . | |
| 5,354,557 | * | 10/1994 | Oppermann et al. . | |
| 5,496,552 | * | 3/1996 | Kuberasampath et al. . | |
| 5,674,292 | * | 10/1997 | Tucker et al. . | |
| 5,958,441 | * | 9/1999 | Oppermann et al. . | |
| 6,013,856 | * | 1/2000 | Tucker et al. . | |
| 6,077,988 | * | 6/2000 | Kuberasampath et al. . | |
| 6,110,482 | * | 8/2000 | Khouri et al. . | |

FOREIGN PATENT DOCUMENTS

| | | |
|---|---|---|
| 0128041 | 12/1984 | (EP) . |
| 0148155 | 2/1985 | (EP) . |
| 0169016 | 1/1986 | (EP) . |
| 0182483 | 5/1986 | (EP) . |
| 0212474 | 4/1987 | (EP) . |
| 8505274 | 12/1985 | (WO) . |
| 8600526 | 1/1986 | (WO) . |
| 8800205 | 1/1988 | (WO) . |
| 8909605 | 10/1989 | (WO) . |
| 8910409 | 11/1989 | (WO) . |
| 9003733 | 4/1990 | (WO) . |
| 9011366 | 10/1990 | (WO) . |
| 9102744 | 3/1991 | (WO) . |
| 9300049 | 1/1993 | (WO) . |

OTHER PUBLICATIONS

Canalis et al. (1980) Science 210: 1021–1023 "Stimulation of DNA and Collagen Synthesis by Autologous Growth Factor in Cultured Fetal Rat Calvaria."

Glowacki et al. (1981) Lancet 1:959–963 "Application of the Biological Principle of Induced Osteogenesis for Craniofacial Defects."

Reddi (1981) Collage Rel. Res. 1:209–226 "Cell Biology and Biochemistry of Endochondral Bone Development."

Sampath et al. (1981) Proc. Natl. Acad. Sci. USA 78:7599–7603 "Dissociative Extraction and Reconstitution of Extracellular Matrix Components Involved in Local Bone Differentiation."

Farley et al. (1982) Biochem. 21:3508–3513 "Human Skeletal Growth Factor: Characterization of Mitogenic Effect on Bone Cells In Vitro."

Maugh (1982) Science 217:819 "Human Skeletal Growth Factor Isolated."

(List continued on next page.)

Primary Examiner—Elizabeth Kemmerer
(74) Attorney, Agent, or Firm—Testa, Hurwitz & Thibeault, LLP

(57) ABSTRACT

Disclosed are 1) osteogenic devices comprising a matrix containing osteogenic protein and methods of inducing endochondral bone growth in mammals using the devices; 2) amino acid sequence data, amino acid composition, solubility properties, structural features, homologies and various other data characterizing osteogenic proteins, 3) methods of producing osteogenic proteins using recombinant DNA technology, and 4) osteogenically and chondrogenically active synthetic protein constructs.

Sampath et al. (1983) Proc. Natl. Acad. Sci. USA 80:6591–6595 "Homology of Bone–Inductive Proteins from Human, Monkey, Bovine, and Extracellular Matrix."

24 Claims, 30 Drawing Sheets

OTHER PUBLICATIONS

Seyedin et al. (1983) J. Cell Biol. 97:1950–1953 "In Vitro Induction of Cartilage–Specific Macromolecules by a Bone Extract."

Urist et al. (1983) Proc. Soc. Exp. Bio. Med. 173:194–199 "Human Bone Morphogenic Protein (hBMP)."

Simpson (1984) Trends Biochem. Sci. 9:527–530 "Growth Factors Which Affect Bone."

Urist et al. (1984) Clin. Orth. Rel. Res. 187:277–280 "β–tricalcium Phosphate Delivery System for Bone Morphogenetic Protein."

Urist et al. (1984) Proc. Natl. Acad. Sci. USA 81:371–375 "Purification of Bovine Bone Morphogenetic Protein by Hydroxyapatite Chromatography."

Centrella (1985) Proc. Natl. Acad. Sci. USA 82:7335–7339 "Transforming and Nontransforming Growth Factors are Present in Medium Conditioned by Fetal Rat Calvariae."

Klausner (1985) Biotechnology 3:567–568 "Collagen Corp. Isolates Cartilage Inducers."

Olson et al. (1985) Analyt. Biochem. 146:232–257 "Deglycosylation of Chondroitin Sulfate Proteoglycan by Hydrogen Fluoride in Pyridine."

Reddi (1985) J. Biomed. Materials Res. 19:233–239 "Implant–Stimulated Interface Reactions During Collagens Bone Matrix–Induced Bone Formation."

Sampath & Reddi (1985) Extracellular Matrix: Structure and Function (A.H. Reddi. Ed., Allen R. Liss, Publ., NY pp. 412–428) "Role of Extracellular Matrix Components in Cartilage and Bone Induction."

Seyedin et al. (1985) Proc. Natl. Acad. Sci. USA 82:2267–2271 "Purification and Characterization of Two Cartilage–Inducing Factors from Bovine Demineralized Bone."

Urist et al. (1987) Methods in Enzymology 146:294–312 "Preparation and Bioassay of Bone Morphogenetic Protein and Polypeptide Fragments".

Padgett et al. (1987) Nature 325:81–84 "A Transcript From A Drosophila Pattern Gene Predicts A Protein Homologous To The Transforming Growth Factor–β Family."

Sampath et al. (1987) Proc. Natl. Acad. Sci. USA 84:7109–7113 "Isolation of Osteogenin, An Extracellular Matrix–Associated, Bone–Inductive Protein, By Heparin Affinity Chromatography."

Weeks et al. (1987) Cell 51:861–867 "A Maternal mRNA Localized to the Vegetal Hemisphere in Xenopus Eggs Codes For A Growth Factor Related to TGF–β."

LeGendre et al. (1988) Biotechniques 6:154–159 "Direct Protein Microsequencing From Immobilon–P Transfer Membrane."

Wang et al. (1988) Calcified Tissue Int. (Suppl.) Ab No. 146, pp. A37 "Purification and Characterization of Cartilage and Bone Inducing Factors."

Wang et al. (1988) Proc. Natl. Acad. Sci. USA 85:9484–9488 "Purification and Characterization of other Distinct Bone–Inducing Factors."

Wozney et al. (1988) Calcified Tissue Int. (Suppl.) Ab No. 147 A37 "Identification Through Molecular Cloning of Factors Involved In Vivo Cartilage Formation."

Wozney et al. (1988) Science 242:1528–1534 "Novel Regulators of Bone Formation: Molecular Clones & Activities."

Lyons et al. (1989) Proc. Natl. Acad. Sci. USA 86:4554–4558 "Vgr–1, A Mammalian Gene Related To Zenopus Vg–1, Is a Member of the Transforming Growth Factor β Gene Superfamily."

Wang et al. (1990) Proc. Natl. Acad. Sci. USA 87:2220–2224 "Recombinant Human Bone Morphogenetic Protein Induces Bone Formation."

* cited by examiner

```
          10          20          30          40          50          60          70
GGAGGTATAGGAGCTCTCTCGATTTTAGCAAACCAGGAGTCCGAAGATCTAAGGAGAGCTGGGGGTTTGACTCC
       SacI                                          BglII
          85          95         105         115         125         135         145
GAGAGCTCGAGCAGTCCCAAGACCTGGTCTTGACTCTGACTCCACTCAGAGTTAGACTCCACGAGGCTGACTGTCTCCAGG
   SacI      PflMI
       XhoI      Tth111I
         160         170         180         190         200         210         220
GTCTACACCTCTAAGGGCGACACTGGGCTCAAGCAGCAGAGACTGCCGTTTCTATATGGGATGAGCCTTCACAGGGCAG
         235         245         255         265         275         285         295
CCAGTTGGGATGGGTGAGGTTGGCTGTGAGACATCAGAAACCCAAGTCAAATGCGCTTCAACCAGTAGAAAATT
         310         320         330         340         350         360         370
CACCAGCCCGCAGAGCTAAGGTTGGGTGGACATTAGGGTTGGTTGATCCAGGAGCTCAACAGTGTCCTCTGAGCC
         385         395         405         415         425         435         445
CCAGCTCCTTCTGCCCCACCCCACCATCTTCAGTGCTGCTTCCTCCTCAAGGCCACAGCTGTAGTTGGCCAGGGGG
                                                              PvuII    BalI
                                                                             BglI
         460         470         480         490         500         510         520
GCTTCATTATTTTTGCTCCCTGGGCAGTAGGAGGAAGAGAATGAATGTCTCTCCATGGGTCTCTTTCTTAGGAATGT
                                                       NcoI
         535         545         555         565         575         585         595
GGGAACTTTTTCCAGAAGTCTCTATGTCTTTTAGTTTGTGTTGGGTCACTGCCCTTCCTGAACCACTTCCTGAC
         610         620         630         640         650         660         670
TCCTGGACAGGATGTGCACTGATGAGCTTAGCTTTGGGGATCTAATAGTGACTTTACAAAGCCTCTTTGAGAAGG
    ApaLI     EspI
         685         695         705         715         725         735         745
TGACATTGGAACCAAGGCTTGAGCAGACACAACAAAGATTGCAGGAGGGCATTGCAGGTGGAGGAAACGGCAC
                                                                         BspMI-
         760         770         780         790         800         810         820
ATGCAAGAGCCCTGCGTGGGAGTGAGCTTGGTGTGTTGGTTGGTCAATCAGTTGTCAGAGCACACCGGGCCCTGTCAGCA
                                                                    ApaI
                                                                    EcoO

Fig. 1A-1
```

```
                835              845              855              865              875              885              895
GGCACAGCCTGGGCCTGCTCTGAGTATGACAGAGAGCCCCTGGGAAGTTGTAGGTGGAGGAAAGACAGGTCATGA
       910              920              930              940              950              960      970
CTAGGAAAAAAGCAATCCCTCTGTGTGGGTGGAAGGTTGCAGTGTGTGAGAGAGACAAGACAGAC
   985              995             1005             1015             1025             1035             1045
AGACAGACACTTCTCAATGTTTACAAGTGCTTCAGGCCCTGACCCGAATGCTTCCAAATTTACGTAGTTCTGAAA
                                                              EcoO              BsmI+        SnaBI
  1060             1070             1080             1090             1100             1110             1120
ACCCCCTGTATCATTTCACTACTCAAAGAAACCTCGGGAGTGTTTTCTTCTGAAAGGTCATCAGTTTTGACTC
       1135             1145             1155             1165             1175             1185             1195
TCTGCTGTCTCATTTCTTCTTGCTGGTGGTGATGGTTGCTGTTGTCCCAGGCCCTGTCCCGCATCCTCTTGCCC
  1210             1220             1230             1240             1250             1260             1270
CTGCAGAGGGATGAGTGTTGGGGCCTCACGAGTTGAGTTGTTCATAAGCAGATCTCTTTGAGCAGGCGCCT
PstI             EcoO                                              BglII                          NarI  Ps
       1285             1295             1305             1315             1325             1335             1345
GCAGTGGCCTTGTGTGAGGCTGGAGGGGTTTCGATTCCCTTATGGAATCCAGGCAGATGTAGCATTAAACAACA
tI                                                                                     DraI
  1360             1370             1380             1390             1400             1410             1420
CACGTGTATAAAAGAAACCAGTGTCCGCAGAAGGTTCCAGAAAGTATTATGGGATAAGACTACATGAGAGAGAA
       1435             1445             1455             1465             1475             1485             1495
TGGGGCATTGGCACCTCCCTTAGTAGGGCCTTTGCTGGGGTAGAAATGAGTTTTAAGGCAGGTTAGACCCCTCGA
                                              EcoO                                              BspMI-
  1510             1520             1530             1540             1550             1560             1570
ACTGGCTTTTGAATCGGGAAATTTACCCCCCAGCCGTTCTGTGCTTCATTGCTCTGTTCACATCACTGCCTAAGATG
       1585             1595             1605             1615             1625             1635             1645
GAGGAACTTTGATGTGTGTGTGTTCTTCCTCACTGGCTCTGCTTCTTCACTTCCTTGTCAATGCAGAGAA
  1660             1670             1680             1690             1700             1710             1720
CAGCAGCAGGCACCAGAGGCAGGCCTTGTAAGAAGCACGAGCTGTATGTCAGCTTCCGAGACCTGGGCTGGCAGG
             StuI                                                                                              BspMI
       1735             1745             1755             1765             1775             1785             1795
TAAGGGGCTGGCTGGGTCTGTCTTGGGTGTGGGCCCTCGGCTCCCACAGGCAGCGGGGTGCTGTGCTCA
                        ApaI
                        EcoO         Fig. 1A-2
```

Fig. 1A-3

```
        1810      1820      1830      1840      1850      1860      1870
GTCTTGTTCTCATCTCTGCGGATCTGCCAGTTAAGACTCCAGTATCAAGTGGCCTCGCTAGGAAGGGTACTTGGCTAAGGA
         1885      1895      1905      1915      1925      1935      1945
TACAGGG......(APPROX. 1000 BASES).........GGGAGCCAGCATGGGTGATGCCATTATGA
        1960      1970      1980      1990      2000      2010      2020
GTTATTAGCCTCTCTGGCAGGTGGGCAAACCGAGGCATGGAGGTTTGTTAAGGTGAACTGCCAGTGTGTGACCA
        BglI  BspMI-                                                  Dr
                                                                      PfI
         2035      2045      2055      2065      2075      2085      2095
CCTAGTGGGTAGAGCTGATGATTGCCTCACACCGGAGCTCCTTCCGTGCCGCGTTCTGTCCAGAAGACACAGC
aIII                              SacI                                N
MI
         2110      2120      2130      2140      2150      2160      2170
CATGGATGTCCATTTTAGAGATCAGCAGCCAAGCCCCGTCTCTGTCCTTCATTTTATTTTATGTTTTTTAGAAATGGG
coI
         2185      2195      2205      2215      2225      2235      2245
GTCTTGCTCTGTCACCCAGGCTGGGTGCAGTGGTGTGATCATAGCTCACCGCAGCTTGACGCCGTCTTCCCACT
                                                                Tth111I
         2260      2270      2280      2290      2300      2310      2320
CAGTCTACTAAGCTTGGACTATAGGCCAAGACTATAGAGTGGTCCTTCCATTCTTTTGGACCATGAGAGG
         HindIII                                              BstXI
         2335      2345      2355      2365      2375      2385      2395
GTCTTGCTCTGTCTGCTGCCCCTGCTGCTCAGAAGGCATGGTCTGAGGCTTTCACCTTGGTCGTGAG
         ApaI
         EcoO
         2410      2420      2430      2440      2450      2460      2470
CCTTCGTGGTGGTTTCTTTCAGCATGGGTTGGGATGCTGTGCTCAGGCTTCTGCATGGTTCCCACACTCTCTT
         2485      2495      2505      2515      2525      2535      2545
CTCCTCCTCAGACTGGATCATCGCGCCTGAAGGCTACGCCGCCTACTACTGTGAGGGGAGTGTGCCTCCCTC
                                               BssHII
         2560      2570      2580      2590      2600      2610      2620
TGAACTCCTACATGAACGCCACCACCGCCATCGTGCAGACGCCCATCGTGGGTGTCACGCCATCTTGGGGTGTGG
MstII                                                                Bs
         2635      2645      2655      2665      2675      2685      2695
TCACCTGGGCCGGGCAGGCTGCGGGGCCACCAGATCCCTGCCTCCAAGCTGGGCCTGAGTAGAGATGTCAGCCC
tEII     BglI                                            EcoO
```

```
         2710       2720       2730       2740       2750       2760       2770
ATTGCCATGTCATGACTTTTGGGGCCCCTTGCCGCCGTTAAAAAAATCAAAAATTGTACTTTATGACTGGTTT
                             ApaI
                             EcoO
      2785       2795       2805       2815       2825       2835       2845
GGTATAAAGAGGAGTATAATCTTCGACCCTGGAGTTCATTTATTCTCCTAATTTTTAAAGTAACTAAAAGTTGT
                                                       DraI
   2860       2870       2880       2890       2900       2910       2920
ATGGGCTCCTTTGAGGATGCTTGTAGTATTGTGGGTGCTGGTTACGGTGCCTAAGAGCACTGGGCCCCTGCTTCA
                                                                  ApaI
                                                                  EcoO
       2935       2945       2955       2965       2975       2985       2995
TTTTCCAGTAGAGGAAACAGGTAAACAGATGAGAAATTTCAGTGAGGGCACAGTGATCAGAAGCCGGGCCAGCAG
           3010       3020       3030       3040       3050       3060       3070
GATAATGGGATGGAGAGATGAGTGGGGACCCATGGCCATTCAAGTTAAATTCAGTCGGTCACCAGGAAGAT
                         EcoO NcoI                                   BstEII
        3085       3095       3105       3115       3125       3135       3145
TCCATGTGATAATGAGATTAACGTGCCCAGTCACGGCGACACTCAGTAGGTGTTATTCCTGCTCTGCCAACAGCA
         3160       3170       3180       3190       3200       3210       3220
ACCATAGTTGATAAGAGCTGTTAGGGATTTTGTCCTTTTGCTTAGAATCCAAGGTTCAAGGACCTTGGTTATGTA
                                                                     EcoO
     3235       3245       3255       3265       3275       3285       3295
GCTCCCCTGTCATGAACATCATCGAGCCTTTCCTGCCTACTGATCATCCACCCTGCCTTGAATGCTTCTAGTGAC
                                                                      BsmI+
        3310       3320       3330       3340       3350       3360       3370
AGAGAGCTCACTACCAGGACTACTCCCTCCTTCATTTAGTAATCTGCCCTCCTCTTTCTTTGTCCCTGTCCTGT
    SacI
       3385       3395       3405       3415       3425       3435       3445
GTGTTAAGTCCTGGAGAAAATCTCATCTATCCCTTTCATTTGATTCTCGCTCTTGAGGGCAGGGGTTTTGTTT
          3460       3470       3480       3490       3500       3510       3520
CTTTGTTTGTTTTTTAAGTGTTGGTTTTCCAAAGCCCTTGCTCCCCTGCCCCTCAATTGAAACTTCAAAGCCCTCAT
        3535       3545       3555       3565       3575       3585       3595
TGGGATTGAAGGTCCTTAGGCTGGAAACAGAAGAGTCCTCCCCAACCTGTCCCTGGCCTGTCCCTGGATGTGTGCTG
  EcoOMstII
```

Fig. 1A-4

```
      3610      3620      3630      3640      3650      3660      3670
TGCCAGTATCCCCTGGAAGGTGCCAGGCATGTCTCCCCGGCTGCCAGGGACACATCTCTATCCTTCTCCAACCC
   BglI    3685      3695      3705      3715      3725      3735      3745
CTGCCTTCATGGCCCATGGAACAGGAGTGCCATGCCCTGTGTGCACCTACTTCCATCAGTATTCACCAGAGAT
              NcoI          3770      3780      ApaLI  3790      3800      3810      BglI  3820
CTGCAGGATCAAAGTGAATTCTCCAGGGATTGTGAAATGATGCGATTGTGGTCATGTTAAAAGGGGCAACTGT
 I            EcoRI
PstI
      3835      3845      3855      3865      3875      3885      3895
CTTCTAGAGAGTCCTGATGAAATGCTTCCAGAGGAAATGAGCTGATGGCTGGAATTTGCTTTAAAATCATTCAAG
      XbaI                                                            DraI
      3910      3920      3930      3940      3950      3960      3970
GTGGAGCAGGTGGGGAAGGTATGATGGATGTGTAAGAGTTTGAAATTGTCCATCATAAAATGTGTAAAAAGCATGCT
 BspMI-                                                                       SphI
      3985      3995      4005      4015      4025      4035      4045
GGCCTATGTCAGCAGTCACAGCCTGGAGTGGTAACAGAGTGCCAGTCACTGATGCTCAAGCCTGCCACCTACAG
      4060      4070      4080      4090      4100      4110      4120
TTGCTGGAAACCCAGAAGTTTCACGTTGAAAACAACAGGAGAATCTCTGCCCTGTCTTGAACACGTGGC
      4135      4145      4155      4165      4175      4185      4195
AGATCTGCTAACACTGATCTTGGTTGCCCGTCAGCTTGAGTTGAGTGGCGGTCTTCCCTTAGTTTGCTTAGT
 BglII
      4210      4220      4230      4240      4250      4260      4270
CCCCGCTATTCCCTATGTGTCTTACCTCGGTCTCTATTTGCTCTTATCAGTGGACCTCACGAGGCACTCATAGGCATTT
      4285      4295      4305      4315      4325      4335      4345
GAGTCTATGTGTCCCGTCCCACATCCCTGTAAGGTGCAGAGAAGTCCATGAGCAAGATGGAGCACTTCTAGTG
      4360      4370      4380      4390      4400      4410      4420
GGTCCAAGTCAGGGACACTATTCAGCAATCTACAGTGCACAGGCAGTTCCCCAACAGAGAATTACCTGTCCTG
      4435      4445      4455      4465      4475      4485      4495
AATGTCGGATCTGGCCCCTTCCTTCCCCACTGTATAATGTGAAAACCCTCTATGCTTTGTTCCCCTTGTCTGCAAA
      4510      4520      4530      4540      4550      4560      4570
ACAGGGATAATCCCAGAACTGAGTTGTCCATGTAAAGTGCTTAGAACAGGAGTGCTTGGCTTGGGGAGTGTCAC
                                                                             Bs
```

Fig. 1A-5

```
           4585        4595        4605        4615        4625        4635        4645
CTGCAGTCAGTCATTCATTATGCCCAGACAGGATGTTTCTTTATAGAAACGTGGAGGCCAGTTAGAAACGACTCACCGCT
pMI+
PstI
           4660        4670        4680        4690        4700        4710        4720
TCTCACCACTGCCCATGTTTGGTGTGTTCAGGTCCACTTCATCAACCCGGAAACGGTGCCCAAGCCCCTGCT
           Pf1MI
           4735        4745        4755        4765        4775        4785        4795
GTGCGGCCCACGCAGCTCAATGCCATCTCCGTCCTCCTACTTCGATGACAGCTCCAACGTCATCCTGAAGAAATACA
           4810        4820        4830        4840
GAAACATGGTCCGGGCCTGTGGCTGCCACTAGCTCCTCCGA
```

Fig. 1A-6

```
CONSENSUS PROBE   20          30          40          50          60          70
GATCCTAATGGGCTGTACGTGGACTTCCAGCGCGACGTGGGCTGGACGACTGGATCATCGCCCCGTCG
**                ** ***  ********          ****************
TGTAAGAAGCACGAGCTGTATGTCAGCTTCCGAGACCTGGGCTGGCAGGACTGGATCATCGGCCTGAAG
OP4     28          38          48          58          68          78          88

80          90         100         110         120         130         140
ACTTCGACGCGCTACTACTGCTCCGGAGCCTGCCAGTTCCCCTCTGCGGATCACTTCAACAGCACCAACCA
** ***       ********        ** *****       ** ***  ********
GCTACGCGCGCTACTACTGTGAGGGGAGTGTGCCTTCCCCTCTGAACTCCTACATGAACGCCACCAACCA
          98         108         118         128         138         148         158

150         160         170         180         190         200         210
CGCCGTGTGGTGCAGAGACCCTGGTGAACAACATGAACCCCGGCAAGGTACCAAGCCCTGCTGCCCACC
****       ******   *** ***  ** *****       ** ***   ********
CGCCATCGTGCAGAGACGCTGGTCCACTTCATCAACCCGGAAACGGTGCCCAAGCCCTGTGCGCCACG
         168         178         188         198         208         218         228

220         230         240         250         260         270         280
GAGCTGTCCGCCATCAGCATGCTGTACCTGGACGAGAATTCCACCGTGGTGCTGAAGAACTACCAGGAGA
****       ** ***  ** ***  ** ***   **** ***  ********
CAGCTCAATGCCATCTCCGTCCTCACTTCGATGACAGCTCCAACGTCATCCTGAAGAATACAGAAACA
         238         248         258         268         278         288         298

290         300         310
TGACCGTGGTGGGCTGCGGCTGCCGCTAACTGCA
****       ** ***   ********  *** **
TGGTGGTCCGGGCCTGTGGCTGCCACTAGCTCCT
         308         318         328
```

Fig. 1B

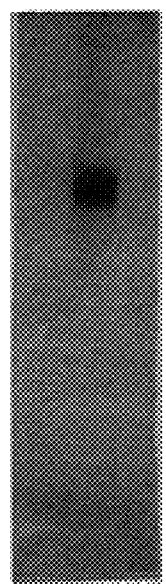 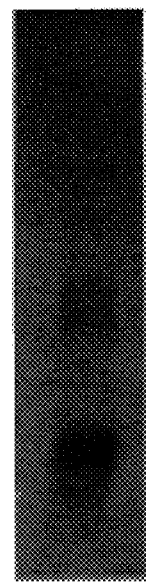
Fig. 3A  Fig. 3B
 
Fig. 4A  Fig. 4B

```
          10          20         30         40         50
GATCCTAATGGGCTGTACGTGGACTTCCAGCGCGACGTGGGCTGGGACGA
 D   P   N   G   L   Y   V   D   F   Q   R   D   V   G   W   D   D 60          70         80         90        100
CTGGATCATCGCCCCCGTCGACTTCGACGCCTACTACTGCTCCGGAGCCT
   W   I   I   A   P   V   D   F   D   A   Y   Y   C   S   G   A 110         120        130        140        150
GCCAGTTCCCCTCTGCGGATCAATTCAACAGCACCAACCACGCCGTGGTG
 C   Q   F   P   S   A   D   H   F   N   S   T   N   H   A   V   V 160         170        180        190        200
CAGACCCTGGTGAACAACATGAACCCCGGCAAGGTACCCAAGCCCTGCTG
 Q   T   L   V   N   N   M   N   P   G   K   V   P   K   P   C   C 210         220        230        240        250
CGTGCCCACCGAGCTGTCCGCCATCAGCATGCTGTACCTGGACGAGAATT
   V   P   T   E   L   S   A   I   S   M   L   Y   L   D   E   N 260         270        280        290        300
CCACCGTGGTGCTGAAGAACTACCAGGAGATGACCGTGGTGGGCTGCGGC
 S   T   V   V   L   K   N   Y   Q   E   M   T   V   V   G   C   G

310
TGCCGCTAACTGCAG
 C   R   *
```

Fig. 13

| COP1 | COP3 | COP4 | COP5 | COP7 | ::VG1 | DPP | OP1 | CBMP2 a) | CBMP2 b) | CBMP3 :(bov) | beta-Inhibin a) | beta-Inhibin b) | TGF-beta 1 | TGF-beta 2 | TGF-beta 3 | MIS | alpha-Inhib | :: | consensus choices |
|---|---|---|---|---|---|---|---|---|---|---|---|---|---|---|---|---|---|---|---|
| < | < | < | P | P | :: | | | | | | | | | | | | | :: | c |
| P | N | G | P | N | :: | | | | | R | | | | | | | | :: | k,r |
| N | N | N | N | N | :: | | | | S | | | | | | | | | :: | k,r |
| G | G | G | G | G> | :: | | | | | | | | | | | | | :: | h,k,r,q |
| L | L | L | L | L | :: | | | | | | | | | | | | | :: | p,s,e,q |
| Y | Y | Y | Y | Y | :: | | | | | | | | | | | | | :: | l |
| V | V | V | V | V | :: | | | | | | | | | | | | | :: | y,f |
| D | D | D | D | D | :: | | | | | | | | | | | | | :: | v,i |
| F | F | F | F | F | :: | | | | | | | | | | | | | :: | d,e,s |
| Q | R | S | S | S | :: | | | | | | | | | | | | | :: | f |
| R | R | | | | :: | | | | | | | | | | | | | :: | k,r,s |
| C | C | C | C | C | :: | C | C | C | C | C | C | C | C | V | C | C | C | :: | c |
| K | K | K | K | K | :: | R | K | K | R | A | C | C | V | V | V | A | H | :: | |
| R | R | R | R | R | :: | R | H | H | H | R | R | C | L | L | L | L | R | :: | |
| H | R | H | H | H | :: | H | S | E | P | Y | Q | K | V | V | V | R | V | :: | |
| L | L | L | L | L | :: | L | L | L | L | L | F | F | R | P | P | E | A | :: | |
| Y | Y | Y | Y | Y | :: | Y | Y | Y | Y | Y | F | F | Q | Q | Q | L | L | :: | |
| V | V | V | V | V | :: | V | V | V | V | V | V | V | L | L | L | S | N | :: | |
| D | D | D | D | D | :: | D | E | S | D | D | S | S | Y | Y | Y | V | I | :: | |
| F | F | F | F | F | :: | F | F | F | F | F | D | D | H | H | H | D | S | :: | d |
| Q | R | Q | S | S | :: | S | R | S | A | A | F | F | D | D | D | L | F | :: | v,l,i |
| R | R | R | R | R | :: | | | | | | F | F | F | F | F | R | Q | :: | g |
| D | D | D | D | D | :: | D | D | D | D | D | K | K | K | K | K | A | | :: | w |
| V | L | V | V | V | :: | V | L | V | V | I | D | D | R | R | R | E | E | :: | q,n,d,e,s |
| G | G | G | G | G | :: | G | G | G | G | G | I | I | Q | Q | Q | R | L | :: | d,e,n |
| W | W | W | W | W | :: | W | W | W | W | W | G | G | L | L | L | S | G | :: | |
| N | Q | N | D | D | :: | N | Q | N | N | S | W | W | G | G | G | | W | :: | w |
| D | D | D | D | D | :: | D | D | D | D | E | N | N | W | W | W | | E | :: | i,v |
| W | W | W | W | W | :: | W | W | W | W | W | D | D | K | K | K | V | I | :: | i,v |
| I | I | I | I | I | :: | I | I | I | I | I | W | W | I | I | I | L | V | :: | a,s |
| I | I | I | I | I | :: | I | I | V | V | V | I | I | V | V | H | I | Y | :: | p |
| A | A | A | A | A | :: | A | A | A | A | A | I | I | A | A | E | P | P | :: | e,q,p* |
| P | P | P | P | P | :: | P | P | P | P | P | A | A | P | P | P | E | P | :: | g,s |
| E | E | Q | Q | P | :: | L | E | K | T | K | P | P | K | K | K | T | S | :: | y,f |
| G | G | G | G | G | :: | G | G | G | G | G | T | T | G | G | G | Y | F | :: | h,d,n,q,y* |
| Y | Y | Y | Y | Y | :: | Y | Y | Y | Y | Y | G | G | Y | Y | Y | Q | I | :: | a |
| D | Q | Q | H | M | :: | D | A | H | H | D | Y | Y | H | H | H | A | F | :: | |
| A | A | A | A | A | :: | A | A | A | A | A | G | G | A | A | A | A | A | :: | |

COP-5 fusion protein

```
          10         20         30         40         50
ATGAAAGCAATTTTCGTACTGAAAGGTTCACTGGACAGAGATCTGGACTC
 M  K  A  I  F  V  L  K  G  S  L  D  R  D  L  D  S
                                           BglII 60         70         80         90        100
TCGTCTGGATCTGGACGTTCGTACCGACCACAAAGACCTGTCTGATCACC
 R  L  D  L  D  V  R  T  D  H  K  D  L  S  D  H 110        120        130        140        150
TGGTTCTGGTCGACCTGGCTCGTAACGACCTGGCTCGTATCGTTACTCCC
 L  V  L  V  D  L  A  R  N  D  L  A  R  I  V  T  P
          SalI                                    Sma 160        170        180        190        200
GGGTCTCGTTACGTTGCGGATCTGGAATTCATGGCTGACAACAAATTCAA
  G  S  R  Y  V  A  D  L  E  F  M  A  D  N  K  F  N
 I              EcoRI 210        220        230        240        250
CAAGGAACAGCAGAACGCGTTCTACGAGATCTTGCACCTGCCGAACCTGA
  K  E  Q  Q  N  A  F  Y  E  I  L  H  L  P  N  L
           MluI           BglII       BspMI+

260        270        280        290        300
ACGAAGAGCAGCGTAACGGCTTCATCCAAAGCTTGAAGGATGAGCCCTCT
 N  E  E  Q  R  N  G  F  I  Q  S  L  K  D  E  P  S
                                HindIII 310        320        330        340        350
CAGTCTGCGAATCTGCTAGCGGATGCCAAGAAACTGAACGATGCGCAGGC
 Q  S  A  N  L  L  A  D  A  K  K  L  N  D  A  Q  A
            NheI                              FspI 360        370        380        390        400
ACCGAAATCGGATCAGGGGCAATTCATGGCTGACAACAAATTCAACAAGG
 P  K  S  D  Q  G  Q  F  M  A  D  N  K  F  N  K 410        420        430        440        450
AACAGCAGAACGCGTTCTACGAGATCTTGCACCTGCCGAACCTGAACGAA
 E  Q  Q  N  A  F  Y  E  I  L  H  L  P  N  L  N  E
         MluI          BglII       BspMI+

460        470        480        490        500
GAGCAGCGTAACGGCTTCATCCAAAGCTTGAAGGATGAGCCCTCTCAGTC
 E  Q  R  N  G  F  I  Q  S  L  K  D  E  P  S  Q  S
                                HindIII
```

Fig. 21B-1

```
          510        520        530        540        550
TGCGAATCTGCTAGCGGATGCCAAGAAACTGAACGATGCGCAGGCACCGA
  A  N  L  L  A  D  A  K  K  L  N  D  A  Q  A  P
        NheI                              FspI 560        570        580        590        600
AGGATCCTAATGGGCTGTACGTCGACTTCAGCGACGTGGGCTGGGACGAC
 K  D  P  N  G  L  Y  V  D  F  S  D  V  G  W  D  D
  BamHI              SalI 610        620        630        640        650
TGGATTGTGGCCCCACCAGGCTACCAGGCCTTCTACTGCCATGGCGAATG
  W  I  V  A  P  P  G  Y  Q  A  F  Y  C  H  G  E  C
                     StuI           NcoI      BsmI+

660        670        680        690        700
CCCTTTCCCGCTAGCGGATCACTTCAACAGCACCAACCACGCCGTGGTGC
  P  F  P  L  A  D  H  F  N  S  T  N  H  A  V  V
           NheI                          DraIII
                                         PflMI 710        720        730        740        750
AGACCCTGGTGAACTCTGTCAACTCCAAGATCCCTAAGGCTTGCTGCGTG
 Q  T  L  V  N  S  V  N  S  K  I  P  K  A  C  C  V
                                 MSTII 760        770        780        790        800
CCCACCGAGCTGTCCGCCATCAGCATGCTGTACCTGGACGAGAATGAGAA
  P  T  E  L  S  A  I  S  M  L  Y  L  D  E  N  E  K
                          SphI 810        820        830        840        850
GGTGGTGCTGAAGAACTACCAGGAGATGGTAGTAGAGGGCTGCGGCTGCC
  V  V  L  K  N  Y  Q  E  M  V  V  E  G  C  G  C
                             PflMI

860
GCTAACTGCAG
 R  *
      PstI
```

Fig. 21B-2

OSTEOGENIC DEVICES

CROSS REFERENCE TO RELATED APPLICATION

This application is a continuation of U.S. Ser. No. 08/417,071, filed Apr. 4, 1995, now U.S. Pat. No. 5,814,604, which is a continuation of U.S. Ser. No. 08/145,812, filed Nov. 1, 1993, now U.S. Pat. No. 5,750,651; which is a divisional of U.S. Ser. No. 07/995,345, filed Dec. 22, 1992, now U.S. Pat. No. 5,258,494; which is a divisional of U.S. Ser. No. 07/315,342, filed Feb. 23, 1989, now U.S. Pat. No. 5,011,691; which is a continuation-in-part of U.S. Ser. No. 07/232,630, filed Aug. 15, 1988, now abandoned; which is a continuation-in-part of U.S. Ser. No. 07/179,406, filed Apr. 8, 1988, now U.S. Pat. No. 4,968,590.

BACKGROUND OF THE INVENTION

This invention relates to osteogenic devices, to genes encoding proteins which can induce osteogenesis in mammals and methods for their production using recombinant DNA techniques, to synthetic forms of osteogenic protein, to a method of reproducibly purifying osteogenic protein from mammalian bone, to matrix materials which act as a carrier to induce osteogenesis in mammals, and to bone and cartilage repair procedures using the osteogenic device.

Mammalian bone tissue is known to contain one or more proteinaceous materials, presumably active during growth and natural bone healing, which can induce a developmental cascade of cellular events resulting in endochondral bone formation. This active factor (or factors) has variously been referred to in the literature as bone morphogenetic or morphogenic protein, bone inductive protein, osteogenic protein, osteogenin, or osteoinductive protein.

The developmental cascade of bone differentiation consists of chemotaxis of mesenchymal cells, proliferation of progenitor cells, differentiation of cartilage, vascular invasion, bone formation, remodeling, and finally marrow differentiation (Reddi (1981) Collagen Rel. Res. 1:209–226).

Though the precise mechanisms underlying these phenotypic transformations are unclear, it has been shown that the natural endochondral bone differentiation activity of bone matrix can be dissociatively extracted and reconstituted with inactive residual collagenous matrix to restore full bone induction activity (Sampath and Reddi, (1981) Proc. Natl. Acad. Sci. USA 78:7599–7603). This provides an experimental method for assaying protein extracts for their ability to induce endochondral bone in vivo.

This putative bone inductive protein has been shown to have a molecular mass of less than 50 kilodaltons (kD). Several species of mammals produce closely related protein as demonstrated by cross species implant experiments (Sampath and Reddi (1983) Proc. Natl. Acad. Sci. USA 80:6591–6595).

The potential utility of these proteins has been widely recognized. It is contemplated that the availability of the pure protein would revolutionize orthopedic medicine, certain types of plastic surgery, and various periodontal and craniofacial reconstructive procedures.

The observed properties of these protein fractions have induced an intense research effort in various laboratories directed to isolating and identifying the pure factor or factors responsible for osteogenic activity. The current state of the art of purification of osteogenic protein from mammalian bone is disclosed by Sampath et al. (Proc. Natl. Acad. Sci. USA (1987) 80). Urist et al. (Proc. Soc. Exp. Biol. Med. (1984) 173:194–199) disclose a human osteogenic protein fraction which was extracted from demineralized cortical bone by means of a calcium chloride-urea inorganic-organic solvent mixture, and retrieved by differential precipitation in guanidine-hydrochloride and preparative gel electrophoresis. The authors report that the protein fraction has an amino acid composition of an acidic polypeptide and a molecular weight in a range of 17–18 kD.

Urist et al. (Proc. Natl. Acad. Sci. USA (1984) 81:371–375) disclose a bovine bone morphogenetic protein extract having the properties of an acidic polypeptide and a molecular weight of approximately 18 kD. The authors reported that the protein was present in a fraction separated by hydroxyapatite chromatography, and that it induced bone formation in mouse hindquarter muscle and bone regeneration in trephine defects in rat and dog skulls. Their method of obtaining the extract from bone results in ill-defined and impure preparations.

European Patent Application Serial No. 148,155, published Oct. 7, 1985, purports to disclose osteogenic proteins derived from bovine, porcine, and human origin. One of the proteins, designated by the inventors as a P3 protein having a molecular weight of 22–24 kD, is said to have been purified to an essentially homogeneous state. This material is reported to induce bone formation when implanted into animals.

International Application No. PCT/087/01537, published Jan. 14, 1988, discloses an impure fraction from bovine bone which has bone induction qualities. The named applicants also disclose putative bone inductive factors produced by recombinant DNA techniques. Four DNA sequences were retrieved from human or bovine genomic or cDNA libraries and apparently expressed in recombinant host cells. While the applicants stated that the expressed proteins may be bone morphogenic proteins, bone induction was not demonstrated, suggesting that the recombinant proteins are not osteogenic. See also Urist et al., EP 0,212,474 entitled Bone Morphogenic Agents.

Wang et al. (Proc. Nat. Acad. Sci. USA (1988) 85: 9484–9488) discloses the purification of a bovine bone morphogenetic protein from guanidine extracts of demineralized bone having cartilage and bone formation activity as a basic protein corresponding to a molecular weight of 30 kD determined from gel elution. Purification of the protein yielded proteins of 30, 18 and 16 kD which, upon separation, were inactive. In view of this result, the authors acknowledged that the exact identity of the active material had not been determined.

Wozney et al. (Science (1988) 242: 1528–1534) discloses the isolation of full-length cDNA's encoding the human equivalents of three polypeptides originally purified from bovine bone. The authors report that each of the three recombinantly expressed human proteins are independently or in combination capable of inducing cartilage formation. No evidence of bone formation is reported.

It is an object of this invention to provide osteogenic devices comprising matrices containing dispersed osteogenic protein capable of bone induction in allogenic and xenogenic implants. Another object is to provide a reproducible method of isolating osteogenic protein from mammalian bone tissue. Another object is to characterize the protein responsible for osteogenesis. Another object is to provide natural and recombinant osteogenic proteins capable of inducing endochondral bone formation in mammals, including humans. Yet another object is to provide genes encoding native and non-native osteogenic proteins and methods for their production using recombinant DNA techniques. Another object is to provide novel biosynthetic forms of osteogenic proteins and a structural design for novel, functional osteogenic proteins. Another object is to provide a suitable deglycosylated collagenous bone matrix as a carrier for osteogenic protein for use in xenogenic implants. Another object is to provide methods for inducing cartilage formation.

These and other objects and features of the invention will be apparent from the description, drawings, and claims which follow.

SUMMARY OF THE INVENTION

This invention involves osteogenic devices which, when implanted in a mammalian body, can induce at the locus of the implant the full developmental cascade of endochondral bone formation and bone marrow differentiation. Suitably modified as disclosed herein, the devices also may be used to induce cartilage formation. The devices comprise a carrier material, referred to herein as a matrix, having the characteristics disclosed below, containing dispersed osteogenic protein either in its native form or in the form of a biosynthetic construct.

A key to these developments was the elucidation of amino acid sequence and structure data of native osteogenic protein. A protocol was developed which results in retrieval of active, substantially pure osteogenic protein from mammalian bone. Investigation of the properties and structure of the native form osteogenic protein then permitted the inventors to develop a rational design for non-native forms, i.e., forms never before known in nature, capable of inducing bone formation. As far as applicants are aware, the constructs disclosed herein constitute the first instance of the design of a functional, active protein without preexisting knowledge of the active region of a native form nucleotide or amino acid sequence.

A series of consensus DNA sequences were designed with the goal of producing an active osteogenic protein. The sequences were based on partial amino acid sequence data obtained from the natural source product and on observed homologies with unrelated genes reported in the literature, or the sequences they encode, having a presumed or demonstrated developmental function. Several of the biosynthetic consensus sequences have been expressed as fusion proteins in procaryotes, purified, cleaved, refolded, combined with a matrix, implanted in an established animal model, and shown to have endochondral bone-inducing activity. The currently preferred active totally biosynthetic proteins comprise two synthetic sequences designated COP5 and COP7. The amino acid sequences of these proteins are set forth below.

```
        1         10        20        30        40
COP5        LYVDFS-DVGWDDWIVAPPGYQAFYCHGECPFPLAD
                      50        60        70
            HFNSTN--H-AVVQTLVNSVNSKI--PKACCVPTELSA
                  80        90        100
            ISMLYLDENEKVVLKNYQEMVVEGCGCR 1         10        20        30        40
COP7        LYVDFS-DVGWNDWIVAPPGYAHFYCHGECPFPLAD
                      50        60        70
            HLNSTN--H-AVVQTLVNSVNSKI--PKACCVPTELSA
                  80        90        100
            ISMLYLDENEKVVLKNYQEMVVEGCGCR
```

In these sequences and all other amino acid sequences disclosed herein, the dashes (-) are used as fillers only to line up comparable sequences in related proteins, and have no other function. Thus, amino acids 45–50 of COP7, for example, are NHAVV. Also, the numbering of amino acids is selected solely for purposes of facilitating comparisons between sequences. Thus, for example, the DF residues numbered at 9 and 10 of COP5 and COP7 may comprise residues, e.g., 35 and 36, of an osteogenic protein embodying invention.

Thus, in one aspect, the invention comprises a protein comprising an amino acid sequence sufficiently duplicative of the sequence of COP5 or COP7 such that it is capable of inducing endochondral bone formation when properly folded and implanted in a mammal in association with a matrix. Some of these sequences induce cartilage, but not bone. Also, the bone forming materials may be used to produce cartilage if implanted in an avascular locus, or if an inhibitor to full bone development is implanted together with the active protein. Thus, in another aspect, the invention comprises a protein less than about 200 amino acids long in a sequence sufficiently duplicative of the sequence of COP5 or COP7 such that it is capable at least of cartilage formation when properly folded and implanted in a mammal in association with a matrix.

In one preferred aspect, these proteins comprise species of the generic amino acid sequences:

```
    1         10        20        30        40        50
        LXVXFXDXGWXXWXXXPXGXXAXYCXGXCXXPXXXXXXXXNHAAK
              60        70        80        90        100
    QXXVXXXNXXXXPXXCCXPXXXXXXXXLXXXXXXVXXLXXYXXMXVXXCXCX or 1         10        20        30        40        50
    CXXXXLXVXFXDXGWXXWXXXPXGXXAXYCXGXCXXPXXXXXXXXNHAXX
              60        70        80        90        100
    QXXVXXXNXXXXPXXCCXPXXXXXXXXLXXXXXXVXLXXYXXMXVXXCXCX
``` where the letters indicate the amino acid residues of standard single letter code, and the Xs represent amino acid residues. Preferred amino acid sequences within the foregoing generic sequences are:

```
1        10        20        30        40        50
    LYVDFRDVGWNDWIVAPPGYHAFYCHGECPFPLADHLNSTNHAIV
      K S S L   QE VIS E FD Y   E A AY MPESMKAS    VI
      F E K I   DN     L   N S  Q   ITK F P        TL
              A       S           K
            60        70        80        90       100
QTLVNSVNPGKIPKACCVPTELSAISMLYLDENENVVLKNYQDMVVEGCGCR
  SI HAI SEQV EP  A  EQMNSLAI FFNDQDK  I  RK EE  T DA H H
     RF      T   S       K DPV V  Y N S     H  RN    RS
         N       S                     K        P     E
``` and

```
1        10        20        30        40        50
CKRHPLYVDFRDVGWNDWIVAPPGYHAFYCHGECPFPLADHLNSTNHAIV
 RRRS K S S L   QE VIS E FD Y   E A AY MPESMKAS    VI
   KE F E K I   DN     L   N S  Q   ITK F P        TL
    Q       A       S           K
            60        70        80        90       100
QTLVNSVNPGKIPKACCVPTELSAISMLYLDENENVVLKNYQDMVVEGCGCR
  SI HAI SEQV EP  A  EQMNSLAI FFNDQDK  I  RK EE  T DA H H
     RF      T   S       K DPV V  Y N S     H  RN    RS
         N       S                     K        P     E
``` wherein each of the amino acids arranged vertically at each position in the sequence may be used alternatively in various combinations. Note that these generic sequences have 6 and preferably 7 cysteine residues where inter- or intramolecular disulfide bonds can form, and contain other critical amino acids which influence the tertiary structure of the proteins. These generic structural features are found in previously published sequences, none of which have been described as capable of osteogenic activity, and most of which never have been linked with such activity.

Particular useful sequences include:

```
           1        10        20        30        40
Vg1        CKKRHLYVEFK-DVGWQNWVIAPQGYMANYCYGECPYPLTE
                     50        60        70
           ILNGSN--H-AILQTLVHSIEPED-IPLPCCVPTKMSP
                     80        90       100
           ISMLFYDNNDNVVLRHYENMAVDECGCR 1        10        20        30        40
DPP        CRRHSLYVDFS-DVGWDDWIVAPLGYDAYYCHGKCPFPLAD
                     50        60        70
           HFNSTN--H-AVVQTLVNNNNPGK-VPKACCVPTQLDS
                     80        90       100
           VAMLYLNDQSTVVLKNYQEMTVVGCGCR
                                              -5
                                             HQRQA
           1        10        20        30        40
OP 1       CKKHELYVSFR-DLGWQDWIIAPEGYAAYYCEGECAFPLNS
                     50        60        70
           YMNATN--H-AIVQTLVHFINPET-VPKPCCAPTQLNA
                     80        90       100
           ISVLYFDDSSNVILKKYRNMVVRACGCH 1        10        20        30        40
CBMP-2a    CKRHPLYVDFS-DVGWNDWIVAPPGYHAFYCHGECPFPLAD
                     50        60        70
           HLNSTN--H-AIVQTLVNSVNS-K-IPKACCVPTELSA
                     80        90       100
           ISMLYLDENEKVVLKNYQDMVVEGCGCR 1        10        20        30        40
CBMP-2b    CRRHSLYVDFS-DVGWNDWIVAPPGYQAFYCHGDCPFPLAD
                     50        60        70
           HLNSTN--H-AIVQTLVNSVNS-S-IPKACCVPTELSA
                     80        90       100
           ISMLYLDEYDKVVLKNYQEMVVEGCGCR 1        10        20        30        40
CBMP-3     CARRYLKVDFA-DIGWSEWIISPKSFDAYYCSGACQFPMPK
                     50        60        70
           SLKPSN--H-ATIQSIVRAVGVVPGIPEPCCVPEKMSS
                     80        90       100
           LSILFFDENKNVVLKVYPNMTVESCACR 1        10        20        30        40
COP 1      LYVDFQRDVGWDDWIIAPVDFDAYYCSGACQFPSAD
                     50        60        70
           HFNSTN--H-AVVQTLVNNMNPGK-VPKPCCVPTELSA
                     80        90       100
           ISMLYLDENSTVVLKNYQEMTVVGCGCR 1        10        20        30        40
COP3       LYVDFQRDVGWDDWIVAPPGYQAFYCSGACQFPSAD
                     50        60        70
           HFNSTN--H-AVVQTLVNNMNPGK-VPKPCCVPTELSA
                     80        90       100
           ISMLYLDENEKVVLKNYQEMVVEGCGCR 1        10        20        30        40
COP4       LYVDFS-DVGWDDWIVAPPGYQAFYCSGACQFPSAD
                     50        60        70
           HFNSTN--H-AVVQTLVNNMNPGK-VPKPCCVPTELSA
                     80        90       100
           ISMLYLDENEKVVLKNYQEMVVEGCGCR
                                              -10
                                             PKHHSQRARKKNKN
           1        10        20        30        40
COP16      CRRHSLYVDFS-DVGWNDWIVAPPGYQAFYCHGECPFPLAD
                     50        60        70
           HFNSTN--H-AVVQTLVNSVNSKI--PKACCVPTELSA
                     80        90       100
           ISMLYLDENEKVVLKNYQEMVVEGCGCR
```

Vg1 is a known Xenopus sequence heretofore not associated with bone formation. DPP is an amino acid sequence encoded by a drosophila gene responsible for development of the dorsoventral pattern. OP1 is a region of a natural sequence encoded by exons of a genomic DNA sequence retrieved by applicants. The CBMPs are amino acid sequences comprising subparts of mammalian proteins encoded by genomic DNAs and cDNAs retrieved by applicants. The COPs are biosynthetic protein sequences expressed by novel consensus gene constructs, designed using the criteria set forth herein, and not yet found in nature.

These proteins are believed to dimerize during refolding. They appear not to be active when reduced. Various combinations of species of the proteins, i.e., heterodimers, have activity, as do homodimers. As far as applicants are aware, the COP5 and COP7 constructs constitute the first instances of the design of a bioactive protein without preexisting knowledge of the active region of a native form nucleotide or amino acid sequence.

The invention also provides native forms of osteogenic protein, extracted from bone or produced using recombinant DNA techniques. The substantially pure osteogenic protein may include forms having varying glycosylation patterns, varying N-termini, a family of related proteins having regions of amino acid sequence homology, and active truncated or mutated forms of native protein, no matter how derived. The osteogenic protein in its native form is glycosylated and has an apparent molecular weight of about 30 kD as determined by SDS-PAGE. When reduced, the 30 kD protein gives rise to two glycosylated polypeptide chains having apparent molecular weights of about 16 kD and 18 kD. In the reduced state, the 30 kD protein has no detectable osteogenic activity. The deglycosylated protein, which has osteogenic activity, has an apparent molecular weight of about 27 kD. When reduced, the 27 kD protein gives rise to the two deglycosylated polypeptides have molecular weights of about 14 kD to 16 kD.

Analysis of digestion fragments indicate that the native 30 kD osteogenic protein contains the following amino acid sequences (question marks indicate undetermined residues):
(1) S-F-D-A-Y-Y-C-S-G-A-C-Q-F-P-M-P-K;
(2) S-L-K-P-S-N-Y-A-T-I-Q-S-I-V;
(3) A-C-C-V-P-T-E-L-S-A-I-S-M-L-Y-L-D-E-N-E-K;
(4) M-S-S-L-S-I-L-F-F-D-E-N-K;
(5) S-Q-E-L-Y-V-D-F-Q-R;
(6) F-L-H-C-Q-F-S-E-R-N-S;
(7) T-V-G-Q-L-N-E-Q-S-S-E-P-N-I-Y;
(8) L-Y-D-P-M-V-V;
(9) V-G-V-V-P-G-I-P-E-P-C-C-V-P-E;
(10) V-D-F-A-D-I-G;
(11) V-P-K-P-C-C-A-P-T;
(12) I-N-I-A-N-Y-L;
(13) D-N-H-V-L-T-M-F-P-I-A-I-N;
(14) D-E-Q-T-L-K-K-A-R-R-K-Q-W-I-?-P;
(15) D-I-G-?-S-E-W-I-I-?-P;
(16) S-I-V-R-A-V-G-V-P-G-I-P-E-P-?-?-V;
(17) D-?-I-V-A-P-P-Q-Y-H-A-F-Y;
(18) D-E-N-K-N-V-V-L-K-V-Y-P-N-M-T-V-E;
(19) S-Q-T-L-Q-F-D-E-Q-T-L-K-?-A-R-?-K-Q;
(20) D-E-Q-T-L-K-X-A-R-R-K-Q-W-I-E-P-R-N-?-A-R-R-Y-L;
(21) A-R-R-K-Q-W-I-E-P-R-N-?-A-?-R-Y-?-?-V-D; and
(22) R-?-Q-W-I-E-P-?-N-?-A-?-?-Y-L-K-V-D-?-A-?-?-G.

The substantially pure (i.e., free of contaminating proteins having no osteoinductive activity) osteogenic proteins and the synthetics are useful in clinical applications in conjunction with a suitable delivery or support system (matrix). The matrix is made up of particles or porous materials. The pores must be of a dimension to permit progenitor cell migration and subsequent differentiation and proliferation. The particle size should be within the range of 70–850 mm, preferably 70–420 mm. It may be fabricated by close packing particulate material into a shape spanning the bone defect, or by otherwise structuring as desired a material that is biocompatible (non-inflammatory) and, biodegradable in vivo to serve as a "temporary scaffold" and substratum for recruitment of migratory progenitor cells, and as a base for their subsequent anchoring and proliferation. Currently preferred carriers include particulate, demineralized, guanidine extracted, species-specific (allogenic) bone, and particulate, deglycosglated, protein extracted, demineralized, xenogenic bone. Optionally, such xenogenic bone powder matrices also may be treated with proteases such as trypsin. Other useful matrix materials comprise collagen, homopolymers and copolymers of glycolic acid and lactic acid, hydroxyapatite, tricalcium phosphate and other calcium phosphates.

The availability of the protein in substantially pure form, and knowledge of its amino acid sequence and other structural features, enable the identification, cloning, and expression of native genes which encode osteogenic proteins. When properly modified after translation, incorporated in a suitable matrix, and implanted as disclosed herein, these proteins are operative to induce formation of cartilage and endochondral bone.

The consensus DNA sequences are also useful as probes for extracting genes encoding osteogenic protein from genomic and cDNA libraries. One of the consensus sequences has been used to isolate a heretofore unidentified genomic DNA sequence, portions of which when ligated encode a protein having a region capable of inducing endochondral bone formation. This protein, designated OP1, has an active region having the sequence set forth below.

```
           1        10        20        30        40
    OP1    LYVSFR-DLGWQDWIIAPEGYAAYYCEGECAFPLNS
                    50        60        70
           YMNATN--H-AIVQTLVHFINPET-VPKPCCAPTQLNA
                    80        90       100
           ISVLYFDDSSNVILKKYRNMVVRACGCH
```

A longer active sequence is:

```
                                                 -5
                                                HQRQA
           1        10        20        30        40
    OP1    CKKHELYVSFR-DLGWQDWIIAPEGYAAYYCEGECAFPLNS
                    50        60        70
           YMNATN--H-AIVQTLVHFINPET-VPKPCCAPTQLNA
                    80        90       100
           ISVLYFDDSSNVILKKYRNMVVRACGCH
```

FIG. 1A discloses the genomic DNA sequence of OP1.

The probes have also retrieved the DNA sequences identified in PCT/087/01537, referenced above, designated therein as BMPII(b) and BMPIII. The inventors herein have discovered that certain subparts of these genomic DNAs, and BMPIIa, from the same publication, when properly assembled, encode proteins (CBMPIIa, CBMPIIb, and CBMPIII) which have true osteogenic activity, i.e., induce the full cascade of events when properly implanted in a mammal leading to endochondral bone formation.

Thus, in view of this disclosure, skilled genetic engineers can design and synthesize genes or isolate genes from cDNA or genomic libraries which encode appropriate amino acid sequences, and then can express them in various types of host cells, including both procaryotes and eucaryotes, to produce large quantities of active proteins in native forms, truncated analogs, muteins, fusion proteins, and other constructs capable of inducing bone formation in mammals including humans.

The osteogenic proteins and implantable osteogenic devices enabled and disclosed herein will permit the physician to obtain optimal predictable bone formation to correct, for example, acquired and congenital craniofacial and other skeletal or dental anomalies (Glowacki et al. (1981) Lancet 1:959–963). The devices may be used to induce local endochondral bone formation in non-union fractures as demonstrated in animal tests, and in other clinical applications including periodontal applications where bone formation is required. The other potential clinical application is in cartilage repair, for example, in the treatment of osteoarthritis.

BRIEF DESCRIPTION OF THE DRAWING

The foregoing and other objects of this invention, the various features thereof, as well as the invention itself, may be more fully understood from the following description, when read together with the accompanying drawings, in which:

FIGS. 1A-1 to 1A-6 represent the nucleotide sequence of the genomic copy of osteogenic protein "OP1" gene. The unknown region between 1880 and 1920 actually represents about 1000 nucleotides;

FIG. 1B is a representation of the hybridization of the consensus gene/probe to the osteogenic protein "OP1" gene;

FIG. 3 is a photographic reproduction of a Coomassie blue stained SDS polyacrylamide gel of the osteogenic protein under non-reducing (A) and reducing (B) conditions;

FIG. 4 is a photographic reproduction of a Con A blot of an SDS polyacrylamide gel showing the carbohydrate component of oxidized (A) and reduced (B) 30 kD protein;

FIG. 5 is a photographic reproduction of an autoradiogram of an SDS polyacrylamide gel of $^{125}$I-labelled glycosylated (A) and deglycosylated (B) osteogenic protein under non-reducing (1) and reducing (2) conditions;

FIG. 6 is a photographic reproduction of an autoradiogram of an SDS polyacrylamide gel of peptides produced upon the digestion of the 30 kD osteogenic protein with V-8 protease (B), Endo Lys C protease (C), pepsin (D), and trypsin (E). (A) is control;

FIG. 13 is a schematic representation of the DNA sequence and corresponding amino acid sequence of a consensus gene/probe for osteogenic protein (COP0);

FIG. 18 is a comparison of the amino acid sequence of various osteogenic proteins to those of the TGF-beta family. COP1, COP3, COP4, COP5, and COP7 are a family of analogs of synthetic osteogenic proteins developed from the consensus gene that was joined to a leader protein via a hinge region having the sequence D-P-N-G that permitted chemical cleavage at the D-P site (by acid) or N-G (by hydroxylamine) resulting in the release of the analog protein; VGI is a Xenopus protein, DPP is a Drosophila protein; OP1 is a native osteogenic protein; CBMP2a and 2b, and CBMP3 are subparts of proteins disclosed in PCT application 087/01537; MIS. is Mullerian inhibitory substance; and "consensus choices" represent various substitutions of amino acids that may be made at various positions in osteogenic proteins;

FIGS. 21B-1 to 21B-2 are the DNA sequence comprising a modified trp-LE leader, two Fb domains of protein A, an ASP-PRO cleavage site, and the COP5 sequence;

DESCRIPTION

Figure 2B:
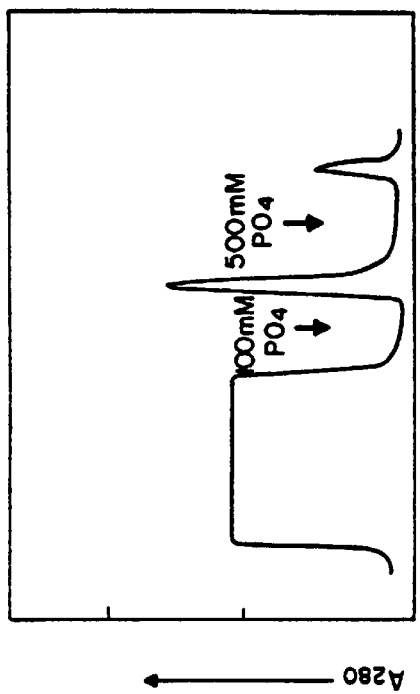
FIGS. 2A–2D are collections of plots of protein concentration (as indicated by optical absorption) vs elution volume illustrating the results of bovine osteogenic protein (BOP) fractionation during purification on heparin-Sepharose-I; HAP-Ultragel; sieving gel (Sephacryl 300); and heparin-Sepharose-II.

Purification protocols have been developed which enable isolation of the osteogenic protein present in crude protein extracts from mammalian bone. While each of the separation steps constitute known separation techniques, it has been discovered that the combination of a sequence of separations exploiting the protein's affinity for heparin and for hydroxyapatite (HAP) in the presence of a denaturant such as urea is key to isolating the pure protein from the crude extract. These critical separation steps are combined with separations on hydrophobic media, gel exclusion chromatography, and elution form SDS PAGE.

The isolation procedure enables the production of significant quantities of substantially pure osteogenic protein from any mammalian species, provided sufficient amounts of fresh bone from the species is available. The empirical development of the procedure, coupled with the availability of fresh calf bone, has enabled isolation of substantially pure bovine osteogenic protein (BOP). BOP has been characterized significantly as set forth below; its ability to induce cartilage and ultimately endochondral bone growth in cat, rabbit, and rat have been studied; it has been shown to be able to induce the full developmental cascade of bone formation previously ascribed to unknown protein or proteins in heterogeneous bone extracts; and it may be used to induce formation of endochondral bone in orthopedic defects including non-union fractures. In its native form it is a glycosylated, dimeric protein. However, it is active in deglycosylated form. It has been partially sequenced. Its primary structure includes the amino acid sequences set forth herein.

Elucidation of the amino acid sequence of BOP enables the construction of pools of nucleic acid probes encoding peptide fragments. Also, a consensus nucleic acid sequence designed as disclosed herein based on the amino acid sequence data, inferred codons for the sequences, and observation of partial homology with known genes, also may be used as a probe. The probes may be used to isolate naturally occuring cDNAs which encode active mammalian osteogenic proteins (OP) as described below using standard hybridization methodology. The mRNAs are present in the cytoplasm of cells of various species which are known to synthesize osteogenic proteins. Useful cells harboring the mRNAs include, for example, osteoblasts from bone or osteosarcoma, hypertrophic chondrocytes, and stem cells. The mRNAs can be used to produce cDNA libraries. Alternatively, relevant DNAs encoding osteogenic protein may be retrieved from cloned genomic DNA libraries from various mammalian species.

The consensus sequence described above also may be refined by comparison with the sequences present in certain regulatory genes from drosophila, xenopus, and human followed by point mutation, expression, and assay for activity. This approach has been successful in producing several active totally synthetic constructs not found in nature (as far as applicants are aware) which have true osteogenic activity.

These discoveries enable the construction of DNAs encoding totally novel, non-native protein constructs which individually, and combined are capable of producing true endochondral bone. They also permit expression of the natural material, truncated forms, muteins, analogs, fusion proteins, and various other variants and constructs, from cDNAs retrieved from natural sources or synthesized using the techniques disclosed herein using automated, commercially available equipment. The DNAs may be expressed using well established recombinant DNA technologies in procaryotic or eucaryotic host cells, and may be oxidized and refolded in vitro if necessary for biological activity.

The isolation procedure for obtaining the protein from bone, the retrieval of an osteogenic protein gene, the design and production of biosynthetics, the nature of the matrix, and other material aspects concerning the nature, utility, how to make, and how to use the subject matter claimed herein will be further understood from the following, which constitutes the best method currently known for practicing the various aspects of the invention.

I. NATURALLY SOURCED OSTEOGENIC PROTEIN

A—Purification

A1. Preparation of Demineralized Bone

Demineralized bovine bone matrix is prepared by previously published procedures (Sampath and Reddi (1983) Proc. Natl. Acad. Sci. USA 80:6591–6595). Bovine diaphyseal bones (age 1–10 days) are obtained from a local slaughterhouse and used fresh. The bones are stripped of muscle and fat, cleaned of periosteum, demarrowed by pressure with cold water, dipped in cold absolute ethanol, and stored at −20° C. They are then dried and fragmented by crushing and pulverized in a large mill. Care is taken to prevent heating by using liquid nitrogen. The pulverized bone is milled to a particle size between 70–420 mm and is defatted by two washes of approximately two hours duration with three volumes of chloroform and methanol (3:1). The particulate bone is then washed with one volume of absolute ethanol and dried over one volume of anhydrous ether. The defatted bone powder (the alternative method is to obtain Bovine Cortical Bone Powder (75–425mm) from American Biomaterials) is then demineralized with 10 volumes of 0.5 N HCl at 4° C. for 40 min., four times. Finally, neutralizing washes are done on the demineralized bone powder with a large volume of water.

A2. Dissociative Extraction and Ethanol Precipitation

Demineralized bone matrix thus prepared is dissociatively extracted with 5 volumes of 4 M guanidine-HCl, 50 mM Tris-HCl, pH 7.0, containing protease inhibitors (5 mM benzamidine, 44 mM 6-aminohexanoic acid, 4.3 mM N-ethylmaleimide, 0.44 mM phenylmethylsulfonyfluoride) for 16 hr. at 4° C. The suspension is filtered. The supernatant is collected and concentrated to one volume using an ultrafiltration hollow fiber membrane (Amicon, YM-10). The concentrate is centrifuged (8,000×g for 10 min. at 4° C.), and the supernatant is then subjected to ethanol precipitation. To one volume of concentrate is added five volumes of cold (−70° C.) absolute ethanol (100%), which is then kept at −70° C. for 16 hrs. The precipitate is obtained upon centrifugation at 10,000×g for 10 min. at 4° C. The resulting pellet is resuspended in 4 l of 85% cold ethanol incubated for 60 min. at −70° C. and recentrifuged. The precipitate is again resuspended in 85% cold ethanol (2 l), incubated at −70° C. for 60 min. and centrifuged. The precipitate is then lyophilized.

A3. Heparin-Sepharose Chromatography I

The ethanol precipitated, lyophilized, extracted crude protein is dissolved in 25 volumes of 6 M urea, 50 mM Tris-HCl, pH 7.0 (Buffer A) containing 0.15 M NaCl, and clarified by centrifugation at 8,000×g for 10 min. The heparin-Sepharose is column-equilibrated with Buffer A. The protein is loaded onto the column and after washing with three column volume of initial buffer (Buffer A containing 0.15 M NaCl), protein is eluted with Buffer A containing 0.5 M NaCl. The absorption of the eluate is monitored continuously at 280 nm. The pool of protein eluted by 0.5 M NaCl (approximately 1 column volumes) is collected and stored at 4° C.

Figure 2A:
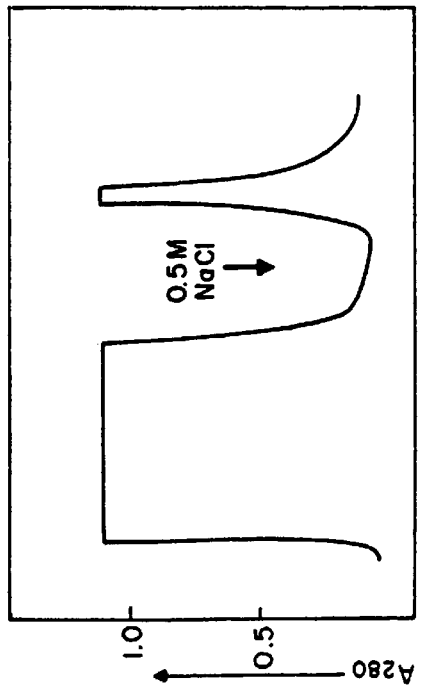

As shown in FIG. 2A, most of the protein (about 95%) remains unbound. Approximately 5% of the protein is bound to the column. The unbound fraction has no bone inductive activity when bioassayed as a whole or after a partial purification through Sepharose CL-6B.

A4. Hydroxyapaptite-Ultrogel Chromatoaraphy

The volume of protein eluted. by Buffer A containing 0.5 M NaCl from the heparin-Sepharose is applied directly to a column of hydroxyapaptite-ultrogel (HAP-ultrogel) (LKB Instruments), equilibrated with Buffer A containing 0.5 M NaCl. The HAP-ultrogel is treated with Buffer A containing 500 mM Na phosphate prior to equilibration. The unadsorbed protein is collected as an unbound fraction, and the column is washed with three column volumes of Buffer A containing 0.5 M NaCl. The column is subsequently eluted with Buffer A containing 100 mM Na Phosphate (FIG. 2B).

The eluted component can induce endochondral bone as measured by alkaline phosphatase activity and histology. As the biologically active protein is bound to HAP in the presence of 6 M urea and 0.5 M NaCl, it is likely that the protein has an affinity for bone mineral and may be displaced only by phosphate ions.

A5. Sephacryl S-300 Gel Exclusion Chromatoaraphy

Figure 2D:
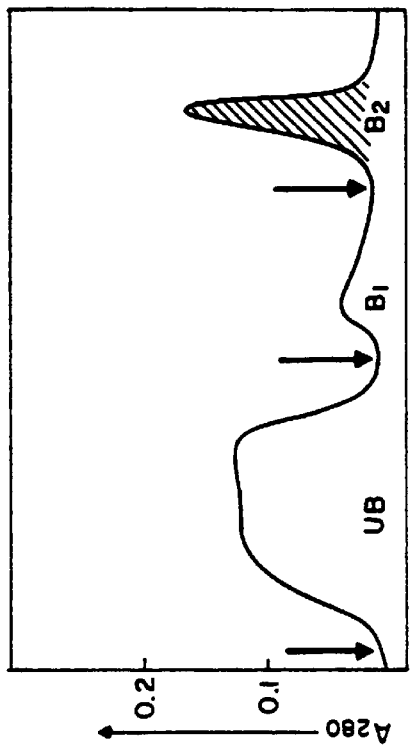
Figure 2C:
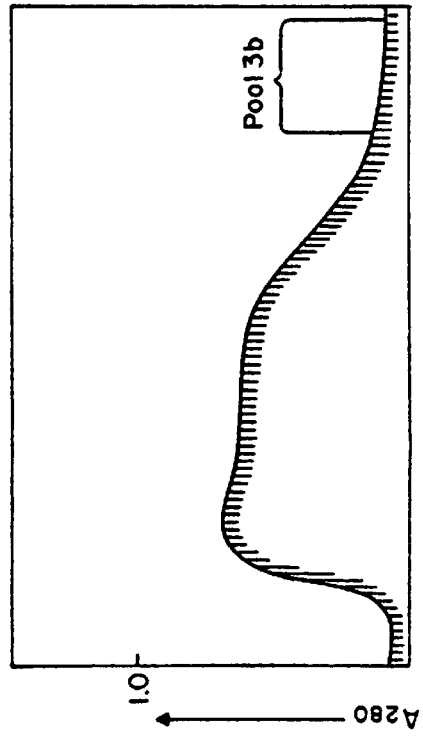

Sephacryl S-300 HR (High Resolution, 5 cm×100 cm column) is obtained from Pharmacia and equilibrated with 4 M guanidine-HCl, 50 mM Tris-HCl, pH 7.0. The bound protein fraction from HA-ultrogel is concentrated and exhanged from urea to 4 M guanidine-HCl, 50 mM Tris-HCl, pH 7.0 via an Amicon ultrafiltration YM-10 membrane. The solution is then filtered with Schleicher and Schuell CENTREX disposable microfilters. A sample aliquot of approximately 15 ml containing approximately 400 mg of protein is loaded onto the column and then eluted with 4 M guanidine-HCl, 50 mM Tris-HCl, pH 7.0, with a flow rate of 3 ml/min; 12 ml fractions are collected over 8 hours and the concentration of protein is measured at $A_{280}$ nm (FIG. 2C). An aliquot of the individual fractions is bioassayed for bone formation. Those fractions which have shown bone formation and have a molecular weigh less than 35 kD are pooled and concentrated via an Amicon ultrafiltration system with YM-10 membrane.

A6. Heparin-Sepharose Chromatography-II

The pooled osteo-inductive fractions obtained from gel exclusion chromatography are dialysed extensively against distilled water and then against 6 M urea, 50 mM Tris-HCl, pH 7.0 (Buffer A) containing 0.1 M NaCl. The dialysate is then cleared through centrifugation. The sample is applied to the heparin-sepharose column (equilibrated with the same buffer). After washing with three column volumes of initial buffer, the column is developed sequentially with Buffer B containing 0.15 M NaCl, and 0.5 M NaCl (FIG. 2D). The protein eluted by 0.5 M NaCl is collected and dialyzed extensively against distilled water. It is then dialyzed against 30% acetonitrile, 0.1% TFA at 4° C.

A7. Reverse Phase HPLC

Figure 8:
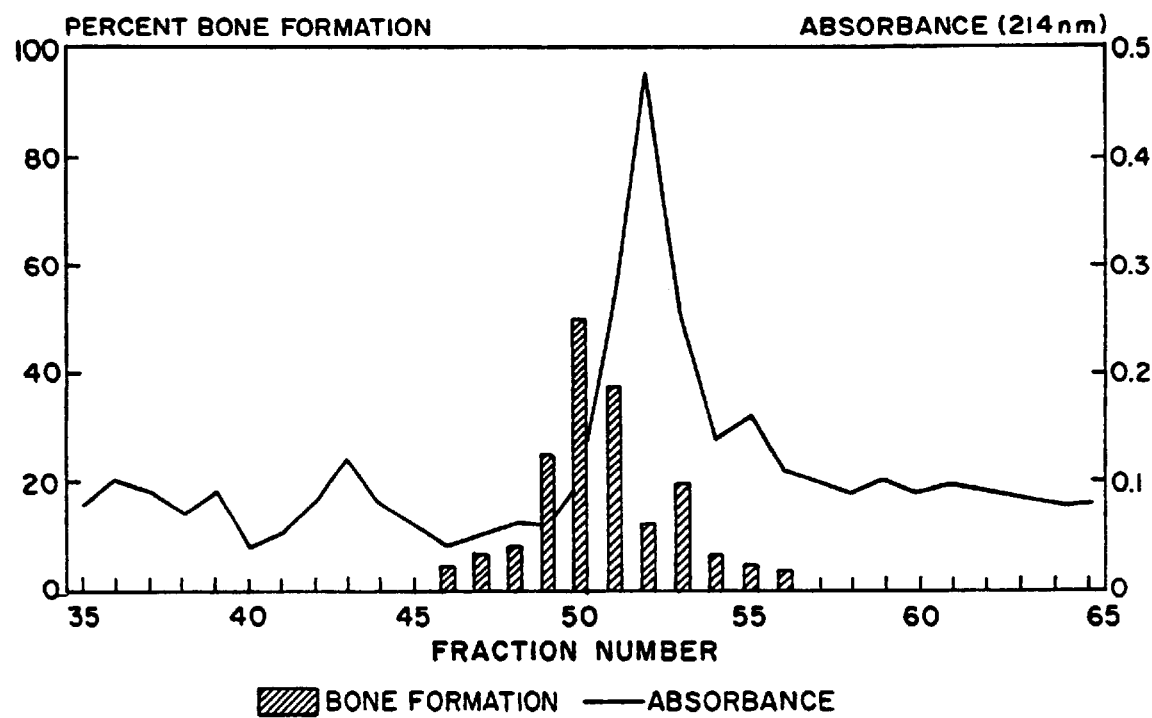
FIG. 8 is an HPLC chromatogram of an elution profile on reverse phase C-18 HPLC of the samples recovered from the second heparin-Sepharose chromatography step (see FIG. 2D). Superimposed is the percent bone formation in each fraction.

The protein is further purified by C-18 Vydac silica-based HPLC column chromatography (particle size 5 mm; pore size 300 A). The osteoinductive fraction obtained from heparin-sepharose-II chromatograph is loaded onto the column, and washed in 0.1% TFA, 10% acetonitrile for five min. As shown in FIG. 8, the bound proteins are eluted with a linear gradient of 10–30% acetonitrile over 15 min., 30–50% acetonitrile over 60 min, and 50–70% acetonitrile over 10 min at 22° C. with a flow rate of 1.5 ml/min and 1.4 ml samples are collected in polycarbonate tubes. Protein is monitored by absorbance at $A_{214}$ nm. Column fractions are tested for the presence of osteoinductive activity, concanavalin A-blottable proteins and then pooled. Pools are then characterized biochemically for the presence of 30 kD protein by autoradiography, concanavalin A blotting, and Coomassie blue dye staining. They are then assayed for in vivo osteogenic activity. Biological activity is not found in the absence of 30 kD protein.

A8. Gel Elution

The glycosylated or deglycosylated protein is eluted from SDS gels (0.5 mm and 1.5 mm thickness) for further characterization. $^{125}$I-labelled 30 kD protein is routinely added to each preparation to monitor yields. TABLE 1 shows the various elution buffers that have been tested and the yields of $^{125}$I-labelled protein.

TABLE 1

Elution of 30 kD Protein from SDS Gel

| Buffer | % Eluted | |
|---|---|---|
| | 0.5 mm | 1.5 mm |
| (1) dH$_2$O | 22 | |
| (2) 4M Guanidine-HCl, Tris-HCl, pH 7.0 | 2 | |
| (3) 4M Guanidine-HCl, Tris-HCl, pH 7.0, 0.5% Triton × 100 | 93 | 52 |
| (4) 0.1% SDS, Tris-HCl, pH 7.0 | 98 | |

TABLE 2 lists the steps used to isolate the 30 kD or deglycosylated 27 kD gel-bound protein. The standard protocol uses diffusion elution using 4M guanidine-HCl containing 0.5% Triton×100 in Tris-HCl buffer or in Tris-HCl buffer containing 0.1% SDS to achieve greater than 95% elution of the protein from the 27 or 30 kD region of the gel for demonstration of osteogenic activity in vivo as described in later section.

In order to isolate substantially purified 30 kD or deglycosylated 27 kD protein for sequencing and characterization, the following steps are. mentioned in Table 2.

TABLE 2

Preparation of Gel Eluted Protein (C-18 Pool or deglycoslated protein plus $^{125}$I-labelled 30 kD protein)

| | |
|---|---|
| 1. | Dry using vacuum centrifugation; |
| 2. | Wash pellet with H$_2$O; |
| 3. | Dissolve pellet in gel sample buffer (no reducing agent); |
| 4. | Electrophorese on pre-electrophoresed 0.5 mm mini gel; |
| 5. | Cut out 27 or 30 kD protein; |
| 6. | Elute from gel with 0.1% SDS, 50 mM Tris-HCl, pH 7.0; |
| 7. | Filter through Centrex membrane; |
| 8. | Concentrate in Centricon tube (10 kD membrane); |
| 9. | Chromatograph of TSK-3000 gel filtration column; |
| 10. | Concentrate in Centricon tube. |

Chromatography in 0.1% SDS on a TSK-3000 gel filtration column is performed to separate gel impurities, such as soluble acrylamide, from the final product. The overall yield of labelled 30 kD protein from the gel elution protocol is 50–60% of the loaded sample. Most of the loss occurs in the electrophoresis step, due to protein aggregation and/or smearing. In a separate experiment, a sample of gel eluted 30 kD protein is reduced, electrophoresed on an SDS gel, and transferred to an Immobilon membrane. The membrane is stained with Coomassie blue dye, cut into slices, and the slices are counted. Coomassie blue dye stains the 16 kD and 18 kD reduced species of the 30 kD protein almost exclusively. However, the counts showed significant smearing throughout the gel in addition to being concentrated in the 16 kD and 18 kD species. This suggests that the $^{125}$I-label can exhibit anomalous behavior on SDS gels and cannot be used as an accurate marker for cold protein under such circumstances.

The yield is 0.5 to 1.0 mg substantially pure osteogenic protein per kg of bone.

A9. Isolation of the 16 kD and 18 kD Species

Figure 15:
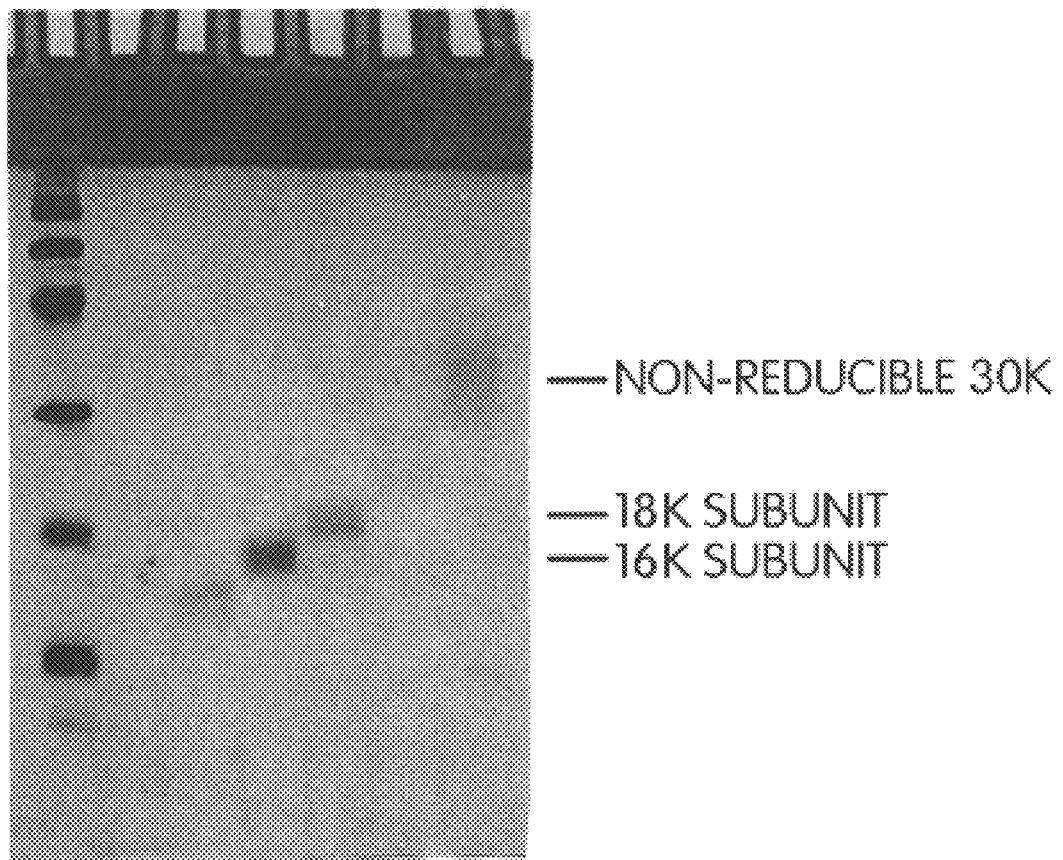
FIG. 15 is a photographic representation of a Coomassie blue stained SDS gel showing gel purified subunits of the 30 kD protein.

TABLE 3 summarizes the procedures involved in the preparation of the subunits. Approximately 10 mg of gel eluted 30 kD protein (FIG. 3) is carboxymethylated and electrophoresed on an SDS-gel. The sample contains $^{125}$I- label to trace yields and to use as an indicator for slicing the 16 kD, 18 kD and non-reduceable 30 K regions from the gel. FIG. 15 shows a Coomassie stained gel of aliquots of the protein isolated from the different gel slices. The slices corresponding to the 16 kD, 18 kD and non-reduceable 30 kD species contained approximately 2–3 mg, 3–4 mg, and 1–2 mg, of protein respectively, as estimated by staining intensity. Prior to SDS electrophoresis, all of the 30 kD species can be reduced to the 16 kD and 18 kD species. The nonreducible 30 kD species observed after electrophoresis appears to be an artifact resulting from the electrophoresis procedure.

TABLE 3

Isolation of the Subunits of the 30 kD protein (C-18 pool plus $^{125}$I labeled 30 kD protein)

| | |
|---|---|
| 1. | Electrophorese on SDS gel. |
| 2. | Cut out 30 kD protein. |
| 3. | Elute with 0.1% SDS, 50 nm Tris, pH 7.0. |
| 4. | Concentrate and wash with H$_2$O in Centricon tube (10 kD membranes). |
| 5. | Reduce and carboxymethylate in 1% SDS, 0.4 M Tris, pH 8.5. |
| 6. | Concentrate and wash with H$_2$O in Centricon tube. |
| 7. | Electrophorese on SDS gel. |
| 8. | Cut out the 16 kD and 18 kD subunits. |
| 9. | Elute with 0.1% SDS, 50 mM Tris, pH 7.0. |
| 10. | Concentrate and wash with H$_2$O in Centricon tubes. |

B. DEMONSTRATION THAT THE 30 KD PROTEIN IS OSTEOGENIC PROTEIN— BIOLOGICAL CHARACTERIZATION

B1. Gel Slicing:

Gel slicing experiments confirm that the isolated 30 kD protein is the protein responsible for osteogenic activity.

Gels from the last step of the purification are sliced. Protein in each fraction is extracted in 15 mM Tris-HCl, pH 7.0 containing 0.1% SDS or in buffer containing 4M guanidine-HCl, 0.5% non-ionic detergent (Tritonx100), 50 mM Tris-HCl. The extracted proteins are desalted, concentrated, and assayed for endochondral bone formation activity. The results are set forth in FIG. 14. From this Figure it is clear that the majority of osteogenic activity is due to protein at 30 kD region of the gene. Activity in higher molecular weight regions is apparently due to protein aggregation. These protein aggregates, when reduced, yields the 16 kD and 18 kD species discussed above.

B2. Con A-Sepharose Chromatography:

A sample containing the 30 kD protein is solubilized using 0.1% SDS, 50 mM Tris-HCl, and is applied to a column of Con A-Sepharose equilibrated with the same buffer. The bound material is eluted in SDS Tris-HCl buffer containing 0.5 M alpha-methyl mannoside. After reverse phase chromatography of both the bound and unbound fractions, Con A-bound materials, when implanted, result in extensive bone formation. Further characterization of the bound materials show a Con A-blottable 30 kD protein. Accordingly, the 30 kD glycosylated protein is responsible for the bone forming activity.

Figure 9:
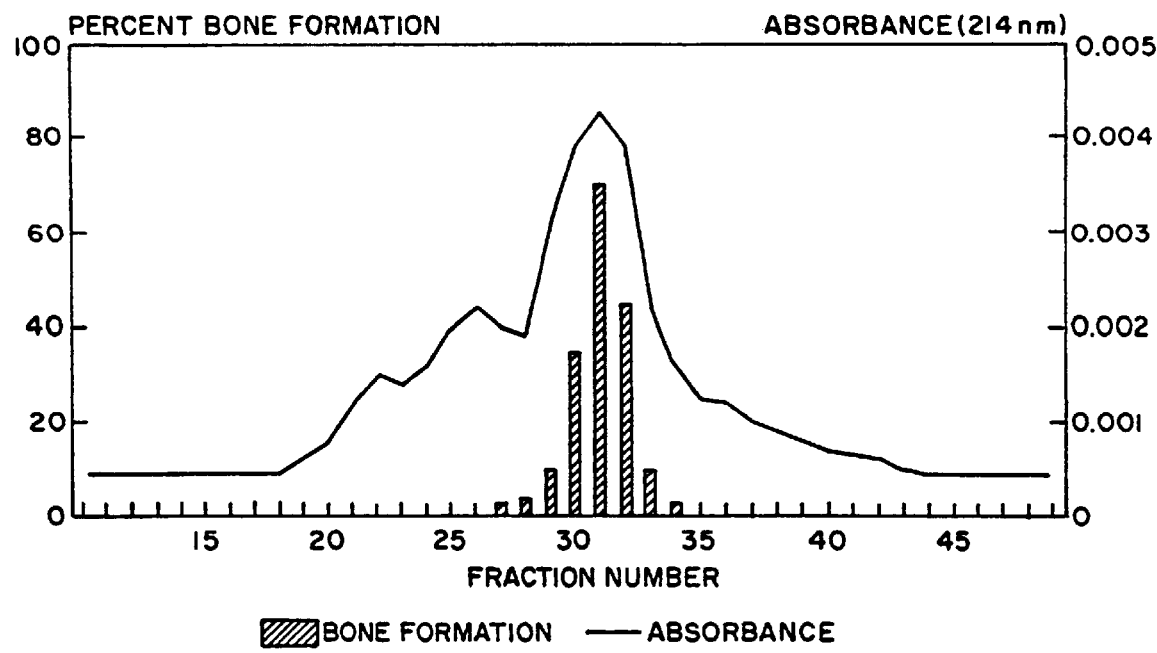
FIG. 9 is a gel permeation chromatogram of an elution profile on TSK 3000/2000 gel of the C-18 purified osteogenic peak fraction. Superimposed is the percent bone formation in each fraction.

B3. Gel Permeation Chromatography:

TSX-3000/2000 gel permeation chromatography in guanidine-HCl alternately is used to achieve separation of the high specific activity fraction obtained from C-18 chromatography (FIG. 9). The results demonstrate that the peak of bone inducing activity elutes in fractions containing substantially pure 30 kD protein by Coomassie blue staining. When this fraction is iodinated and subjected to autoradiography, a strong band at 30 kD accounts for 90% of the iodinated proteins. The fraction induces bone formation in vivo at a dose of 50 to 100 ng per implant.

B4. Structural Requirements for Biological Activity

Although the role of 30 kD osteogenic protein is clearly established for bone induction, through analysis of proteolytic cleavage products we have begun to search for a minimum structure that is necessary for activity in vivo. The results of cleavage experiments demonstrate that pepsin treatment fails to destroy bone inducing capacity, whereas trypsin or CNBr completely abolishes the activity.

An experiment is performed to isolate and identify pepsin digested product responsible for biological activity. Sample used for pepsin digest were 20%–30% pure. The buffer used is 0.1% TFA in water. The enzyme to substrate ratio is 1:10. A control sample is made without enzyme. The digestion mixture is incubated at room temperature for 16 hr. The digested product is then separated in 4 M guanidine-HCl using gel permeation chromatography, and the fractions are prepared for in vivo assay. The results demonstrate that active fractions from gel permeation chromatography of the pepsin digest correspond to molecular weight of 8 kD–10 kD.

Figure 17A:
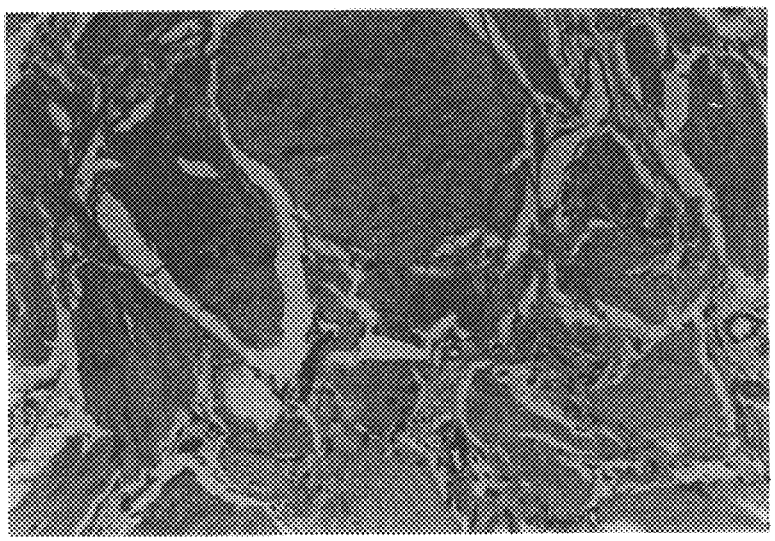
FIG. 17 is a photographic representation of the histological examination of bone implants in the rat model: carrier alone (A); carrier and glycosylated osteogenic protein (B); and carrier and deglycosylated osteogenic protein (C). Arrows indicate osteoblasts.
Figure 17B:
Figure 17C:

In order to understand the importance of the carbohydrates moiety with respect to osteogenic activity, the 30 kD protein has been chemically deglycosylated using HF (see below). After analyzing an aliquot of the reaction product by Con A blot to confirm the absence of carbohydrate, the material is assayed for its activity in vivo. The bioassay is positive (i.e., the deglycosylated protein produces a bone formation response as determined by histological examination shown in FIG. 17C), demonstrating that exposure to HF did not destroy the biological function of the protein. In addition, the specific activity of the deglycosylated protein is approximately the same as that of the native glycosylated protein.

B5. Specific-Activity of BOP

Experiments were performed 1) to determine the half maximal bone-inducing activity based on calcium content of the implant; 2) to estimate proteins at nanogram levels using a gel scanning method; and 3) to establish dose for half maximal bone inducing activity for gel eluted 30 kD BOP. The results demonstrate that gel eluted substantially pure 30 kD osteogenic protein induces bone at less than 5 ng per 25 mg implant and exhibits half maximal bone differentiation activity at 20 ng per implant. The purification data suggest that osteogenic protein has been purified from bovine bone to 367,307 fold after final gel elution step with a specific activity of 47,750 bone forming units per mg of protein.

B5(a) Half Maximal Bone Differentiation Activity

The bone inducing activity is determined biochemically by the specific activity of alkaline phosphatase and calcium content of the day 12 implant. An increase in the specific activity of alkaline phosphatase indicates the onset of bone formation. Calcium content, on the other hand, is proportional to the amount of bone formed in the implant. The bone formation is therefore calculated by determining calcium content of the implant on day 12 in rats and expressed as bone forming units, which represent the amount that exhibits half maximal bone inducing activity compared to rat demineralized bone matrix. Bone induction exhibited by intact demineralized rat bone matrix is considered to be the maximal bone-differentiation activity for comparison.

B5(b) Protein Estimation Using Gel Scanning Techniques

A standard curve is developed employing known amounts of a standard protein, bovine serum albumin. The protein at varying concentration (50–300 ng) is loaded on 15% SDS gel, electrophoresed, stained in comassie and destained. The gel containing standard proteins is scanned at predetermined settings using a gel scanner at 580 nm. The area covered by the protein band is calculated and a standard curve against concentrations of protein is constructed. A sample with an unknown protein concentration is electrophoresed with known concentration of BSA. The lane contained unknown sample is scanned and from the area the concentration of protein is determined.

B5(c) Gel Elution and Specific Activity

Figure 14:
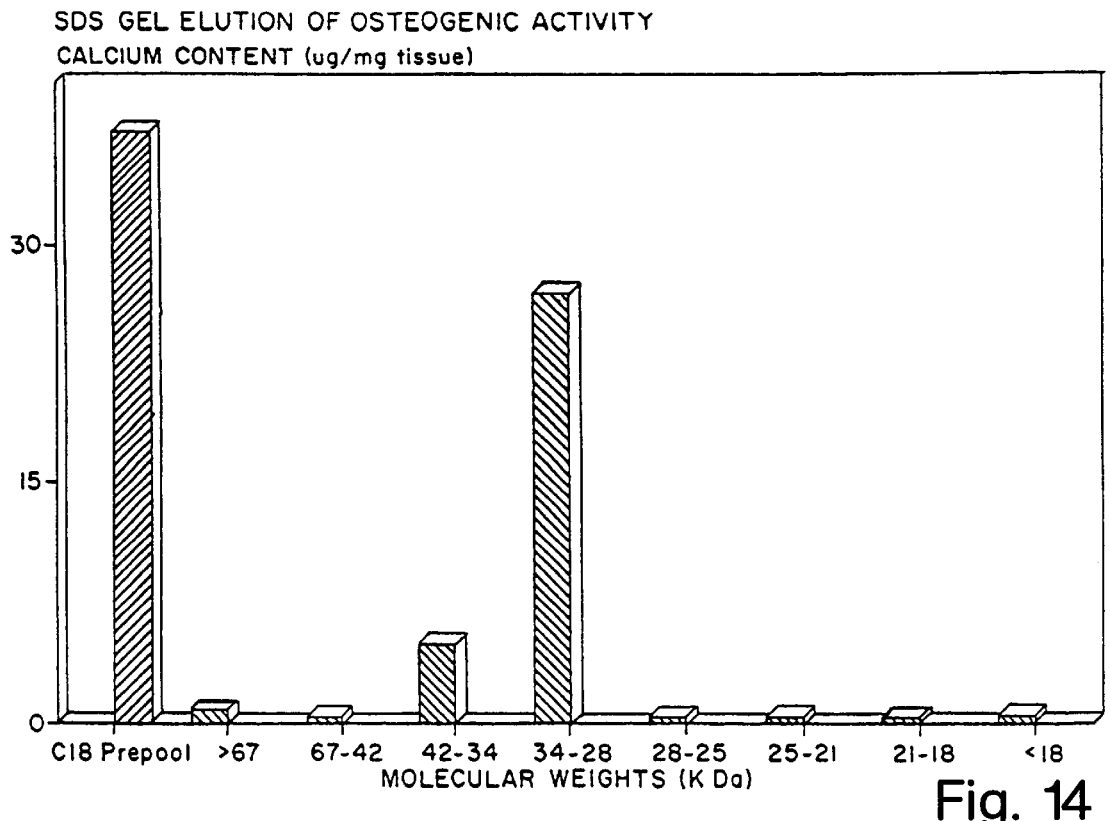
FIG. 14 is a graph of osteogenic activity vs. increasing molecular weight showing peak bone forming activity in the 30 kD region of an SDS polyacrylamide gel.

An aliquot of C-18 highly purified active fraction is subjected to SDS gel and sliced according to molecular weights described in FIG. 14. Proteins are eluted from the slices in 4 M guanidine-HCl containing 0.5% Triton X-100, desalted, concentrated and assayed for endochondral bone forming activity as determined by calcium content. The C-18 highly active fractions and gel eluted substantially pure 30 kD osteogenic protein are implanted in varying concentrations in order to determine the half maximal bone inducing activity.

Figure 20A:
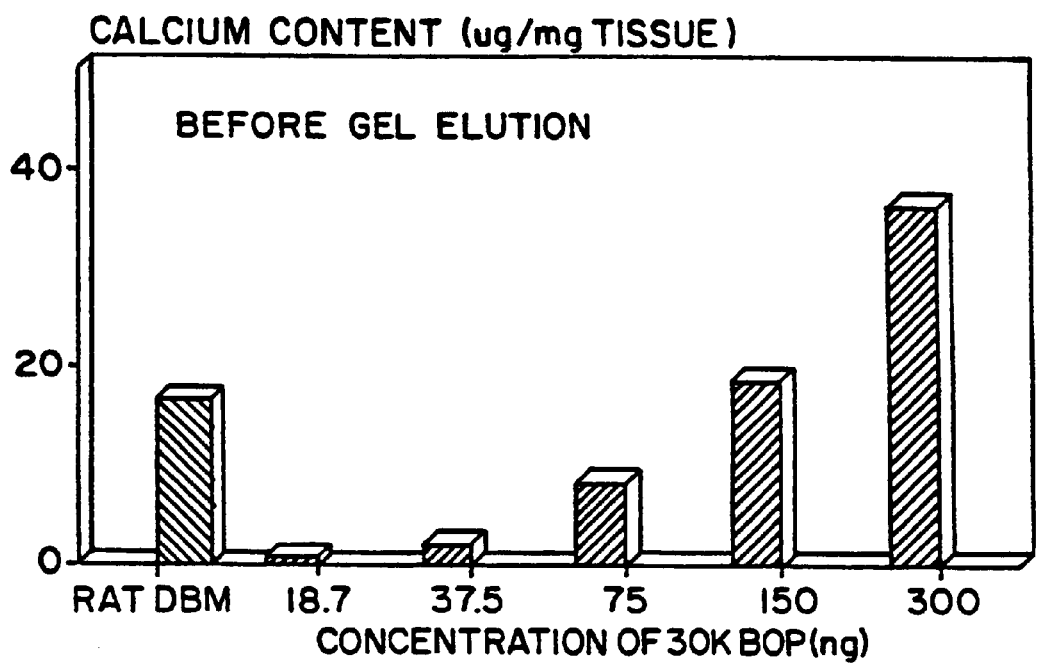
FIGS. 20A and 20B are bar graphs showing the specific activity of naturally sourced OP before and after gel elution as measured by calcium content vs. increasing concentrations of proteins (dose curve, in ng);.
Figure 20B:
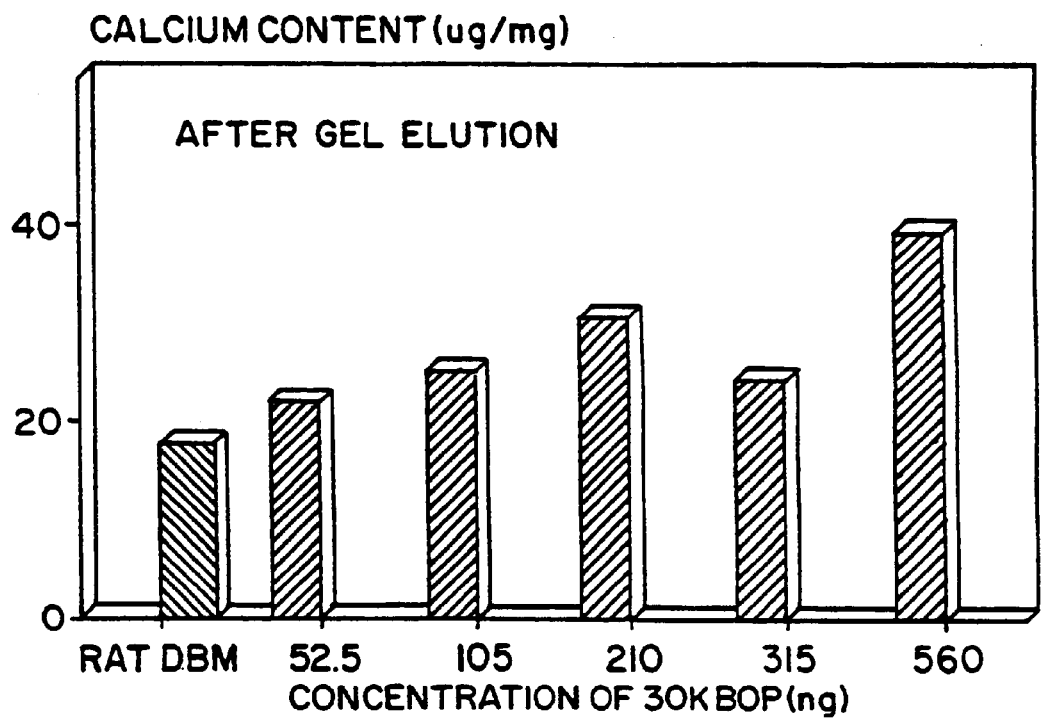

FIG. 14 demonstrates that the bone inducing activity is due to proteins eluted at 28–34 kD region. The recovery of activity after gel elution step is determined by calcium content. FIGS. 20A and 20B represent the bone inducing activity for the various concentrations of 30 kD protein before and after gel elution as estimated by calcium content. The concentration of protein is determined by gel scanning in the 30 kD region. The data suggest that the half maximal activity for 30 kD protein before gel elution is 69 nanogram per 25 mg implant and is 21 nanogram per 25 mg implant after elution. Table 4 describes the yield, total specific activity, and fold purification of osteogenic protein at each step during purification. Approximately 500 ug of heparin sepharose I fraction, 130–150 ug of the HA ultrogel fraction, 10–12 ug of the gel filtration fraction, 4–5 ug of the heparin sepharose II fraction, 0.4–0.5 ug of the C-18 highly purified fraction, and 20–25 ng of gel eluted substantially purified is needed per 25 mg of implant for unequivocal bone formation for half maximal activity. Thus, 0.8–1.0 ng purified osteogenic protein per mg. of implant is required to exhibit half maximal bone differentiation activity in vivo.

TABLE 4

PURIFICATION OF BOP

| Purification Steps | Protein (mg.) | Biological Activity Units* | Specific Activity Units/mg. | Purification Fold |
|---|---|---|---|---|
| Ethanol Precipitate** | 30,000# | 4,000 | 0.13 | 1 |
| Heparin Sepharose I | 1,200# | 2,400 | 2.00 | 15 |
| HA-Ultrogel | 300# | 2,307 | 7.69 | 59 |
| Gel filtration | 20# | 1,600 | 80.00 | 615 |
| Heparin Sepharose II | 5# | 1,000 | 200.00 | 1,538 |
| C-18 HPLC | 0.070@ | 150 | 2,043.00 | 15,715 |
| Gel elution | 0.004@ | 191 | 47,750.00 | 367,307 |

Values are calculated from 4 kg. of bovine bone matrix (800 g of demineralized matrix).

\* One unit of bone forming activity is defined as the amount that exhibits half maximal bone differentiation activity compared to rat demineralized bone matrix, as determined by calcium content of the implant on day 12 in rats.

\# Proteins were measured by absorbance at 280 nm.

@ Proteins were measured by gel scanning method compared to known standard protein, bovine serum albumin.

\*\* Ethanol-precipitated guanidine extract of bovine bone is a weak inducer of bone in rats, possibly due to endogenous inhibitors. This precipitate is. subjected to gel filtration and proteins less than 50 kD were separated and used for bioassay.

C. CHEMICAL CHARACTERIZATION OF BOP

C1. Molecular Weight and Structure

Electrophoresis of the most active fractions from reverse phase C-18 chromatography on non-reducing SDS polyacrylamide gels reveals a single band at about 30 kD as detected by both Coomassie blue staining (FIG. 3A) and autoradiography.

In order to extend the analysis of BOP, the protein was examined under reducing conditions. FIG. 3B shows an SDS gel of BOP in the presence of dithiothreitol. Upon reduction, 30 kD BOP yields two species which are stained with Coomassic blue dye: a 16 kD species and an 18 kD species. Reduction causes loss of biological activity. Methods for the efficient elution of the proteins from SDS gels have been tested, and a protocol has been developed to achieve purification of both proteins. The two reduced BOP species have been analyzed to determine if they are structurally related. Comparison of the amino acid composition of the two proteins (as disclosed below) shows little differences, indicating that the native protein may comprise two chains having some homology.

C2. Charge Determination

Isoelectric focusing studies are initiated to further evaluate the 30 kD protein for possibile heterogeneity. Results to date have not revealed any such heterogeneity. The oxidized and reduced species migrate as diffuse bands in the basic region of the isoelectric focusing gel, using the iodinated 30 kD protein for detection. Using two dimensional gel electrophoresis and Con A for detection, the oxidized 30 kD protein show one species migrating in the same basic region as the iodinated 30 kD protein. The diffuse character of the band may be traced to the presence of carbohydrate attached to the protein.

C3. Presence of Carbohydrate

The 30 kD protein has been tested for the presence of carbohydrate by Concanavalin A (Con A) blotting after SDS-PAGE and transfer to nitrocellulose paper. The results demonstrate that the 30 kD protein has a high affinity for Con A, indicating that the protein is glycosylated (FIG. 4A). In addition, the Con A blots provide evidence for a substructure in the 30 kD region of the gel, suggesting heterogeneity due to varying degrees of glycosylation. After reduction (FIG. 4B), Con A blots show evidence for two major components at 16 kD and 18 kD. In addition, it has been demonstrated that no glycosylated material remains at the 30 kD region after reduction.

Figure 5:
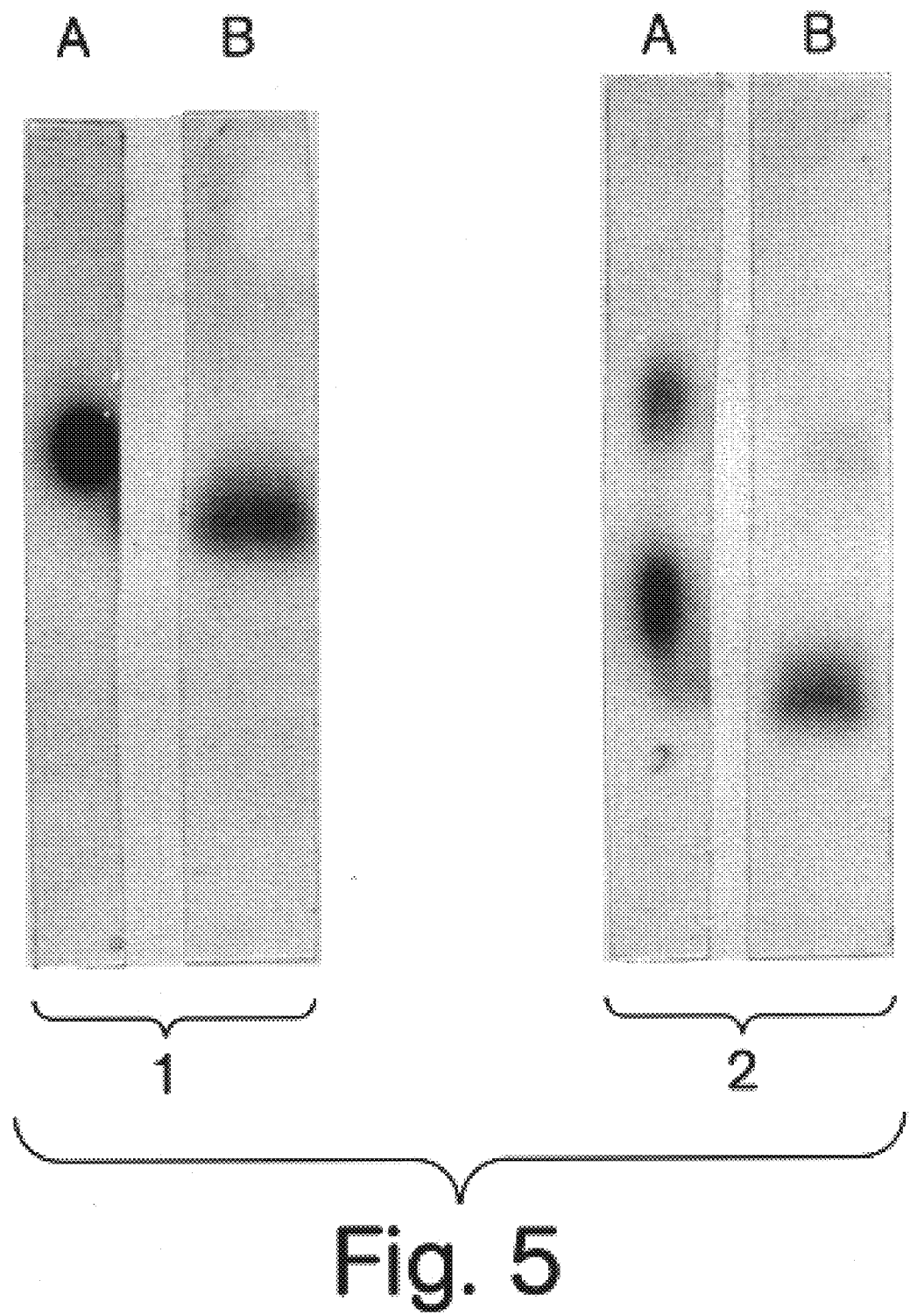
Figure 6A:
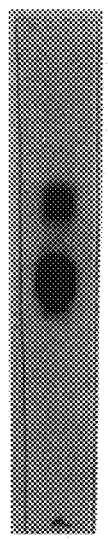
Figure 6B:
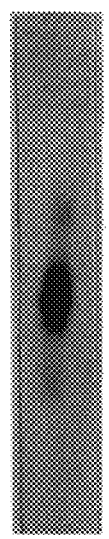
Figure 6C:
Figure 6D:
Figure 6E:
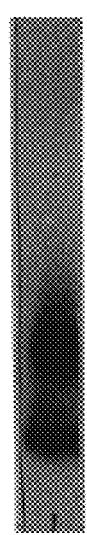

In order to confirm the presence of carbohydrate and to estimate the amount of carbohydrate attached, the 30 kD protein is treated with N-glycanase, a deglycosylating enzyme with a broad specificity. Samples of the $^{125}$I-labelled 30 kD protein are incubated with the enzyme in the presence of SDS for 24 hours at 37° C. As observed by SDS-PAGE, the treated samples appear as a prominent species at about 27 kD (FIG. 5A). Upon reduction, the 27 kD species is reduced to species having a molecular weight of about 14 kD–16 kD (FIG. 5B).

Chemical cleavage of the carbohydrate moieties using hydrogen fluoride (HF) is performed to assess the role of carbohydrate on the bone inducing activity of BOP in vivo. Active osteogenic protein fractions pooled from the C-18 chromatography step are dried in vacuo over $P_2O_5$ in a polypropylene tube, and 50 ml freshly distilled anhydrous HF at −70° C. is added. After capping the tube tightly, the mixture is kept at 0° C. in an ice-bath with occasional agitation for 1 hr. The HF is then evaporated using a continuous stream of dry nitrogen gas. The tube is removed from the ice bath and the residue dried in vacuo over $P_2O_5$ and KOH pellets.

Following drying, the samples are dissolved in 100 ml of 50% acetonitrile/0.1% TFA and aliquoted for SDS gel analysis, Con A binding, and biological assay. Aliquots are dried and dissolved in either SDS gel sample buffer in preparation for SDS gel analysis and Con A blotting or 4 M guanidine-HCl, 50 mM Tris-HCl, pH 7.0 for biological assay.

The results show that samples are completely deglycosylated by the HF treatment: Con A blots after SDS gel electrophoreses and transfer to Immobilon membrane showed no binding of Con A to the treated samples, while untreated controls were strongly positive at 30 kD. Coomassie gels of treated samples showed the presense of a 27 kD band instead of the 30 kD band present in the untreated controls.

C4. Chemical and Enzymatic Cleavage

Cleavage reactions with CNBr are analyzed using Con A binding for detection of fragments associated with carbohydrate. Cleavage reactions are conducted using trifluoroacetic acid (TFA) in the presence and absence of CNBr. Reactions are conducted at 37° C. for 18 hours, and the samples are vacuum dried. The samples are washed with water, dissolved in SDS gel sample buffer with reducing agent, boiled and applied to an SDS gel. After electrophoresis, the protein is transferred to Immobilon membrane and visualized by Con A binding. In low concentrations of acid (1%), CNBr cleaves the majority of 16 kD and 18 kD species to one product, a species about 14 kD. In reactions using 10% TFA, a 14 kD species is observed both with and without CNBr.

Four proteolytic enzymes are used in these experiments to examine the digestion products of the 30 kD protein: 1) V-8 protease; 2) Endo Lys C protease; 3) pepsin; and 4) trypsin. Except for pepsin, the digestion buffer for the enzymes is 0.1 M ammonium bicarbonate, pH 8.3. The pepsin reactions are done in 0.1% TFA. The digestion volume is 100 ml and the ratio of enzyme to substrate is 1:10. $^{125}$I-labelled 30 kD osteogenic protein is added for detection. After incubation at 37° C. for 16 hr., digestion mixtures are dried down and taken up in gel sample buffer containing dithiothreitol for SDS-PAGE. FIG. 6 shows an autoradiograph of an SDS gel of the digestion products. The results show that under these conditions, only trypsin digests the reduced 16 kD/18 kD species completely and yields a major species at around 12 kD. Pepsin digestion yields better defined, lower molecular weight species. However, the 16 kD/18 kD fragments were not digested completely. The V-8 digest shows limited digestion with one dominant species at 16 kD.

C5. Protein Sequencing

Figure 7A:
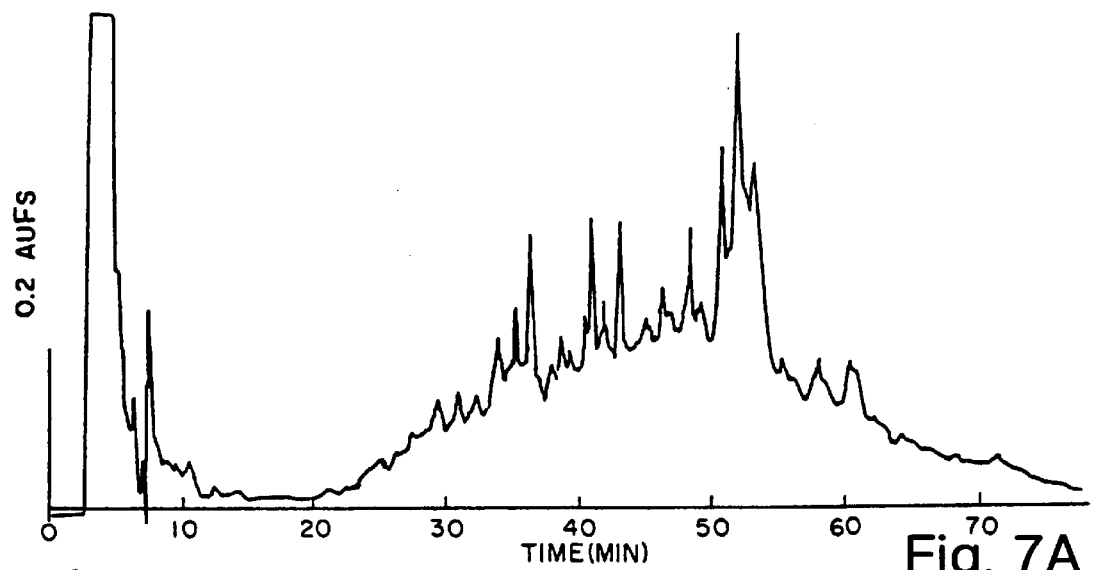
FIG. 7 is a collection of HPLC chromatograms of tryptic peptide digestions of 30 kD BOP (A), the 16 kD subunit (B), and the 18 kD subunit (C)

To obtain amino acid sequence data, the protein is cleaved with trypsin or Endoproteinase Asp-N (EndoAsp-N). The tryptic digest of reduced and carboxymethylated 30 kD protein (approximately 10 mg) is fractionated by reverse-phase HPLC using a C-8 narrowbore column (13 cm×2.1 mm ID) with a TFA/acetonitrile gradient and a flow rate of 150 ml/min. The gradient employs (A) 0.06% TFA in water and (B) 0.04% TFA in water and acetonitrile (1:4; v:v). The procedure was 10% B for five min., followed by a linear gradient for 70 min. to 80% B, followed by a linear gradient for 10 min. to 100% B. Fractions containing fragments as determined from the peaks in the HPLC profile (FIG. 7A) are rechromatographed at least once under the same conditions in order to isolate single components satisfactory for sequence analysis.

Figure 7B:
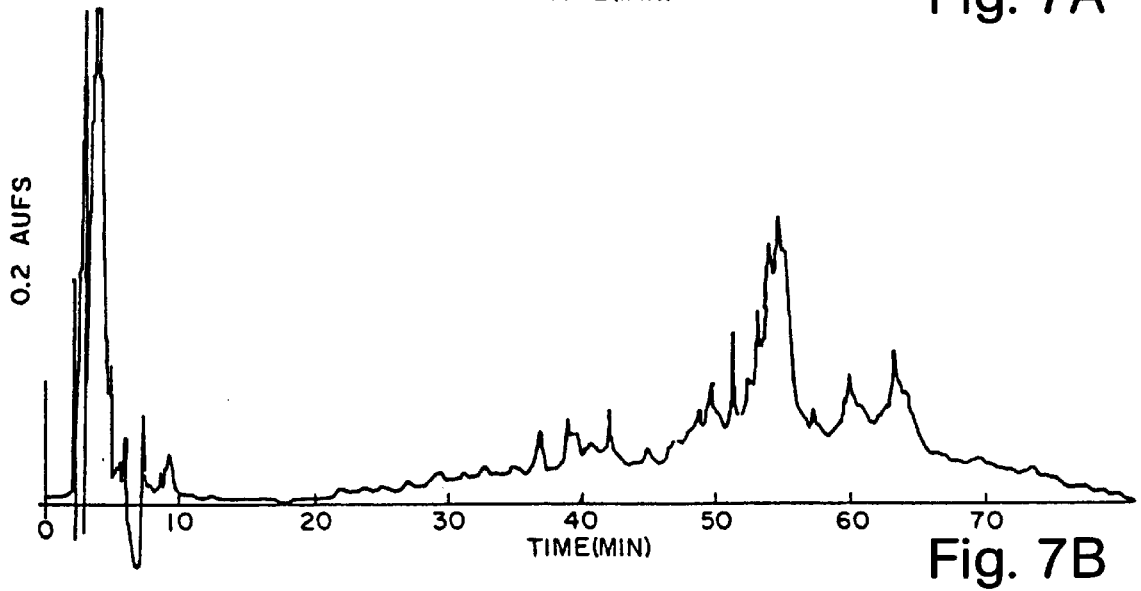
Figure 7C:
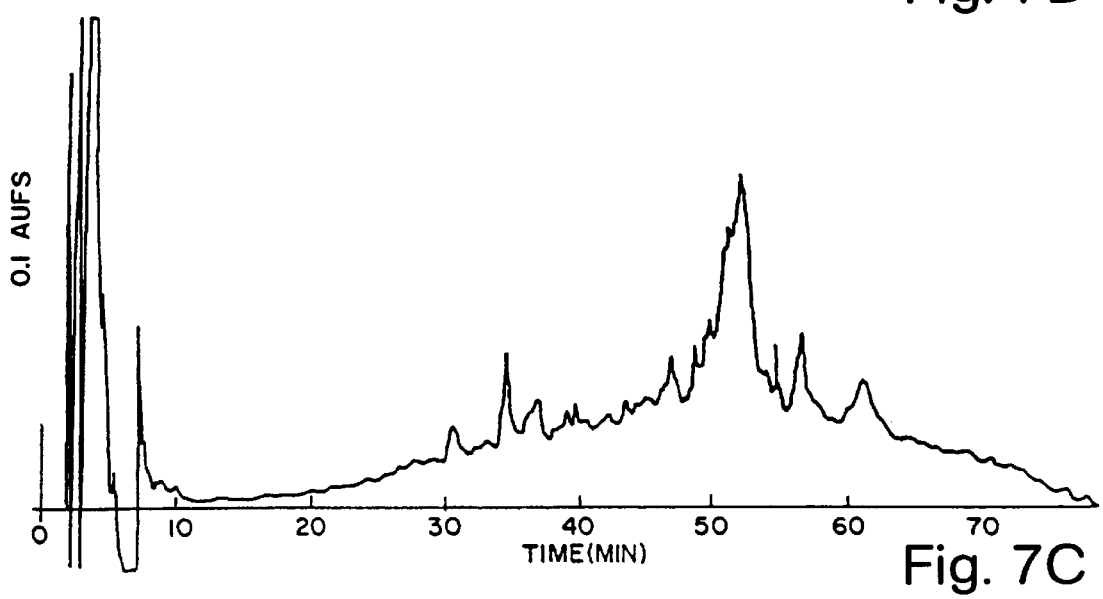

The HPLC profiles of the similarly digested 16 kD and 18 kD subunits are shown in FIGS. 7B and 7C, respectively. These peptide maps are similar suggesting that the subunits are identical or are closely related.

Figure 16A:
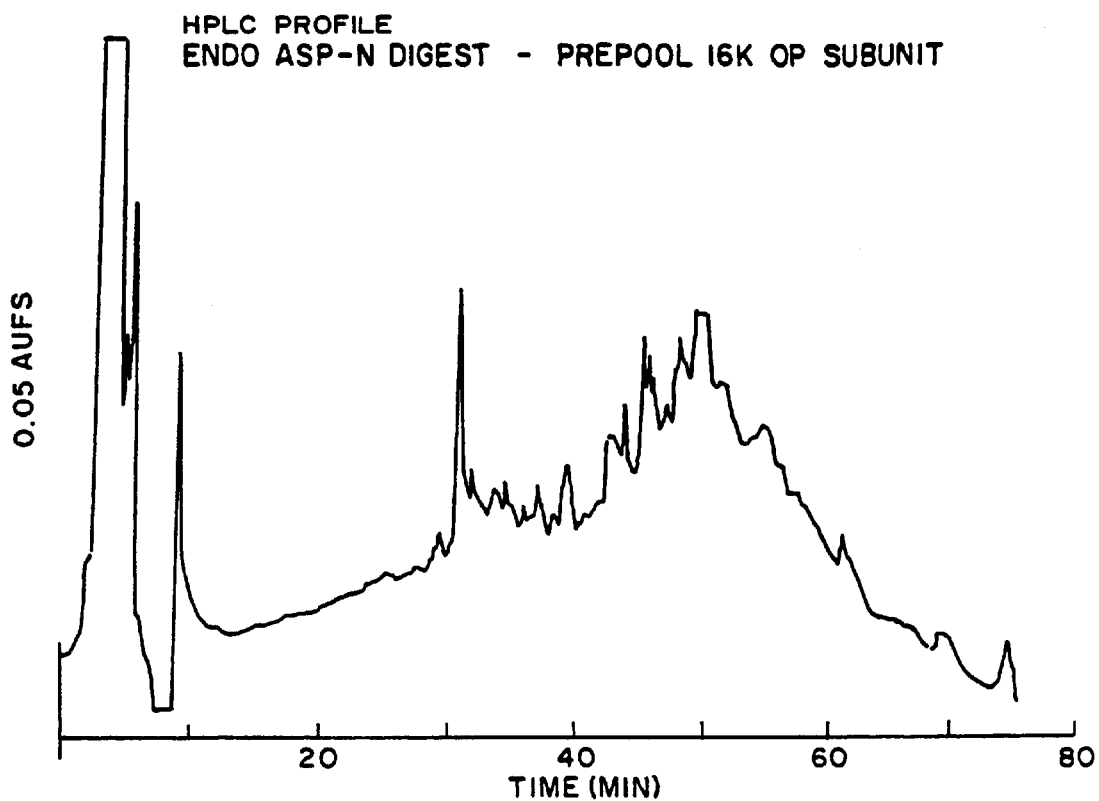
FIG. 16 is a pair of HPLC chromatograms of Endo Asp N proteinase digests of the 18 kD subunit (A) and the 16 kD subunit (B)
Figure 16B:
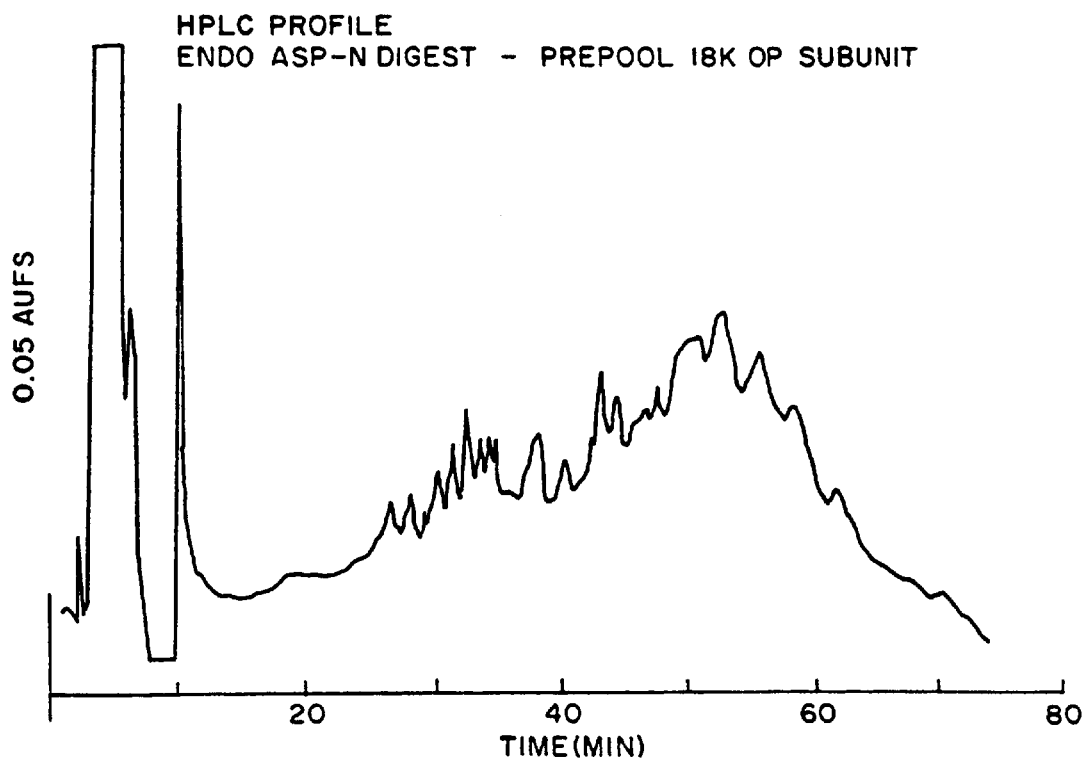

The 16 kD and 18 kD subunits are digested with Endo Asp N proteinase. The protein is treated with 0.5 mg EndoAsp-N in 50 mM sodium phosphate buffer, pH 7.8 at 36° C. for 20 hr. The conditions for fractionation are the same as those described previously for the 30 kD, 16 kD, and 18 kD digests. The profiles obtained are shown in FIGS. 16A and 16B.

Various of the peptide fragments produced using the foregoing procedures have been analyzed in an automated amino acid sequencer (Applied Biosystems 470A with 120A on-line PTH analysis). The following sequence data has been obtained:

(1) S-F-D-A-Y-Y-C-S-G-A-C-Q-F-P-M-P-K;
(2) S-L-K-P-S-N-Y-A-T-I-Q-S-I-V;
(3) A-C-C-V-P-T-E-L-S-A-I-S-M-L-Y-L-D-E-N-E-K;
(4) M-S-S-L-S-I-L-F-F-D-E-N-K;
(5) S-Q-E-L-Y-V-D-F-Q-R;
(6) F-L-H-C-Q-F-S-E-R-N-S;
(7) T-V-G-Q-L-N-E-Q-S-S-E-P-N-I-Y;
(8) L-Y-D-P-M-V-V;
(9) V-G-V-V-P-G-I-P-E-P-C-C-V-P-E;
(10) V-D-F-A-D-I-G;
(11) V-P-K-P-C-C-A-P-T;
(12) I-N-I-A-N-Y-L;
(13) D-N-H-V-L-T-M-F-P-I-A-I-N;
(14) D-E-Q-T-L-K-K-A-R-R-X-Q-W-I-?-P;
(15) D-I-G-?-S-E-W-I-I-?-P;
(16) S-I-V-R-A-V-G-V-P-G-I-P-E-P-?-?-V;
(17) D-?-I-V-A-P-P-Q-Y-H-A-F-Y;
(18) D-E-N-K-N-V-V-L-K-V-Y-P-N-M-T-V-E;
(19) S-Q-T-L-Q-F-D-E-Q-T-L-K-?-A-R-?-K-Q;
(20) D-E-Q-T-L-K-K-A-R-R-K-Q-W-I-E-P-R-N-?-A-R-R-Y-L;
(21) A-R-R-K-Q-W-I-E-P-R-N-?-A-?-R-Y-?-?-V-D; and
(22) R-?-Q-W-I-E-P-?-N-?-A-?-?-Y-L-K-V-D-?-A-?-?-G.

C6. Amino Acid Analysis

Strategies for obtaining amino acid composition were developed using gel elution from 15% SDS gels, transfer onto Immobilon, and hydrolysis. Immobilon membrane is a polymer of vinylidene difluoride and, therefore, is not susceptible to acid cleavage. Samples of oxidized (30 kD) and reduced (16 kD and 18 kD) BOP are electrophoresed on a gel and transferred to Immobilon for hydrolysis and analysis as described below. The composition data generated by amino acid analyses of 30 kD BOP is reproducible, with some variation in the number of residues for a few amino acids, especially cysteine and isoleucine.

Samples are run on 15% SDS gels, transferred to Immobilon, and stained with Coomassie blue. The bands of interest are excised from the Immobilon, with a razor blade and placed in a 6×50 mm Corning test tube cleaned by pyrolysis at 550° C. When cysteine is to be determined, the samples are treated with performic acid, which converts cysteine to cysteic acid. Cysteic acid is stable during hydrolysis with HCl, and can be detected during the HPLC analysis by using a modification of the normal Pico-Tag eluents (Millipore) and gradient. The performic acid is made by mixing 50 ml 30% hydrogen peroxide with 950 ml 99% formic acid, and allowing this solution to stand at room temperature for 2 hr. The samples are then treated with performic acid (PFA); 20 ml PFA is pippetted onto each sample and placed in an ice bath at 4° C. for 2.5 hours. After 2.5 hr. the PFA is removed by drying in vacuo, and the samples are then hydrolyzed. A standard protein of known composition and concentration containing cysteine is treated with PFA and hydrolyzed concurrently with the osteogenic protein samples, to take as a control for hydrolysis and amino acid chromatography.

The hydrolysis of the osteogenic protein samples is done in vacuo. The samples, with empty tubes and Immobilon blanks, are placed in a hydrolysis vessel which is placed in a dry ice/ethanol bath to keep the HCl from prematurely evaporating. 200 ml 6 N HCl containing 2% phenol and 0.1% stannous chloride are added to the hydrolysis vessel outside the tubes containing the samples. The hydrolysis vessel is then sealed, flushed with prepurified nitrogen, evacuated, and then held at 115° C. for 24 hours, after which time the HCl is removed by drying in vacuo.

After hydrolysis, each piece of Immobilon is transferred to a fresh tube, where it is rinsed twice with 100 ml 0.1% TFA, 50% acetonitrile. The washings are returned to the original sample tube, which is then redried as below. A similar treatment of amino acid analysis on Immobilon can be found in the literature (LeGendre and Matsudaira (1988) Biotechniques 6:154–159).

The samples are redried twice using 2:2:1 ethanol:water:triethylamine and allowed to dry at least 30 min. after each addition of redry reagent. These redrying steps bring the sample to the proper pH for derivatization.

The samples are derivatized using standard methodology. The solution is added to each sample tube. The tubes are placed in a desiccator which is partially evacuated, and are allowed to stand for 20 min. The desiccator is then fully evacuated, and the samples are dried for at least 3 hr. After this step the samples may be stored under vacuum at −20° C. or immediately diluted for HPLC. The samples are diluted with Pico-Tag Sample Diluent (generally 100 ml) and allowed to stand for 20 min., after which they are analyzed on HPLC using the Pico Tag chromatographic system with some minor changes involving gradients, eluents, initial buffer conditions and oven temperature.

After HPLC analysis, the compositions are calculated. The molecular weights are assumed to be 14.4 kD, 16.2 kD, and 27 kD to allow for 10% carbohydrate content. The number of residues is approximated by dividing the molecular weight by the average molecular weight per amino acid, which is 115. The total picomoles of amino acid recovered is divided by the number of residues, and then the picomoles recovered for each amino acid is divided by the number of picomoles per residue, determined above. This gives an approximate theoretical number of residues of each amino acid in the protein. Glycine content may be overestimated in this type of analysis.

Composition data obtained are shown in TABLE 5.

TABLE 5

| BOP Amino Acid Analyses | | | |
|---|---|---|---|
| Amino Acid | 30 kD | 16 kD | 18 kD |
| Aspartic Acid/Asparagine | 22 | 14 | 15 |
| Glutamic Acid/Glutamine | 24 | 14 | 16 |
| Serine | 24 | 16 | 23 |
| Glycine | 29 | 18 | 26 |
| Histidine | 5 | * | 4 |
| Arginine | 13 | 6 | 6 |

TABLE 5-continued

| BOP Amino Acid Analyses | | | |
|---|---|---|---|
| Amino Acid | 30 kD | 16 kD | 18 kD |
| Threonine | 11 | 6 | 7 |
| Alanine | 18 | 11 | 12 |
| Proline | 14 | 6 | 6 |
| Tyrosine | 11 | 3 | 3 |
| Valine | 14 | 6 | 7 |
| Methionine | 3 | 0 | 2 |
| Cysteine** | 16 | 14 | 12 |
| Isoleucine | 15 | 14 | 10 |
| Leucine | 15 | 8 | 9 |
| Phenylalanine | 7 | 4 | 4 |
| Tryptophan | ND | ND | ND |
| Lysine | 12 | 6 | 6 |

*This result is not integrated because histidine is present in low quantities.
**Cysteine is corrected by percent normally recovered from performic acid hydrolysis of the standard protein.

The results obtained from the 16 kD and 18 kD subunits, when combined, closely resemble the numbers obtained from the native 30 kD protein. The high figures obtained for glycine and serine are most likely the result of gel elution.

D. PURIFICATION OF HUMAN OSTEOGENIC PROTEIN

Human bone is obtained from the Bone Bank, (Massachusetts General Hospital, Boston, Mass.), and is milled, defatted, demarrowed and demineralized by the procedure disclosed above. 320 g of mineralized bone matrix yields 70–80 g of demineralized bone matrix. Dissociative extraction and ethanol precipitation of the matrix gives 12.5 g of guanidine-HCl extract.

Figure 10A:
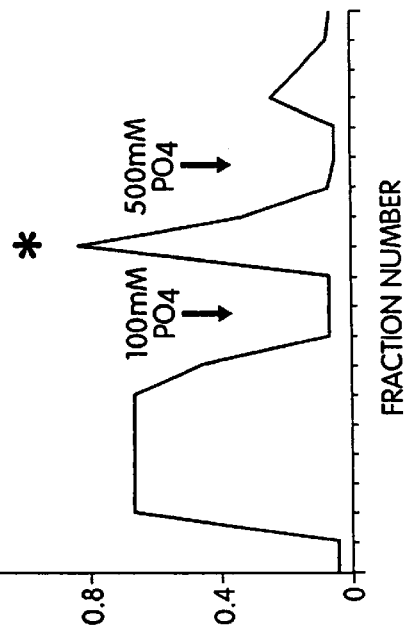
FIG. 10 is a collection of graphs of protein concentration (as indicated by optical absorption) vs. elution volume illustrating the results of human protein fractionation on heparin-Sepharose I (A), HAP-Ultragel (B), TSK 3000/2000 (C), and heparin-Sepharose II (D). Arrows indicate buffer changes.
Figure 10B:
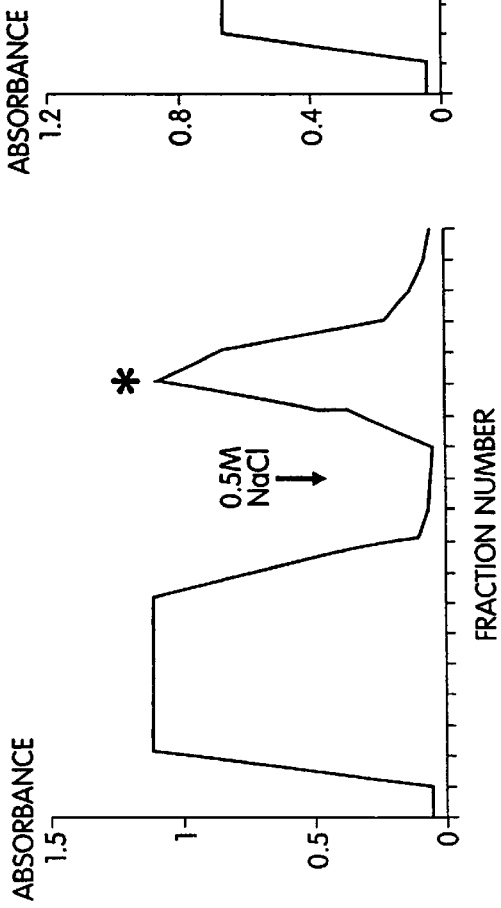
Figure 10C:
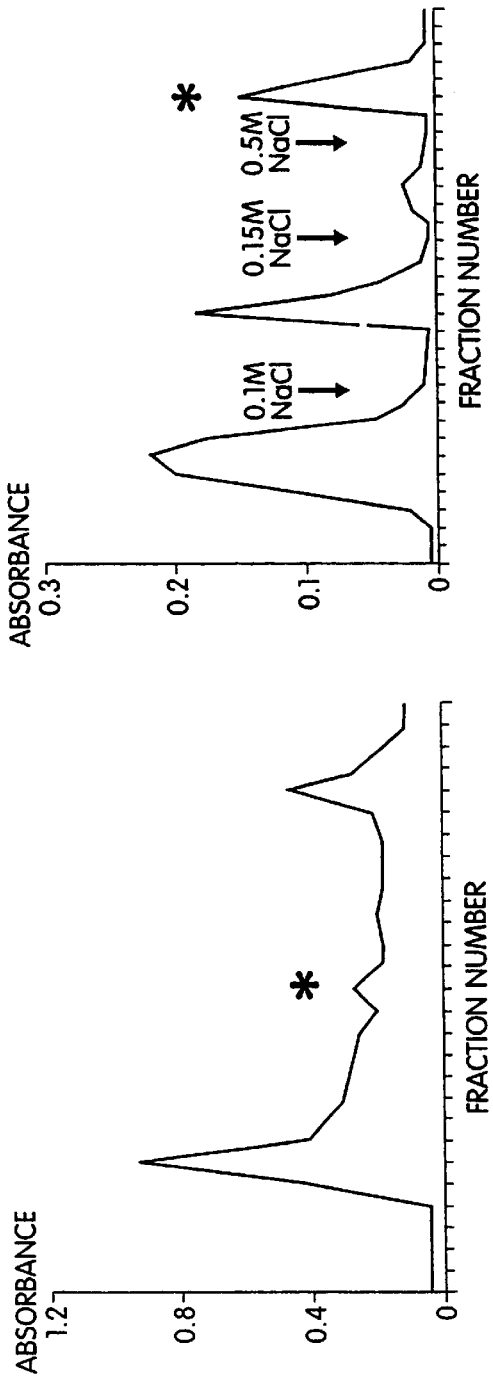
Figure 10D:
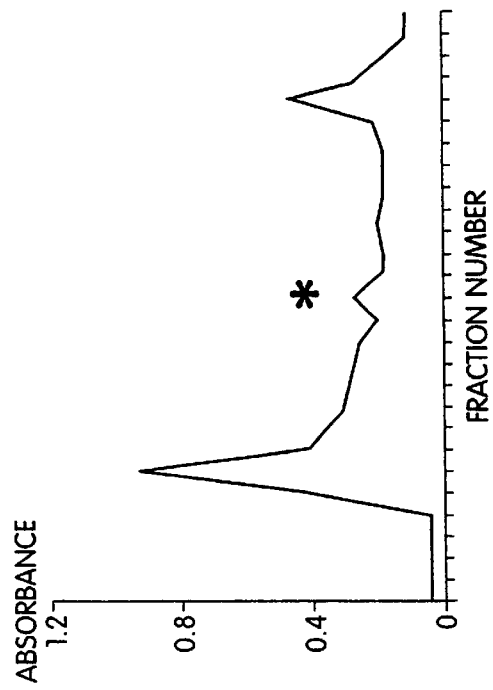

One third of the ethanol precipitate (0.5 g) is used for gel filtration through 4 M guanidine-HCl (FIG. 10A). Approximately 70–80 g of ethanol precipitate per run is used. In vivo bone inducing activity is localized in the fractions containing proteins in the 30 kD range. They are pooled and equilibrated in 6 M urea, 0.5 M NaCl buffer, and applied directly onto a HAP column; the bound protein is eluted stepwise by using the same buffer containing 100mM and 500 mM phosphate (FIGURE 10B). Bioassay of HAP bound and unbound fractions demonstrates that only the fraction eluted by 100 mM phosphate has bone inducing activity in vivo. The biologically active fraction obtained from HAP chromatography is subjected to heparin-Sepharose affinity chromatography in buffer containing low salt; the bound proteins are eluted by 0.5 M NaCl (FIG. 10C). Assaying the heparin-Sepharose fractions shows that the bound fraction eluted by 0.5M NaCl have bone-inducing activity. The active fraction is then subjected to C-18 reverse phase chromatography. (FIG. 10D).

The active fraction can then be subjected to SDS-PAGE as noted above to yield a band at about 30 kD comprising substantially pure human osteogenic protein.

E. BIOSYNTHETIC PROBES FOR ISOLATION OF GENES ENCODING NATIVE OSTEOGENIC PROTEIN

E-1 Probe Design

A synthetic consensus gene shown in FIG. 13 was designed as a hybridization probe (and to encode a consensus protein, see below) based on amino acid predictions from homology with the TGF-beta gene family and using human codon bias as found in human TGF-beta. The designed concensus sequence was then constructed using known techniques involving assembly of oligonucleotides manufactured in a DNA synthesizer.

Tryptic peptides derived from BOP and sequenced by Edman degradation provided amino acid sequences that showed strong homology with the Drosophila DPP protein sequence (as inferred from the gene), the Xenopus VG1 protein, and somewhat less homology to inhibin and TGF-beta, as demonstrated below in TABLE 6.

TABLE 6

| protein | amino acid sequence | homology |
|---|---|---|
| (BOP) | SFDAYYCSGACQFPS | |
| | ***** * * ** | (9/15 matches) |
| (DPP) | GYDAYYCHGKCPFFL | |
| (BOP) | SFDAYYCSGACQFPS | |
| | * ** * * * | (6/15 matches) |
| (Vg1) | GYMANYCYGECPYPL | |
| (BOP) | SFDAYYCSGACQFPS | |
| | * ** * * | (5/15 matches) |
| (inhibin) | GYHANYCEGECPSHI | |
| (BOP) | SFDAYYCSGACQFPS | |
| | * * * * | (4/15 matches) |
| (TGF-beta) | GYHANFCLGPCPYIW | |
| (BOP) | K/RACCVPTELSAISMLYLDEN | |
| | ***** * **** * * | (12/20 matches) |
| (Vg1) | LPCCVPTKMSPISMLFYDNN | |
| (BOP) | K/RACCVPTELSAISMLYLDEN | |
| | * ***** * **** * | (12/20 matches) |
| (inhibin) | KSCCVPTKLRPMSMLYYDDG | |
| (BOP) | K/RACCVPTELSAISMLYLDE | |
| | **** * * | (6/19 matches) |
| (TGF-beta) | APCCVPQALEPLPIVYYVG | |
| (BOP) | K/RACCVPTELSAISMLYLDEN | |
| | ******* * **** | (12/20 matches) |
| (DPP) | KACCVPTQLDSVAMLYLNDQ | |
| (BOP) | LYVDF | |
| | ***** | (5/5 matches) |
| (DPP) | LYVDF | |
| (BOP) | LYVDF | |
| | *** * | (4/5 matches) |
| (Vg1) | LYVEF | |
| (BOP) | LYVDF | |
| | ** ** | (4/5 matches) |
| (TGF-beta) | LYIDF | |
| (BOP) | LYVDF | |
| | * * | (2/4 matches) |
| (inhibin) | FFVSF | |

*match

In determining the amino acid sequence of an osteogenic protein (from which the nucleic acid sequence can be determined), the following points were considered: (1) the amino acid sequence determined by Edman degradation of osteogenic protein tryptic fragments is ranked highest as long as it has a strong signal and shows homology or conservative changes when aligned with the other members of the gene family; (2) where the sequence matches for all four proteins, it is used in the synthetic gene sequence; (3) matching amino acids in DPP and Vg1 are used; (4) If Vg1 or DPP diverged but either one were matched by inhibin or by TGF-beta, this matched amino acid is chosen; (5) where all sequences diverged, the DPP sequence is initially chosen, with a later plan of creating the Vg1 sequence by mutagenesis kept as a possibility. In addition, the consensus sequence is designed to preserve the disulfide crosslinking and the apparent structural homology.

One purpose of the originally designed synthetic consensus gene sequence, designated COP0, (see FIG. 13), was to serve as a probe to isolate natural genes. For this reason the DNA was designed using human codon bias. Alternatively, probes may be constructed using conventional techniques comprising a group of sequences of nucleotides which encode any portion of the amino acid sequence of the osteogenic protein produced in accordance with the foregoing isolation procedure. Use of such pools of probes also will enable isolation of a DNA encoding the intact protein.

E-2 Retrieval of Genes Encoding Osteoaenic Protein from Genomic Library

A human genomic library (Maniatis-library) carried in lambda phage (Charon 4A) was screened using the COP0 consensus gene as probe. The initial screening was of 500,000 plaques (10 plates of 50,000 each). Areas giving hybridization signal were punched out from the plates, phage particles were eluted and plated again at a density of 2000–3000 plaques per plate. A second hybridization yielded plaques which were plated once more, this time at a density of ca 100 plaques per plate allowing isolation of pure clones. The probe (COP0) is a 300 base pair BamHI-PstI fragment restricted from an amplification plasmid which was labeled using alpha 32 dCTP according to the random priming method of Feinberg and Vogelstein, Anal. Biochem., 137, 266–267, 1984. Prehybridization was done for 1 hr in 5×SSPE, 10×Denhardt's mix, 0.5% SDS at 50° C. Hybridization was overnight in the same solution as above plus probe. The washing of nitrocellulose membranes was done, once cold for 5 min. in 1×SSPE with 0.1% SDS and twice at 50° C. for 2×30 min. in the same solution. Using this procedure, twenty-four positive clones were found. Two of these yielded the genes corresponding to BMP-2b, one yielded BMP-3 (see PCT US 87/01537) and two contained a gene never before reported designated OP1, osteogenic protein-1 described below.

Southern blot analysis of lambda #13 DNA showed that an approximately 3 kb BamHI fragment hybridized to the probe. (See FIG. 1B). This fragment was isolated and subcloned into a bluescript vector (at the BamHI site). The clone was further analyzed by Southern blotting and hybridization to the COP0 probe. This showed that a 1 kb (approx.) EcoRI fragment strongly hybridized to the probe. This fragment was subcloned into the EcoRI site of a bluescript vector, and sequenced. Analysis of this sequence showed that the fragment encoded the carboxy terminus of a protein, named osteogenic protein-1 (OP1). The protein was identified by amino acid homology with the TGF-beta family. For this comparison cysteine patterns were used and then the adjacent amino acids were compared. Consensus splice signals were found where amino acid homologies ended, designating exon intron boundaries. Three exons were combined to obtain a functional TGF-beta-like domain containing seven cysteines. Two introns were deleted by looping out via primers bridging the exons using the single stranded mutagenesis method of Kunkel. Also, upstream of the first cysteine, an EcoRI site and an asp-pro junction for acid cleavage were introduced, and at the 3' end a PstI site was added by the same technique. Further sequence information (penultimate exon) was obtained by sequencing the entire insert. The sequencing was done by generating a set of unidirectionally deleted clones (Ozkaynak, E., and Putney, S.: Biotechniques, 5, 770–773, 1987). The obtained sequence covers about 80% of the TGF-beta-like region of OP1 and is set forth in FIG. 1A. The complete sequence of the TGF-beta like region was obtained by first subcloning all EcoRI generated fragments of lambda clone #13 DNA and sequencing a 4 kb fragment that includes the first portion of the TGF-beta like region (third exon counting from end) as well as sequences characterized earlier. The gene on an EcoRI to PstI fragment was inserted into an E. coli expression vector controlled by the trp promoter-operator to produce a modified trp LE fusion protein with an acid cleavage site. The OP1 gene encodes amino acids corresponding substantially to a peptide found in sequences of naturally sourced material. The amino acid sequence of what is believed to be its active region is set forth below:

```
        1         10          20         30        40
OP1       LYVSFR-DLGWQDWIIAPEGYAAYYCEGECAFPLNS
                  50           60         70
          YMNATN--H-AIVQTLVHFINPET-VPKPCCAPTQLNA
                  80           90        100
          ISVLYFDDSSNVILKKYRNRVRACGCH
```

A longer active sequence is:

```
                                              -5
                                           HQRQA
        1          10         20         30        40
OP1    CKKHELYVSFR-DLGWQDWIIAPEGYAAYYCEGECAFPLNS
                   50         60         70
          YMNATN--H-AIVQTLVHFINPET-VPKPCCAPTQLNA
                   80         90        100
          ISVLYFDDSSNVILKKYRNMRACGCH
```

E-3  Probing cDNA Library

Another example of the use of pools of probes to enable isolation of a DNA encoding the intact protein is shown by the following. Cells known to express the protein are extracted to isolate total cytoplasmic RNA. An oligo-dT column can be used to isolate mRNA. This mRNA can be size fractionated by, for example, gel electrophoresis. The fraction which includes the mRNA of interest may be determined by inducing transient expression in a suitable host cell and testing for the presence of osteogenic protein using, for example, antibody raised against peptides derived from the tryptic fragments of osteogenic protein in an immunoassay. The mRNA fraction is then reverse transcribed to single stranded cDNA using reverse transcriptase; a second complementary DNA strand can then be synthesized using the cDNA as a template. The double-standard DNA is then ligated into vectors which are used to transfect bacteria to produce a cDNA library.

The radiolabelled consensus sequence, portions thereof, and/or synthetic deoxy oligonucleotides complementary to codons for the known amino acid sequences in the osteogenic protein may be used to identify which of the DNAs in the cDNA library encode the full length osteogenic protein by standard DNA-DNA hybridization techniques.

The cDNA may then be integrated in an expression vector and transfected into an appropriate host cell for protein expression. The host may be a prokaryotic or eucaryotic cell since the former's inability to glycosylate osteogenic protein will not effect the protein's enzymatic activity. Useful host cells include Saccharomyces, E. coli, and various mammalian cell cultures. The vector may additionally encode various signal sequences for protein secretion and/or may encode osteogenic protein as a fusion protein. After being translated, protein may be purified from the cells or recovered from the culture medium.

II. RECOMBINANT NON-NATIVE OSTEOGENIC PROTEIN CONSTRUCTS

A. Protein Design

This section discloses the production of novel recombinant proteins capable of inducing cartilage and endochondral bone comprising a protein structure duplicative of the functional domain of the amino acid sequence encoded by consensus DNA sequences derived from a family of natural proteins implicated in tissue development. These gene products/proteins are known to exist in active form as dimers and are, in general, processed from a precursor protein to produce an active C-terminal domain of the precursor.

The recombinant osteogenic/chondrogenic proteins are "novel" in the sense that, as far as applicants are aware, they do not exist in nature or, if they do exist, have never before been associated with bone or cartilage formation. The approach to design of these proteins was to employ amino acid sequences, found in the native isolates described above, in polypeptide structures which are patterned after certain proteins reported in the literature, or the amino acid sequences inferred from DNAs reported in the literature. Thus, using the design criteria set forth above in the probe design section, and refining the amino acid sequence as more protein sequence information was learned, a series of synthetic proteins were designed with the hope and intent that they might have osteogenic or chondrogenic activity when tested in the bioassay system disclosed below.

It was noted, for example, that DPP from drosophila, VG1 from Xenopus, the TGF beta family of proteins, and to a lesser extent, alpha and beta inhibins, had significant homologies with certain of the sequences derived from the naturally sourced OP product. (FIG. 18.) Study of these proteins led to the realization that a portion of the sequence of each had a structural similarity observable by analysis of the positional relationship of cysteines and other amino acids which have an important influence on three dimensional protein conformation. It was noted that a region of these sequences had a series of seven cysteines, placed very nearly in the same relative positions, and certain other amino acids in sequence as set forth below:

```
            10         20         30         40         50
      CXXXXLXVXFXDXGWXXWXXXPXGXXAXYCXGXCXXPXXXXXXXXNHAXX
            60         70         80         90        100
      QXXVXXXNXXXXPXXCCXPXXXXXXXXLXXXXXXXVXLXXYXXMXVXXCXCX
``` wherein each X independently represents an amino acid. Expression experiments with constructs patterned after this template amino acid sequence showed activity occurred with a shorter sequence having only six cysteines:

```
            10        20        30        40        50
      LXVXFXDXGWXXWXXPXGXXAXYCXGXCXXPXXXXXXXXXNHAXX
            60        70        80        90       100
      QXXVXXXNXXXXPXXCCXPXXXXXXXXLXXXXXXXXVXLXXYXXMXVXXCXCX
``` wherein each X independently represents an amino acid. Within these generic structures are a mulitiplicity of specific sequences which have osteogenic or chondrogenic activity. Preferred structures are those having the amino acid sequence:

```
                 10        20        30        40        50
      CKRHPLYVDFRDVGWNDWIVAPPGYHAFYCHGECPFPLADHLNSTNHAIV
      RRRS K  S  S  L   QE VIS E FD  Y  E A AY MPESMKAS     VI
           KE F  E  K   I  DN  L   N  S Q   ITK F P         TL
           Q     A  S       K
                 60        70        80        90       100
      QTLVNSVNPGKIPKACCVPTELSAISMLYLDENENVVLKNYQDMVVEGCGCR
       SI HAI SEQV EP  A EQMNSLAI FFNDQDK I  RK EE T DA H H
          RF     T  S      K DPV V  Y N S    H  RN   RS
             N          S                 K         P   E
``` wherein, in each position where more than one amino acid is shown, any one of the amino acids shown may be used. Novel active proteins also are defined by amino acid sequences comprising an active domain beginning at residue number 6 of this sequence, i.e, omitting the N terminal CXXXX, or omitting any of the preferred specific combinations such as CKRHP, CRRKQ, CKRHE, etc, resulting in a construct having only 6 cysteine residues. After this work, PCT 87/01537 was published, and it was observed that the proteins there identified as BMPII a and b and BMPIII each comprised a region embodying this generic structure. These proteins were not demonstrated to be osteogenic in the published application. However, applicants discovered that a subpart of the amino acid sequence of these proteins, properly folded, and implanted as set forth herein, is active. These are disclosed herein as CBMPIIa, CBMPIIb, and CBMPIII. Also, the OP1 protein was observed to exhibit the same generic structure.

Thus, the preferred osteogenic proteins are expressed from recombinant DNA and comprise amino acid sequences including any of the following sequences:

```
              1        10        20        30        40
      Vg1     CKKRHLYVEFK-DVGWQNWVIAPQGYMANYCYGECPYPLTE
                       50        60        70
              ILNGSN--H-AILQTLVHSIEPED-IPLPCCVPTKMSP
                    80        90       100
              ISMLFYDNNDNVVLRHYENMAVDECGCR 1        10        20        30        40
      DPP     CRRHSLYVDFS-DVGWDDWIVAPLGYDAYYCHGKCPFPLAD
                       50        60        70
              HFNSTN--H-AVVQTLVNNNNPGK-VPKACCVPTQLDS
                    80        90       100
              VAMLYLNDQSTVVLKNYQEMTVVGCGCR 1        10        20        30        40
      OP1        LYVSFR-DLGWQDWIIAPEGYAAYYCEGECAFPLNS
                       50        60        70
              YMNATN--H-AIVQTLVHFINPET-VPKPCCAPTQLNA
                    80        90       100
              ISVLYFDDSSNVILKKYRNMVVRACGCH
                                                       -5
                                                    HQRQA
              1        10        20        30        40
```

```
                       -continued
      OP1     CKKHELYVSFR-DLGWQDWIIAPEGYAAYYCEGECAFPLNS
                       50        60        70
```

```
                       -continued
              YMNATN--H-AIVQTLVHFINPET-VPKPCCAPTQLNA
                    80        90       100
              ISVLYFDDSSNVILKKYRNMVVRACGCH 1        10        20        30        40
      CBMP-2a CKRHPLYVDFS-DVGWNDWIVAPPGYHAFYCHGECPFPLAD
                       50        60        70
              HLNSTN--H-AIVQTLVNSVNS-K-IPKACCVPTELSA
                    80        90       100
              ISMLYLDENEKVVLKNYQDMVVEGCGCR 1        10        20        30        40
      CBMP-2b CRRHSLYVDFS-DVGWNDWIVAPPGYQAFYCHGDCPFPLAD
                       50        60        70
              HLNSTN--H-AIVQTLVNSVNS-S-IPKACCVPTELSA
                    80        90       100
              ISMLYLDEYDKVVLKNYQEMVVEGCGCR 1        10        20        30        40
      CBMP-3  CARRYLKVDFA-DIGWSEWIISPKSFDAYYCSGACQFPMPK
                       50        60        70
              SLKPSN--H-ATIQSIVRAVGVVPGIPEPCCVPEKMSS
                    80        90       100
              LSILFFDENKNVVLKVYPNMTVESCACR 1        10        20        30        40
      COP1       LYVDFQRDVGWDDWIIAPVDFDAYYCSGACQFPSAD
                       50        60        70
              HFNSTN--H-AVVQTLVNNMNPGK-VPKPCCVPTELSA
                    80        90       100
              ISMLYLDENSTVVLKNYQEMTVVGCGCR 1        10        20        30        40
      COP3       LYVDFQRDVGWDDWIVAPPGYQAFYCSGACQFPSAD
                       50        60        70
              HFNSTN--H-AVVQTLVNNMNPGK-VPKPCCVPTELSA
                    80        90       100
              ISMLYLDENEKVVLKNYQEMVVEGCGCR 1        10        20        30        40
      COP4       LYVDFS-DVGWDDWIVAPPGYQAFYCSGACQFPSAD
                       50        60        70
              HFNSTN--H-AVVQTLVNNMNPGK-VPKPCCVPTELSA
                    80        90       100
              ISMLYLDENEKVVLKNYQEMVVEGCGCR 1        10        20        30        40
      COP5       LYVDFS-DVGWDDWIVAPPGYQAFYCHGECPFPLAD
                       50        60        70
              HFNSTN--H-AVVQTLVNSVNSKI--PKACCVPTELSA
```

-continued
```
            80         90        100
       ISMLYLDENEKVVLKNYQEMVVEGCGCR 1        10        20         30        40
COP7        LYVDFS-DVGWNDWIVAPPGYHAFYCHGECPFPLAD
                    50        60        70
       HLNSTN--H-AVVQTLVNSVNSKI--PKACCVPTELSA
            80        90        100
       ISMLYLDENEKVVLKNYQEMVVEGCGCR
                                          10
                                  PKHHSQRARKKNKN 1        10        20         30        40
COP16   CRRHSLYVDFS-DVGWNDWIVAPPGYQAFYCHGECPFPLAD
                    50        60        70
       HFNSTN--H-AVVQTLVNSVNSKI--PKACCVPTELSA
            80        90        100
       ISMLYLDENEKVVLKNYQEMVVEGCGCR
```

As shown in FIG. 18, these sequences have considerable homology with the alpha and beta inhibins, three forms of TGF beta, and MIS.

B. Gene Prepartaion

The synthetic genes designed as described above preferably are produced by assembly of chemically synthesized oligonucleotides. 15–100 mer oligonucleotides may be synthesized on a Biosearch DNA Model 8600 Synthesizer, and purified by polyacrylamide gel electrophoresis (PAGE) in Tris-Borate-EDTA buffer (TBE). The DNA is then electro-eluted from the gel. Overlapping oligomers may be phosphorylated by T4 polynucleotide kinase and ligated into larger blocks which may also be purifed by PAGE. Natural gene sequences and cDNAs also may be used for expression.

C. Expression

Figure 21A:
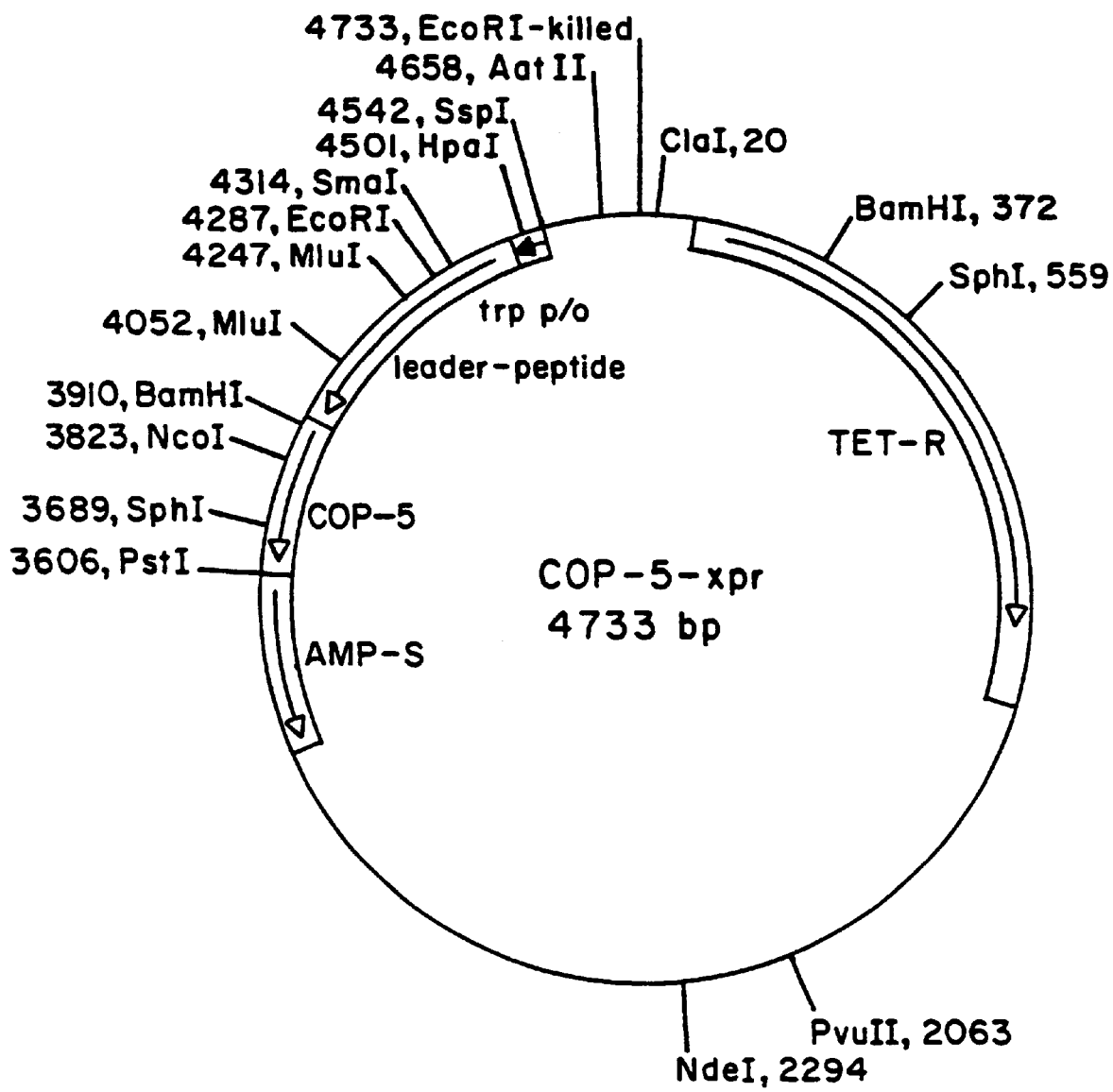
FIG. 21A is an *E. coli* expression vector containing a gene of an osteogenic protein fused to a leader protein.

The genes can be expressed in appropriate prokaryotic hosts such as various strains of *E. coli*. For example, if the gene is to be expressed in *E. coli*, it must first be cloned into an expression vector. An expression vector (FIG. 21A) based on pBR322 and containing a synthetic trp promoter operator and the modified trp LE leader can be opened at the EcoRI and PSTI restriction sites, and a FB—FB COP gene fragment (FIG. 21B) can be inserted between these sites, where FB is fragment B of Staphylococcal Protein A. The expressed fusion protein results from attachment of the COP gene to a fragment encoding FB. The COP protein is joined to the leader protein via a hinge region having the sequence asp-pro-asn-gly. This hinge permits chemical cleavage of the fusion protein with dilute acid at the asp-pro site or cleavage at asn-gly with hydroxylamine, resulting in release of the COP protein.

D. Production of Active Proteins

The following procedure was followed for production of active recombinant protiens. *E. coli* cells containing the fusion proteins were lysed. The fusion proteins were purified by differential solubilization. In the case of the COP 1, 3, 4, 5, and 7 fusion proteins, cleavage was with dilute acid, and the resulting cleavage products were passed through a Sephacryl-200HR column. The Sephacryl column separated most of the uncleaved fusion products from the COP 1, 3, 4, 5, and 7 analogs. In the case of the COP 16 fusion protein, cleavage was with a more concentrated acid, and an SP-Trisacryl column was used to separate COP 16, the leader protein, and the residual fusion protein. The COP fractions from any of the COP analogs were then subjected to HPLC on a semi-prep C-18 column. The HPLC column primarily separated the leader proteins and other minor impurities from the COP analogs.

Initial conditions for refolding of COP analogs were at pH 8.0 using Tris, GuHCl, dithiothreitol. Final conditions for refolding of COP analogs were at pH 8.0 using Tris, oxidized glutathione, and lower amounts of GuHCl and dithiothreitol.

E. Production of Antisera

Antisera to COP 7 and COP5 were produced in New Zealand white rabbits. Western blots demonstrate that the antisera react with COP 7 and COP5 preparations. Antisera to COP 7 has been tested for reactivity to bovine osteogenic protein samples. Western blots show a clear reaction with the 30 kD protein and, when reduced, with the 16 kD subunit. The immunoreactive species appears as a closely-spared doublet in the 16K subunit region, similar to the 16K doublet seen in Con A blots.

III. MATRIX PREPARATION

A. General Consideration of Matrix Properties

The carrier described in the bioassay section; infra, may be replaced by either a biodegradable-synthetic or synthetic-inorganic matrix (e.g., HAP, collagen, tricalcium phosphate, or polylactic acid, polyglycolic acid and various copolymers thereof). Also xenogeneic bone may be used if pretreated as described below.

Studies have shown that surface charge, particle size, the presence of mineral, and the methodology for combining matrix and osteogenic protein all play a role in achieving successful bone induction. Perturbation of the charge by chemical modification abolishes the inductive response. Particle size influences the quantitative response of new bone; particles between 75 and 420 mm elicit the maximum response. Contamination of the matrix with bone mineral will inhibit bone formation. Most importantly, the procedures used to formulate osteogenic protein onto the matrix are extremely sensitive to the physical and chemical state of both the osteogenic protein and the matrix.

The sequential cellular reactions at the interface of the bone matrix/OP implants are complex. The multistep cascade includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

A successful carrier for osteogenic protein must perform several important functions. It must bind osteogenic protein and act as a slow release delivery system, accommodate each step of the cellular response during bone development, and protect the osteogenic protein from nonspecific proteolysis. In addition, selected materials must be biocompatible in vivo and biodegradable; the carrier must act as a temporary scaffold until replaced completely by new bone. Polylactic acid (PLA), polyglycolic acid (PGA), and various combinations have different dissolution rates in vivo. In bones, the dissolution rates can vary according to whether the implant is placed in cortical or trabecular bone.

Matrix geometry, particle size, the presence of surface charge, and porosity or the presence of interstices among the particles of a size sufficient to permit cell infiltration, are all important to successful matrix performance. It is preferred to shape the matrix to the desired form of the new bone and to have dimensions which span non-union defects. Rat studies show that the new bone is formed essentially having the dimensions of the device implanted.

The matrix may comprise a shape-retaining solid made of loosely adhered particulate material, e.g., with collagen. It may also comprise a molded, porous solid, or simply an aggregation of close-packed particles held in place by surrounding tissue. Masticated muscle or other tissue may also be used. Large allogeneic bone implants can act as a carrier for the matrix if their marrow cavities are cleaned and packed with particles and the dispersed osteogenic protein.

B. Preparation of Biologically Active Allogenic Matrix

Demineralized bone matrix is prepared from the dehydrated diaphyseal shafts of rat femur and tibia as described herein to produce a bone particle size which pass through a 420 mm sieve. The bone particles are subjected to dissociative extraction with 4 M guanidine-HCl. Such treatment results in a complete loss of the inherent ability of the bone matrix to induce endochondral bone differentiation. The remaining insoluble material is used to fabricate the matrix. The material is mostly collagenous in nature, and upon implantation, does not induce cartilage and bone. All new preparations are tested for mineral content and false positives before use. The total loss of biological activity of bone matrix is restored when an active osteoinductive protein fraction or a pure protein is reconstituted with the biologically inactive insoluble collagenous matrix. The osteoinductive protein can be obtained from any vertebrate, e.g., bovine, porcine, monkey, or human, or produced using recombinant DNA techniques.

C. Preparation of Deaglycosylated Bone Matrix for Use in Xenogenic Implant

When osteogenic protein is reconstituted with collagenous bone matrix from other species and implanted in rat, no bone is formed. This suggests that while the osteogenic protein is xenogenic (not species specific), while the matrix is species specific and cannot be implanted cross species perhaps due to intrinsic immunogenic or inhibitory components. Thus, heretofore, for bone-based matrices, in order for the osteogenic protein to exhibit its full bone inducing activity, a species specific collagenous bone matrix was required.

The major component of all bone matrices is Type I collagen. In addition to collagen, extracted bone includes non-collagenous proteins which may account for 5% of its mass. Many non-collagenous components of bone matrix are glycoproteins. Although the biological significance of the glycoproteins in bone formation is not known, they may present themselves as potent antigens by virtue of their carbohydrate content and may constitute immunogenic and/or inhibitory components that are present in xenogenic matrix.

It has now been discovered that a collagenous bone matrix may be used as a carrier to effect bone inducing activity in xenogenic implants, if one first removes the immonogenic and inhibitory components from the matrix. The matrix is deglycosglated chemically using, for example, hydrogen fluoride to achieve this purpose.

Bovine bone residue prepared as described above is sieved, and particles of the 74–420 mM are collected. The sample is dried in vacuo over $P_2O_5$, transferred to the reaction vessel and anhydrous hydrogen fluoride (HF) (10–20 ml/g of matrix) is then distilled onto the sample at −70° C. The vessel is allowed to warm to 0° and the reaction mixture is stirred at this temperature for 60 min. After evaporation of the HF in vacuo, the residue is dried thoroughly in vacuo over KOH pellets to remove any remaining traces of acid.

Extent of deglycosylation can be determined from carbohydrate analysis of matrix samples taken before and after treatment with HF, after washing the samples appropriately to remove non-covalently bound carbohydrates.

The deglycosylated bone matrix is next treated as set forth below:

1) suspend in TBS (Tris-buffered Saline) 1 g/200 ml and stir at 4° C. for 2 hrs;
2) centrifuge then treated again with TBS, 1 g/200 ml and stir at 4° C. overnight; and
3) cen trifu ged; discard supernatant; water wash residue; and then lyophilized.

IV. FABRICATION OF DEVICE

Fabrication of osteogenic devices using any of the matrices set forth above with any of the osteogenic proteins described above may be performed as follows.

A. Ethanol Precipitation

In this procedure, matrix was added to osteogenic protein in guanidine-HCl. Samples were vortexed and incubated at a low temperature. Samples were then further vortexed. Cold absolute ethanol was added to the mixture which was then stirred and incubated. After centrifugation (microfuge high speed) the supernatant was discarded. The reconstituted matrix was washed with cold concentrated ethanol in water and then lyophilized.

B. Acetonitrile Trifluoroacetic Acid Lyophilization

In this procedure, osteogenic protein in an acetonitrile trifluroacetic acid (ACN/TFA) solution was added to the carrier. Samples were vigorously vortexed many times and then lyophilized. Osteogenic protein was added in varying concentrations obtained at several levels of purity that have been tested to determine the most effective dose/purity level in rat in vivo assay.

C. Urea Lyophilization

For those proteins that are prepared in urea buffer, the protein is mixed with the matrix, vortexed many times, and then lyophilized. The lyophilized material may be used "as is" for implants.

V. IN VIVO RAT BIOASSAY

Substantially pure BOP, BOP-rich extracts comprising protein having the properties set forth above, and several of the synthetic proteins have been incorporated in matrices to produce osteogenic devices, and assayed in rat for endochondral bone. Studies in rats show the osteogenic effect to be dependent on the dose of osteogenic protein dispersed in the osteogenic device. No activity is observed if the matrix is implanted alone. The following sets forth guidelines for how the osteogenic devices disclosed herein might be assayed for determining active fractions of osteogenic protein when employing the isolation procedure of the invention, and evaluating protein constructs and matrices for biological activity.

A. Subcutaneous Implantation

The bioassay for bone induction as described by Sampath and Reddi (Proc. Natl. Acad. Sci. USA (1983) 80: 6591–6595), herein incorporated by reference, is used to monitor the purification protocols for endochondral bone differentiation activity. This assay consists of implanting the test samples in subcutaneous sites in allogeneic recipient rats under ether anesthesia. Male Long-Evans rats, aged 28–32 days, were used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The day of implantation is designated as day of the experiment. Implants were removed on day 12. The heterotropic site allows for the study of bone induction without the possible ambiguities resulting from the use of orthotopic sites.

B. Cellular Events

The implant model in rats exhibits a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartiliage calcification on day eight; (6) vascular invasion, appearance of osteoblasts, and formation of new bone on days nine and ten; (7) appearance of osteoblastic and bone remodeling and dissolution of the implanted matrix on days twelve to eighteen; and (8) hematopoietic bone marrow differentiation in the ossicle on day twenty-one. The results show that the shape of the new bone conforms to the shape of the implanted matrix.

C. Histological Evaluation

Histological sectioning and staining is preferred to determine the extent of osteogenesis in the implants. Implants are fixed in Bouins Solution, embedded in parafilm, cut into 6–8 mm sections. Staining with toluidine blue or hemotoxylin/eosin demonstrates clearly the ultimate development of endochondrial bone. Twelve day implants are usually sufficient to determine whether the implants show bone inducing activity.

D. Biological Markers

Alkaline phosphatase activity may be used as a marker for osteogenesis. The enzyme activity may be determined spectrophotometrically after homogenization of the implant. The activity peaks at 9–10 days in vivo and thereafter slowly declines. Implants showing no bone development by histology should have little or no alkaline phosphatase activity under these assay conditions. The assay is useful for quantitation and obtaining an estimate of bone formation very quickly after the implants are removed from the rat. In order to estimate the amount of bone formation, the calcium content of the implant is determined.

Implants containing osteogenic protein at several levels of purity have been tested to determine the most effective dose/purity level, in order to seek a formulation which could be produced on an industrial scale. The results as measured by specific acivity of alkaline phosphatase and calcium content, and histological examination. For specific activity of alkaline phosphatase is elevated during onset of bone formation and then declines. On the other hand, calcium content is directly proportional to the total amount of bone that is formed. The osteogenic activity due to osteogenic protein is represented by "bone forming units". For example, one bone forming unit represents the amount of protein that is needed for half maximal bone forming activity as compared to rat demineralized bone matrix as control and determined by calcium content of the implant on day 12.

E. Results

E-1. Natural Sourced Osteogenic Protein

Figure 11:
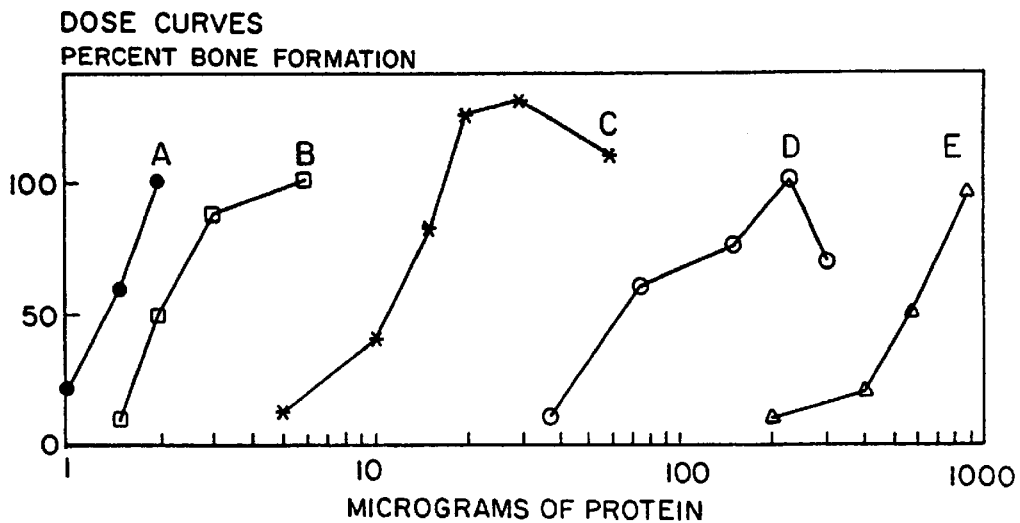
FIG. 11 is a graph showing representative dose response curves for bone-inducing activity in samples from various purification steps including reverse phase HPLC on C-18 (A), Heparin-Sepharose II (B), TSK 3000 (C), HAP-ultragel (D), and Heparin-Sepharose I (E)

Dose curves are constructed for bone inducing activity in vivo at each step of the purification scheme by assaying various concentrations of protein. FIG. 11 shows representative dose curves in rats as determined by alkaline phosphatase. Similar results are obtained when represented as bone forming units. Approximately 10–12 mg of the TSK-fraction, 3–4 mg of heparin-Sepharose-II fraction, 0.4–0.5 mg of the C-18 column purified fraction, and 20–25 ng of gel eluted highly purified 30 kD protein is needed for unequivocal bone formation (half maximum activity). 20–25 ng per 25 mg of implant is normally sufficient to produce endochondral bone. Thus, 1–2 ng osteogenic protein per mg of implant is a reasonable dosage, although higher dosages may be used. (See section IBS on specific activity of osteogenic protein.)

E-2. Xenogenic Matrix Results

Figure 19:
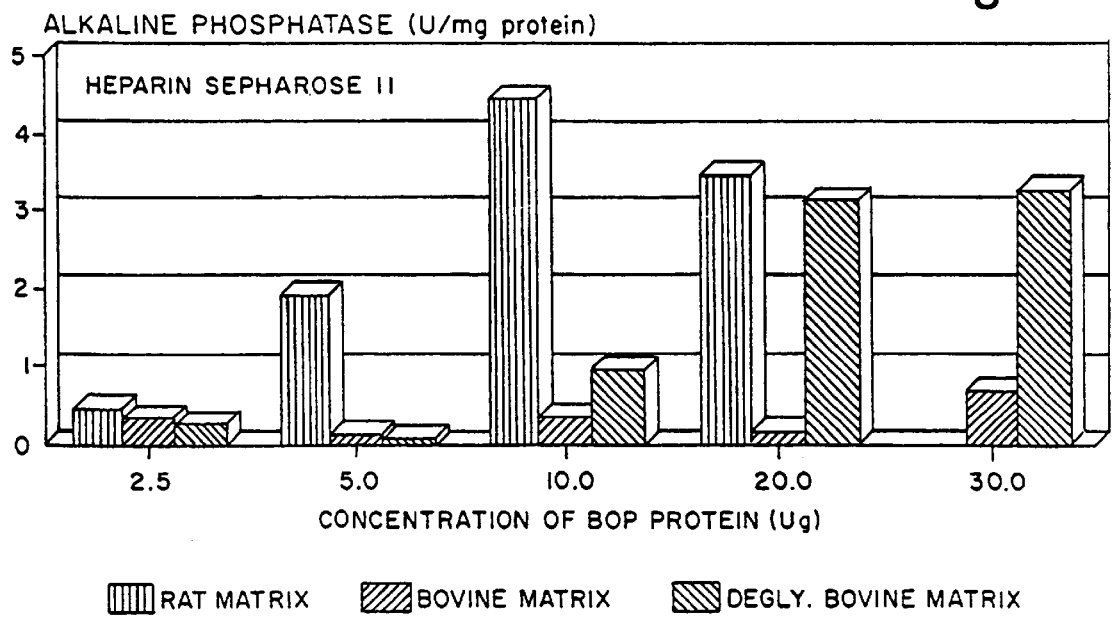
FIG. 19 is a graph illustrating the activity of xenogenic matrix (deglycolylated bovine matrix)

Deglycosylated xenogenic collagenous bone matrix (example: bovine) has been used instead of allogenic collagenous matrix to prepare osteogenic devices (see previous section) and bioassayed in rat for bone inducing activity in vivo. The results demonstrate that xenogenic collagenous bone matrix after chemical deglycosylation induces successful endochondral bone formation (FIG. 19). As shown by specific activity of alkaline phosphotase, it is evident that the deglycosylated xenogenic matrix induced bone whereas untreated bovine matrix did not.

Histological evaluation of implants suggests that the deglycosylated bovine matrix not only has induced bone in a way comparable to the rat residue matrix but also has advanced the developmental stages that are involved in endochondral bone differentiation. Compared to rat residue as control, the HF treated bovine matrix contains extensively remodeled bone. Ossicles are formed that are already filled with bone marrow elements by 12 days. This profound action as elicited by deglycosylated bovine matrix in supporting bone induction is reproducible and is dose dependent with varying concentration of osteogenic protein.

E-3. Synthetic/Recombinant Proteins (COP5, COP7)

Figure 22A:
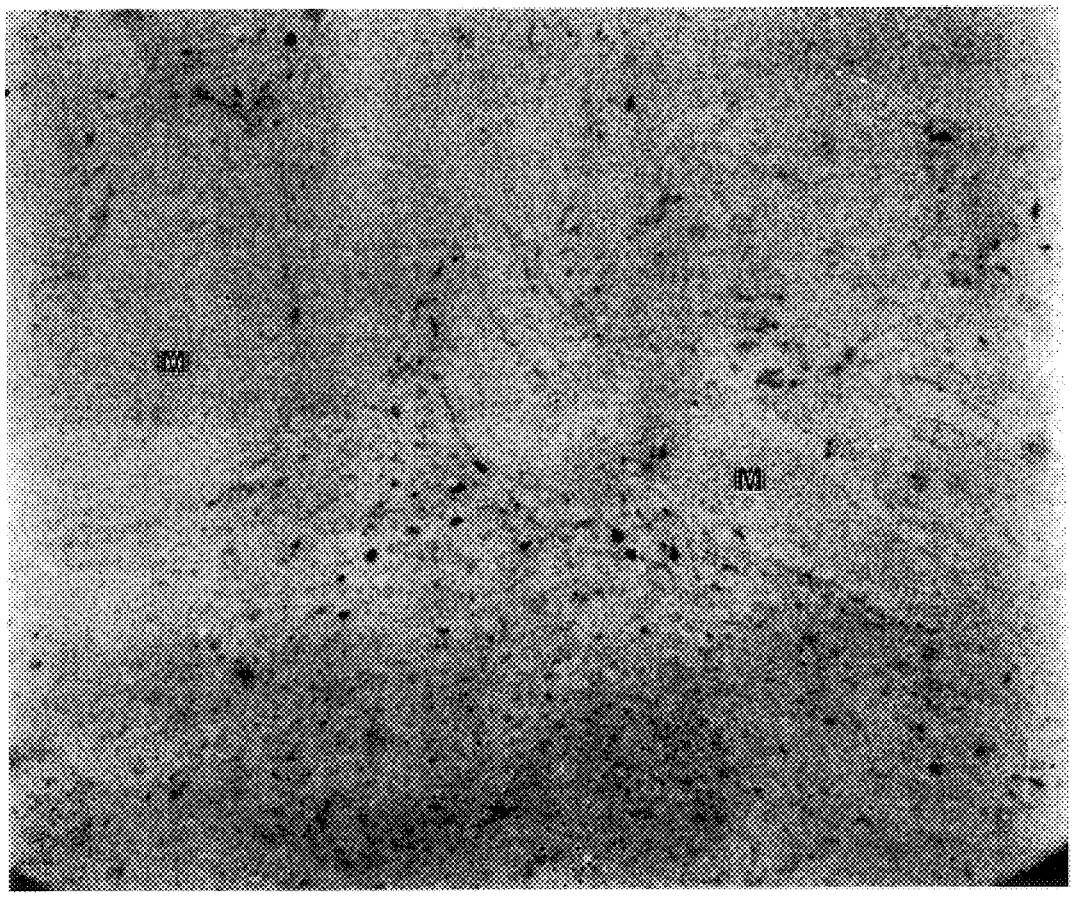
FIGS. 22A and 22B are photomicrographs of implants showing the histology (day 12) of COP5 active recombinant protein. A is a control (rat matrix alone, 25 mg). B is rat matrix plus COP5, showing +++ cartilage formation and ++ bone formation (see key infra). Similar results are achieved with COP7.

The device that contained only rat carrier showed complete absence of new bone formation. The implant consists of carrier rat matrix and surrounding mesenchymal cells. Again, the devices that contained rat carrier and not correctly folded (or biologically inactive) recombinant protein also showed complete absence of bone formation. These implants are scored as cartilage formation (−) and bone formation (−). The endochondral bone formation activity is scored as zero percent (0%). (FIG. 22A)

Implants included biologically active recombinant protein, however, showed evidence of endochondral bone formation. Histologically they showed new cartilage and bone formation.

Figure 22B:
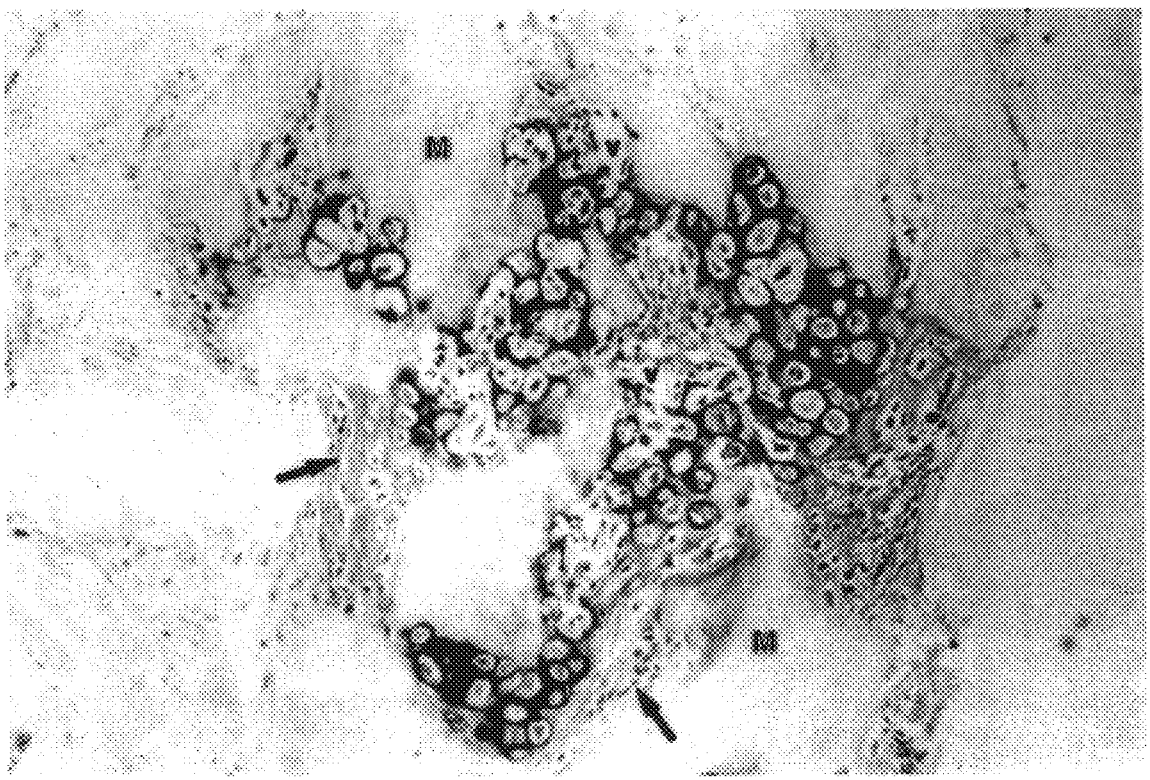

The cartilage formation is scored as (+) by the presence of metachromatically stained chondrocytes in center of the implant, as (++) by the presence of numerous chondrocytes in many areas of the implant and as (+++) by the presence of abundant chondrocytes forming cartilage matrix and the appearance of hypertrophied chondrocytes accompanying cartilage calcification (FIG. 22B).

The bone formation is scored as (+) by the presence of osteoblast surrounding vascular endothelium forming new matrix, and as (++) by the formation of bone due to osteoblasts (as indicated by arrows) and further bone remodeling by the appearance of osteoblasts in apposition to the rat carrier. Vascular invasion is evident in these implants (FIG. 22B).

The overall bone inducing activity due to recombinant protein is represented as percent response of endochondral bone formation (see Table 7 below). The percent response means the area of the implant that is covered by newly induced cartilage and bone as shown by histology in low magnification.

TABLE 7

HISTOLOGICAL EVALUATION OF RECOMBINANT BONE INDUCTIVE PROTEINS

| Implanted Protein | Cartilage Formation | Bone Formation | Percent Response in the Implant |
| --- | --- | --- | --- |
| COP-5 | +++ | ++ | 15% |
| COP-5 | ++ | + | 5% |
| COP-7 | +++ | ++ | 30% |
| COP-7 | +++ | ++ | 20% |
| COP-7 | ++ | + | 20% |
| COP-7 | ++ | + | 10% |
| COP-7 | +++ | ++ | 30% |
| COP-7 | ++ | ++ | 20% |
| COP-5 | +++ | ++ | 20% |

VI. ANIMAL EFFICACY STUDIES

Substantially pure osteogenic protein from bovine bone (BOP). BOP-rich osteogenic fractions having the properties set forth above, and several of the synthetic/recombinant proteins have been incorporated in matrices to produce osteogenic devices. The efficacy of bone-inducing potential of these devices was tested in cat and rabbit models, and found to be potent inducers of osteogenesis, ultimately resulting in formation of mineralized bone. The following sets forth guidelines as to how the osteogenic devices disclosed herein might be used in a clinical setting.

A. Feline Model

The purpose of this study is to establish a large animal efficacy model for the testing of the osteogenic devices of the invention, and to characterize repair of massive bone defects and simulated fracture non-union encountered frequently in the practice of orthopedic surgery. The study is designed to evaluate whether implants of osteogenic protein with a carrier can enhance the regeneration of bone following injury and major reconstructive surgery by use of this large mammal model. The first step in this study design consists of the surgical preparation of a femoral osteotomy defect which, without further intervention, would consistently progress to non-union of the simulated fracture defect. The effects of implants of osteogenic devices into the created bone defects were evaluated by the following study protocol.

A-1. Procedure

Sixteen adult cats weighing less than 10 lbs. undergo unilateral preparation of a 1 cm bone defect in the right femur through a lateral surgical approach. In other experiments, a 2 cm bone defect was created. The femur is immediately internally fixed by lateral placement of an 8-hole plate to preserve the exact dimensions of the defect. There are three different types of materials implanted in the surgically created cat femoral defects: group I (n=3) is a control group which undergo the same plate fixation with implants of 4 M guanidine-HCl-treated (inactivated) cat demineralized bone matrix powder (GuHCl-DBM) (360 mg); group II (n=3) is a positive control group implanted with biologically active demineralized bone matrix powder (DBM) (360 mg); and group III (n=10) undergo a procedure identical to groups I–II, with the addition of osteogenic protein onto each of the GuHCl-DBM carrier samples. To summarize, the group III osteogenic protein-treated animals are implanted with exactly the same material as the group II animals, but with the singular addition of osteogenic protein.

All animals are allowed to ambulate ad libitum within their cages post-operatively. All cats are injected with tetracycline (25 mg/kg SQ each week for four weeks) for bone labelling. All but four group III animals are sacrificed four months after femoral, osteotomy.

A-2. Radiomorphometrics

Figure 12:
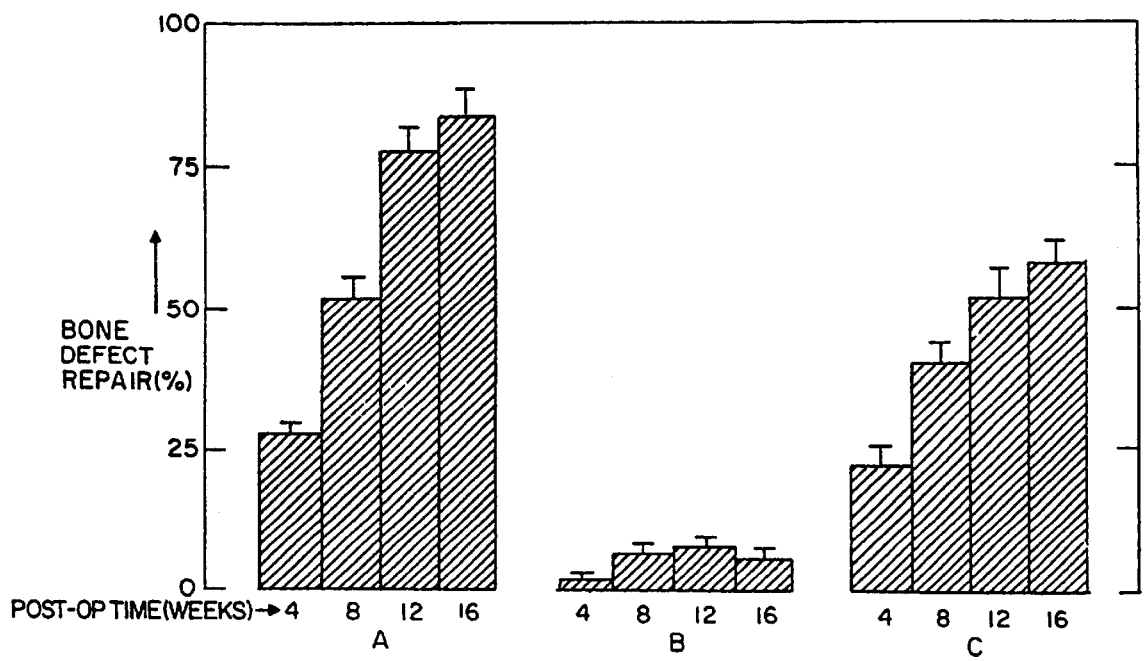
FIG. 12 is a bar graph of radiomorphometric analyses of feline bone defect repair after treatment with an osteogenic device (A), carrier control (B), and demineralized bone (C)

In vivo radiomorphometric studies are carried out immediately post-op at 4, 8, 12 and 16 weeks by taking a standardized x-ray of the lightly anesthesized animal positioned in a cushioned x-ray jig designed to consistently produce a true anterio-posterior view of the femur and the osteotomy site. All x-rays are taken in exactly the same fashion and in exactly the same position on each animal. Bone repair is calculated as a function of mineralization by means of random point analysis. A final specimen radiographic study of the excised bone is taken in two planes after sacrifice. X-ray results are shown in FIG. 12, and displaced as percent of bone defect repair. To summarize, at 16 weeks, 60% of the group III femors are united with average 86% bone defect regeneration. By contrast, the group I GuHCl-DMB negative-control implants exhibit no bone growth at four weeks, less than 10% at eight and 12 weeks, and 16% (±10%) at 16 weeks with one of the five exhibiting a small amount of bridging bone. The group II DMB positive-control implants exhibited 18% (±3%) repair at four weeks, 35% at eight weeks, 50% (±10%) at twelve weeks and 70% (±12%) by 16 weeks, a statistical difference of p<0.01 compared to osteogenic protein at every month. One of the three (33%) is united at 16 weeks.

A-3. Biomechanics

Excised test and normal femurs are immediately studied by bone densitometry, wrapped in two layers of saline-soaked towels, placed in two sealed plastic bags, and stored at −20° C. until further study. Bone repair strength, load to failure, and work to failure are tested by loading to failure on a specially designed steel 4-point bending jig attached to an Instron testing machine to quantitate bone strength, stiffness, energy absorbed and deformation to failure. The study of test femurs and normal femurs yield the bone strength (load) in pounds and work to failure in joules. Normal femurs exhibit a strength of 96 (±12) pounds. osteogenic protein-implanted femurs exhibited 35 (±4) pounds, but when corrected for surface area at the site of fracture (due to the "hourglass" shape of the bone defect repair) this correlated. closely with normal bone strength. Only one demineralized bone specimen was available for testing with a strength of 25 pounds, but, again, the strength correlated closely with normal bone when corrected for fracture surface area.

A-4. Histomorphometry/Histology

Following biomechanical testing the bones are immediately sliced into two longitudinal sections at the defect site, weighed, and the volume measured. One-half is fixed for standard calcified bone histomorphometrics with fluorescent stain incorporation evaluation, and one-half is fixed for decalcified hemotoxylin/eosin stain histology preparation.

A-5. Biochemistry

Selected specimens from the bone repair site (n=6) are homogenized in cold 0.15 M NaCl, 3 mM NaHCO$_3$, pH 9.0 by a Spex freezer mill. The alkaline phosphatase activity of the supernatant and total calcium content of the acid soluble fraction of sediment are then determined.

A-6. Histopathology

The final autopsy reports reveal no unusual or pathologic findings noted at necropsy of any of the animals studied. Portion of all major organs are preserved for further study. A histopathological evaluation is performed on samples of the following organs: heart, lung, liver, both kidneys, spleen, both adrenals, lymph nodes, left and right quadriceps muscles at mid-femur (adjacent to defect site in experimental femur). No unusual or pathological lesions are seen in any of the tissues. Mild lesions seen in the quadriceps muscles are compatible with healing responses to the surgical manipulation at the defect site. Pulmonary edema is attributable to the euthanasia procedure. There is no evidence of any general systemic effects or any effects on the specific organs examined.

A-7. Feline Study Summary

The 1 cm and 2 cm femoral defect cat studies demonstrate that devices comprising a matrix containing disposed osteogenic protein can: (1) repair a weight-bearing bone defect in a large animal; (2) consistently induces bone formation shortly following (less than two weeks) implantation; and (3) induce bone by endochondral ossification, with a strength equal to normal bone, on a volume for volume basis. Furthermore, all animals remained healthy during the study and showed no evidence of clinical or histological laboratory reaction to the implanted device. In this bone defect model, there was little or no healing at control bone implant sites. The results provide evidence for the successful use of osteogenic devices to repair large, non-union bone defects.

B. Rabbit Model

B1. Procedure and Results

Eight mature (less than 10 lbs) New Zealand White rabbits with epiphyseal closure documented by X-ray were studied. The purpose of this study is to establish a model in which there is minimal or no bone growth in the control animals, so that when bone induction is tested, only a strongly inductive substance will yield a positive result. Defects of 1.5 cm are created in.the rabbits, with implantation of: osteogenic protein (n=5), DBM (n=8), GuHCl-DBM (n=6), and no implant (n=10). Six osteogenic protein implants are supplied and all control defects have no implant placed.

Of the eight animals (one animal each was sacrificed at one and two weeks), 11 ulnae defects are followed for the full course of the eight week study. In all cases (n=7) following osteo-periosteal bone resection, the no implant animals establish no radiographic union by eight weeks. All no implant animals develop a thin "shell" of bone growing from surrounding bone present at four weeks and, to a slightly greater degree, by eight weeks. In all cases (n=4), radiographic union with marked bone induction is established in the osteogenic protein-implanted animals by eight weeks. As opposed to the no implant repairs, this bone repair is in the site of the removed bone.

Radiomorphometric analysis reveal 90% osteogenic protein-implant bone repair and 18% no-implant bone repair at sacrifice at eight weeks. At autopsy, the osteogenic protein bone appears normal, while "no implant" bone sites have only a soft fibrous tissue with no evidence of cartilage or bone repair in the defect site.

B-2. Allograft Device

In another experiment, the marrow cavity of the 1.5 cm ulnar defect is packed with activated osteogenic protein rabbit bone powder and the bones are allografted in an intercalary fashion. The two control ulnae are not healed by eight weeks and reveal the classic "ivory" appearance. In distinct contrast, the osteogenic protein-treated implants "disappear" radiographically by four weeks with the start of remineralization by six to eight weeks. These allografts heal at each end with mild proliferative bone formation by eight weeks.

This type of device serves to accelerate allograph repair.

B-3. Summary

These studies of 1.5 cm osteo-periosteal defects in the ulnae of mature rabbits show that: (1) it is a suitable model for the study of bone growth; (2) "no implant" or GuHCl negative control implants yield a small amount of periosteal-type bone, but not medullary or cortical bone growth; (3) osteogenic protein-implanted rabbits exhibited proliferative bone growth in a fashion highly different from the control groups; (4) initial studies show that the bones exhibit 50% of normal bone strength (100% of normal correlated vol:vol) at only eight weeks after creation of the surgical defect; and (5) osteogenic protein-allograft studies reveal a marked effect upon both the allograft and bone healing.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for implantation in a mammal, comprising:
    a biocompatible particulate matrix, the matrix comprising collagen and at least one material selected from the group consisting of polymers comprising lactic acid monomer units, polymers comprising glycolic acid monomer units, bone, hydroxyapatite, calcium phosphate, muscle, and tissue; and
    a substantially pure osteogenic or chondrogenic protein disposed in or on said matrix, wherein said protein induces the influx, proliferation, and differentiation of migratory precursor cells from the body of said mammal into or on said matrix.

2. The device of claim 1, wherein said particles have a particle size within the range of 70–850 μm.

3. The device of claim 1, wherein said particles have a particle size within the range of 70–420 μm.

4. The device of claim 1, wherein the matrix comprises demineralized bone.

5. The device of claim 1, wherein matrix comprises at least one synthetic material.

6. The device of claim 1 or 5, wherein the matrix comprises at least one inorganic material.

7. The device of claim 1 or 5, wherein the matrix comprises at least one biodegradeable material.

8. The device of claim 1, wherein the matrix provides a slow release delivery system for a bioactive molecule.

9. The device of claim 1, wherein the matrix acts as a scaffold for bone growth in vivo.

10. The device of claim 1, wherein the matrix is shaped to span a non-union fracture.

11. The device of claim 1, wherein said protein is glycosylated.

12. The device of claim 1, wherein said protein is unglycosylated.

13. The device of claim 1, wherein said protein is a dimeric protein.

14. The device of claim 13, wherein said dimeric protein is a homodimer.

15. The device of claim 13, wherein said dimeric protein is a heterodimer.

16. The device of claim 1, wherein said protein comprise one or more polypeptide chains, each of which has less than about 200 amino acids, in a sequence sufficiently duplicative of the sequence of COP-5 or COP-7 such that said protein is capable of inducing cartilage formation in association with said matrix when implanted in a mammal.

17. The device of claim 1, wherein said protein comprise one or more polypeptide chains, each of which has less than about 200 amino acids, in a sequence sufficiently duplicative of the sequence of COP-5 or COP-7 such that said protein is capable of inducing endochondral bone formation in association with said matrix when implanted in a mammal.

18. The device of claim 1, wherein the matrix is disposed within the marrow cavity of allogenic bone.

19. The device of claim 1, wherein said protein comprises the amino acid sequence shown in FIG. 13.

20. The device of claim 1, wherein said protein is selected from the group consisting of Vgl, DPP, OP-1, CBMP-2a, CBMP-2b, CBMP-3, COP1, COP2, COP3, COP4, COP5, COP7, and COP16.

21. The device of claim 1, wherein the matrix and the protein are held in place by surrounding tissue within the body of the mammal.

22. The device of claim 1, wherein said matrix and said osteogenic protein are association with a defect within a bone.

23. The device of claim 1, wherein the defect is a non-union fracture.

24. The device of claim 1, wherein the matrix and protein are associated with the marrow cavity of a bone.

* * * * *